US010940194B2

(12) United States Patent
Li et al.

(10) Patent No.: US 10,940,194 B2
(45) Date of Patent: Mar. 9, 2021

(54) MUTANT OF L1 PROTEIN OF HUMAN PAPILLOMAVIRUS TYPE 58

(71) Applicants: Xiamen University, Xiamen (CN); Xiamen Innovax Biotech Co., Ltd., Xiamen (CN)

(72) Inventors: Shaowei Li, Xiamen (CN); Zhihai Li, Xiamen (CN); Shuo Song, Xiamen (CN); Maozhou He, Xiamen (CN); Ying Gu, Xiamen (CN); Ningshao Xia, Xiamen (CN)

(73) Assignees: Xiamen University, Xiamen (CN); Xiamen Innovax Biotech Co., Ltd., Xiamen (CN)

( * ) Notice: Subject to any disclaimer, the term of this patent is extended or adjusted under 35 U.S.C. 154(b) by 286 days.

(21) Appl. No.: 15/781,035

(22) PCT Filed: Dec. 2, 2016

(86) PCT No.: PCT/CN2016/108345
§ 371 (c)(1),
(2) Date: Jun. 1, 2018

(87) PCT Pub. No.: WO2017/092710
PCT Pub. Date: Jun. 8, 2017

(65) Prior Publication Data
US 2020/0268869 A1     Aug. 27, 2020

(30) Foreign Application Priority Data

Dec. 4, 2015   (CN) .......................... 201510882847.1

(51) Int. Cl.
| | |
|---|---|
| *A61K 39/12* | (2006.01) |
| *C07K 14/025* | (2006.01) |
| *C12N 7/00* | (2006.01) |
| *C12N 15/70* | (2006.01) |
| *A61P 31/20* | (2006.01) |
| *C07K 14/005* | (2006.01) |
| *A61K 39/00* | (2006.01) |

(52) U.S. Cl.
CPC .............. *A61K 39/12* (2013.01); *A61P 31/20* (2018.01); *C07K 14/005* (2013.01); *C12N 7/00* (2013.01); *C12N 15/70* (2013.01); *A61K 2039/5258* (2013.01); *C12N 2710/20022* (2013.01); *C12N 2710/20023* (2013.01); *C12N 2710/20043* (2013.01)

(58) Field of Classification Search
None
See application file for complete search history.

(56) References Cited

U.S. PATENT DOCUMENTS

| | | | |
|---|---|---|---|
| 2005/0058988 A1 | 3/2005 | Jansen et al. | |
| 2007/0036824 A1* | 2/2007 | Bryan | ............... A61P 37/04 424/204.1 |
| 2012/0087937 A1 | 4/2012 | Colau | |
| 2012/0093821 A1 | 4/2012 | Roden | |
| 2013/0230548 A1 | 9/2013 | Li | |
| 2013/0314594 A1 | 11/2013 | Li | |
| 2013/0315943 A1* | 11/2013 | Li | ............... A61P 35/00 424/186.1 |
| 2014/0147460 A1 | 5/2014 | Li | |

FOREIGN PATENT DOCUMENTS

| | | |
|---|---|---|
| CN | 101518647 A | 9/2009 |
| CN | 102229660 A | 11/2011 |
| CN | 102268076 A | 12/2011 |
| CN | 102336822 A | 2/2012 |
| CN | 102458440 A | 5/2012 |
| CN | 102497880 A | 6/2012 |
| CN | 102552897 A | 7/2012 |
| CN | 103483447 A | 1/2014 |
| CN | 103992395 A | 8/2014 |
| CN | 104231060 A | 12/2014 |
| WO | 00/54730 | 9/2000 |
| WO | 2004/084831 A2 | 10/2004 |
| WO | 2010/149752 | 12/2010 |

OTHER PUBLICATIONS

Combita et al. Identification of Two Cross-Neutralizing Linear Epitopes within the L1 Major Capsid Protein of Human Papillomaviruses. J. Virol. 2002, 76: 6480-6486.*
Zhu, Pan et al., Fusion Expression of Truncated L1 Protein of Human Papilloma Virus Type 58 and Early Secreted Antigenic Target-6 Protein of *Mycobacterium tuberculosis* and Preparation of Antiserum; Chin J. Biologicals. Apr. 2013, vol. 26, No. 4, pp. 534-538.
PCT/CN2016/108345 International Search Report dated Mar. 1, 2017.
Chen, Zuyi, et al., L1 and L2 gene polymorphisms in HPV-58 and HPV-33: Implications for Vaccine Design and Diagnosis, Virology Journal (2016) 13:167.

(Continued)

*Primary Examiner* — Nianxiang Zou
(74) *Attorney, Agent, or Firm* — Honigman LLP; Thomas A. Wootton, Esq.; Jonathan P. O'Brien

(57) ABSTRACT

Provided are a mutated HPV58 L1 protein or a variant thereof, a sequence encoding the same, a method for preparing the same, and a virus-like particle comprising the same, wherein the protein or a variant thereof and the virus-like particle can induce the generation of neutralizing antibodies against at least two HPV types, and therefore can be used to prevent infection by said at least two HPV types, and a disease caused by said infection, such as cervical cancer and condyloma acuminatum. The invention further relates to the use of the protein and the virus-like particle in the manufacture of a pharmaceutical composition or a vaccine for preventing infection by said at least two HPV types, and a disease caused by said infection, such as cervical cancer and condyloma acuminatum.

26 Claims, 9 Drawing Sheets
Specification includes a Sequence Listing.

(56) References Cited

OTHER PUBLICATIONS

Ma, Zhenghai, et al., Increasing the expression levels of papillomavirus major capsid protein in *Escherichia coli* by N-terminal deletion, Protein Expression & Purification, 56 (2007) 72-79, ScienceDirect, Elsevier, Inc.

Bissett, Sara L., et al, Pre-clinical immunogenicity of human papillomavirus alpha-7 and alpha-9 major capsid proteins; Vaccine 32 (2014) 6548-6555, Elsevier.

\* cited by examiner

MUTANT OF L1 PROTEIN OF HUMAN PAPILLOMAVIRUS TYPE 58

CROSS-REFERENCE TO RELATED APPLICATIONS

This application is National Stage Application and claims priority under 35 U.S.C. § 371 to Patent Cooperation Treaty application PCT/CN2016/108345, filed Dec. 2, 2016, which claims the benefit of Chinese Patent Application No. 201510882847.1, filed Dec. 4, 2015, priory is claimed to both of these applications and the disclosures of these prior applications are considered part of the disclosure of this application and to the extent allowed the entire contents of the aforementioned applications are incorporated herein.

SEQUENCE LISTING

This application incorporates in its entirety the Sequence Listing entitled "2018-06-01_235427-433854-Sequence_Listing_ST25.txt" (96,208 bytes), which was created on Jun. 1, 2018 and filed electronically herewith.

TECHNICAL FIELD

The invention relates to the field of molecular virology and immunology. In particular, the invention relates to a mutated HPV58 L1 protein (or a variant thereof), a sequence encoding the same, a method for preparing the same, and a virus-like particle comprising the same, wherein the protein (or a variant thereof) and the virus-like particle can induce the generation of neutralizing antibodies against at least two HPV types (e.g. HPV58 and HPV33, or HPV58, HPV33 and HPV52), and therefore can be used to prevent infection by said at least two HPV types, and a disease caused by said infection, such as cervical cancer and condyloma acuminatum. The invention further relates to the use of the protein and the virus-like particle in the manufacture of a pharmaceutical composition or a vaccine for preventing infection by said at least two HPV types, and a disease caused by said infection, such as cervical cancer and condyloma acuminatum.

BACKGROUND ART

Human Papillomavirus (HPV) mainly causes warts in skin and mucosa. HPV types are divided into high-risk types and low-risk types depending on their association with tumorigenesis. Among them, infection by high-risk HPV types has been demonstrated to be the leading cause of genital cancer including cervical cancer in women; and low-risk HPV types mainly cause condyloma acuminatum. The most effective way to prevent and control HPV infection is to administer HPV vaccines, particularly vaccines against high-risk HPV types causing cervical cancer.

Major capsid protein L1 of HPV has the characteristic of self-assembling into hollow Virus-Like Particle (VLP). HPV VLP has a symmetrical icosahedral structure composed of 72 pentamers of major capsid protein L1 (Doorbar, J. and P. H. Gallimore. 1987. J Virol, 61(9): 2793-9). HPV VLP is highly similar to natural HPV in terms of structure, retains most of the neutralizing epitopes of natural virus, and can induce the generation of high-titer neutralizing antibodies (Kirnbauer, R., F. Booy, et al. 1992 Proc Natl Acad Sci USA 89(24): 12180-4).

However, the existing studies show that HPV VLPs mainly induce the generation of neutralizing antibodies against the same HPV type, produce the protective immunity against the same HPV type, and only have low cross-protective effect among a few highly homologous HPV types (Sara L. Bissett, Giada Mattiuzzo, et al. 2014 Vaccine. 32:6548-6555). Therefore, the existing HPV vaccines have a very limited protection range. In general, VLP of one HPV type can only be used to prevent infection by the same HPV type. In this case, if it needs to broaden the protection range of HPV vaccines, the only way is to add VLPs of more HPV types in vaccines. Currently, the commercially available HPV vaccines, including Gardasil® from Merck (which is a quadrivalent vaccine against HPV16, 18, 6 and 11), Cervarix® from GSK (which is a bivalent vaccine against HPV16 and 18), and Gardasil®9 from Merck (which is a 9-valent vaccine), are prepared by combining VLPs of multiple HPV types. However, such a solution would greatly increase the production cost of HPV vaccines, and might cause safety problem due to an increase in immunizing dose.

Therefore, it is urgent in the art to develop HPV virus-like particles capable of inducing the generation of protective neutralizing antibodies against multiple HPV types, so as to prevent infection by multiple HPV types, and a disease caused by the infection, such as cervical cancer and condyloma acuminatum, more economically and effectively.

Contents of Invention

The invention is at least partially based on the inventors' surprising discovery: after substitution of a specific segment of L1 protein of Human Papillomavirus (HPV) Type 58 with the corresponding segment of L1 protein of a second HPV type (such as HPV33), the mutated HPV58 L1 protein thus obtained can induce the generation of high-titer neutralizing antibodies against HPV58 and the second HPV type (such as HPV33) in organisms, and its protection effect is comparable to that of a mixture of HPV58 VLP and VLP of the second HPV type, its protection effect against HPV58 is comparable to that of HPV58 VLP alone, and its protection effect against the second HPV type (such as HPV33) is comparable to that of the VLP of the second HPV type alone.

In addition, based on the substitution above, another specific segment of HPV58 L1 protein can be further substituted with the corresponding segment of L1 protein of a third HPV type (such as HPV52), and the mutated HPV58 L1 protein having double substitutions thus obtained can induce the generation of high-titer neutralizing antibodies against HPV58, the second HPV type (such as HPV33) and the third HPV type (such as HPV52); and its protection effect is comparable to that of a mixture of HPV58 VLP, VLP of the second HPV type and VLP of the third HPV type, its protection effect against HPV58 is comparable to that of HPV58 VLP alone, its protection effect against the second HPV type (such as HPV33) is comparable to that of the VLP of the second HPV type alone, and its protection effect against the third HPV type (such as HPV52) is comparable to that of the VLP of the third HPV type alone.

Therefore, in an aspect, the invention provides a mutated HPV58 L1 protein or a variant thereof, wherein as compared with a wild type HPV58 L1 protein, the mutated HPV58 L1 protein has the following mutations:

(1) N-terminal truncation of 5-70 amino acids, for example 5-60, 15-60, 20-50, 30-45, or 35-40 amino acids; and (2) (a) substitution of amino acid residues at positions 80-87 of the wild type HPV58 L1 protein with amino acid residues at the corresponding positions of a L1 protein of a second type of wild-type HPV; or (b) substitution of amino acid residues at positions 376-383 of the wild type HPV58 L1 protein with amino acid residues at the corresponding positions of a L1 protein of a second type of wild-type HPV;

and, the variant differs from the mutated HPV58 L1 protein only by substitution (preferably conservative substitution), addition or deletion of one or several (e.g. 1, 2, 3, 4, 5, 6, 7, 8 or 9) amino acids, and retains the function of the mutated HPV58 L1 protein, i.e. capability of inducing generation of neutralizing antibodies against at least two HPV types (e.g. HPV58 and HPV33, or HPV58, HPV33 and HPV52).

In some preferred embodiments, the mutated HPV58 L1 protein has the mutation as defined in (2) (a), and optionally, further has the following mutation:

(3) substitution of amino acid residues at positions 375-383 of the wild type HPV58 L1 protein with amino acid residues at the corresponding positions of a L1 protein of a third type of wild-type HPV; or (4) substitution of amino acid residues at positions 144-168 of the wild type HPV58 L1 protein with amino acid residues at the corresponding positions of a L1 protein of a third type of wild-type HPV.

In some preferred embodiments, the mutated HPV58 L1 protein has 5, 15, 27, 35, 40, 60 or 70 amino acids truncated at N-terminal, as compared with the wild type HPV58 L1 protein.

In some preferred embodiments, the mutated HPV58 L1 protein has 35 amino acids truncated at N-terminal, as compared with the wild type HPV58 L1 protein.

In some preferred embodiments, said second type of wild-type HPV is HPV33. In some preferred embodiments, the amino acid residues at the corresponding positions as described in (2) (a) are amino acid residues at positions 54-61 of a wild type HPV33 L1 protein. In some preferred embodiments, the amino acid residues at the corresponding positions as described in (2) (b) are amino acid residues at positions 350-357 of a wild type HPV33 L1 protein In some preferred embodiments, said third type of wild-type HPV is HPV52. In some preferred embodiments, the amino acid residues at the corresponding positions as described in (3) are amino acid residues at positions 380-388 of a wild type HPV52 L1 protein. In some preferred embodiments, the amino acid residues at the corresponding positions as described in (4) are amino acid residues at positions 146-170 of a wild type HPV52 L1 protein.

In some preferred embodiments, the wild type HPV58 L1 protein has an amino acid sequence as set forth in SEQ ID NO: 1.

In some preferred embodiments, the wild type HPV33 L1 protein has an amino acid sequence as set forth in SEQ ID NO: 2.

In some preferred embodiments, the wild type HPV52 L1 protein has an amino acid sequence as set forth in SEQ ID NO: 3.

In some preferred embodiments, the amino acid residues at positions 54 to 61 of the wild type HPV33 L1 protein have a sequence as set forth in SEQ ID NO: 59.

In some preferred embodiments, the amino acid residues at positions 350 to 357 of the wild type HPV33 L1 protein have a sequence as set forth in SEQ ID NO: 60.

In some preferred embodiments, the amino acid residues at positions 146 to 170 of the wild type HPV52 L1 protein have a sequence as set forth in SEQ ID NO: 61.

In some preferred embodiments, the amino acid residues at positions 380 to 388 of the wild type HPV52 L1 protein have a sequence as set forth in SEQ ID NO: 62.

In some preferred embodiments, the mutated HPV58 L1 protein has an amino acid sequence selected from the group consisting of: SEQ ID NO: 4, 10, 11 and 14.

In another aspect, the invention provides an isolated nucleic acid, encoding the mutated HPV58 L1 protein or a variant thereof as described above. In another aspect, the invention provides a vector comprising the isolated nucleic acid. In some preferred embodiments, the isolated nucleic acid according to the invention has a nucleotide sequence selected from the group consisting of: SEQ ID NOs: 18, 24, 25 and 28.

Vectors useful for insertion of a polynucleotide of interest are well known in the art, including, but not limited to cloning vectors and expression vectors. In one embodiment, the vectors are, for example, plasmids, cosmids, phages, etc.

In another aspect, the invention further relates to a host cell comprising the isolated nucleic acid or the vector. The host cell includes, but is not limited to prokaryotic cells such as *E. coli* cells, and eukaryotic cells such as yeast cells, insect cells, plant cells and animal cells (such as mammalian cells, for example, mouse cells, human cells, etc.). The host cell according to the invention may also be a cell line, such as 293T cell.

In another aspect, the invention relates to a HPV virus-like particle, comprising or consisting of the mutated HPV58 L1 protein or a variant thereof according to the invention.

In some preferred embodiments, the HPV virus-like particle according to the invention comprises the mutated HPV58 L1 protein, which has N-terminal truncation of 5-70 amino acids, for example, 5-60, 15-60, 20-50, 30-45, 35-40 amino acids, e.g. 5, 15, 27, 35, 40, 60 or 70 amino acids, as compared to a wild type HPV58 L1 protein, and substitution of the amino acid residues at positions 80-87 of the wild type HPV58 L1 protein with the amino acid residues at positions 54-61 of a wild type HPV33 L1 protein.

In some preferred embodiments, the HPV virus-like particle according to the invention comprises the mutated HPV58 L1 protein, which has N-terminal truncation of 5-70 amino acids, for example, 5-60, 15-60, 20-50, 30-45, 35-40 amino acids, e.g. 5, 15, 27, 35, 40, 60 or 70 amino acids, as compared to a wild type HPV58 L1 protein, and substitution of the amino acid residues at positions 376-383 of the wild type HPV58 L1 protein with the amino acid residues at positions 350-357 of a wild type HPV33 L1 protein.

In some preferred embodiments, the HPV virus-like particle according to the invention comprises the mutated HPV58 L1 protein, which has N-terminal truncation of 5-70 amino acids, for example, 5-60, 15-60, 20-50, 30-45, 35-40 amino acids, e.g. 5, 15, 27, 35, 40, 60 or 70 amino acids, as compared with a wild type HPV58 L1 protein, and substitution of the amino acid residues at positions 80-87 of the wild type HPV58 L1 protein with the amino acid residues at positions 54-61 of a wild type HPV33 L1 protein, and substitution of the amino acid residues at positions 144-168 of the wild type HPV58 L1 protein with the amino acid residues at positions 146-170 of a wild type HPV52 L1 protein.

In some preferred embodiments, the HPV virus-like particle according to the invention comprises the mutated HPV58 L1 protein, which has N-terminal truncation of 5-70 amino acids, for example, 5-60, 15-60, 20-50, 30-45, 35-40 amino acids, e.g. 5, 15, 27, 35, 40, 60 or 70 amino acids, as compared with a wild type HPV58 L1 protein, and substitution of the amino acid residues at positions 80-87 of the wild type HPV58 L1 protein with the amino acid residues at positions 54-61 of a wild type HPV33 L1 protein, and substitution of the amino acid residues at positions 375-383 of the wild type HPV58 L1 protein with the amino acid residues at positions 380-388 of a wild type HPV52 L1 protein.

In a particularly preferred embodiment, the HPV virus-like particle according to the invention comprises the mutated HPV58 L1 protein, which has a sequence as set forth in SEQ ID NO: 4, 10, 11 or 14.

In another aspect, the invention further relates to a composition comprising the mutated HPV58 L1 protein or a variant thereof, the isolated nucleic acid, the vector, the host cell, or the HPV virus-like particle. In some preferred embodiments, the composition comprises the mutated HPV58 L1 protein or a variant thereof according to the invention. In some preferred embodiments, the composition comprises the HPV virus-like particle according to the invention.

In another aspect, the invention further relates to a pharmaceutical composition or vaccine, comprising the HPV virus-like particle according to the invention, and optionally a pharmaceutically acceptable carrier and/or excipient. The pharmaceutical composition or vaccine according to the invention can be used for preventing HPV infection, or a disease caused by HPV infection, such as cervical cancer and condyloma acuminatum.

In some preferred embodiments, the HPV virus-like particle is present in an amount effective for preventing HPV infection or a disease caused by HPV infection. In some preferred embodiments, the HPV infection is infection by one or more HPV types (e.g. HPV58 infection, HPV33 infection and/or HPV52 infection). In some preferred embodiments, the disease caused by HPV infection is selected from the group consisting of cervical cancer and condyloma acuminatum.

The pharmaceutical composition or vaccine according to the invention may be administered by methods well known in the art, for example, but not limited to, orally or by injection. In the invention, a particularly preferred administration route is injection.

In some preferred embodiments, the pharmaceutical composition or vaccine according to the invention is administrated in a form of a unit dosage. For example, but not for limiting the invention, each unit dosage contains 5 µg-80 µg, preferably 20 µg-40 µg of HPV virus-like particle.

In another aspect, the invention relates to a method for preparing the mutated HPV58 L1 protein or a variant thereof as described above, comprising expressing the mutated HPV58 L1 protein or a variant thereof in a host cell, and then recovering the mutated HPV58 L1 protein or a variant thereof from a culture of the host cell.

In some preferred embodiments, the host cell is *E. coli*.

In some preferred embodiments, the method comprises the steps of: expressing the mutated HPV58 L1 protein or a variant thereof in *E. coli*, and then obtaining the mutated HPV58 L1 protein or a variant thereof by purifying a lysate supernatant of the *E. coli*. In some preferred embodiments, the mutated HPV58 L1 protein or a variant thereof is recovered from the lysate supernatant of the *E. coli* by chromatography (e.g. cation-exchange chromatography, hydroxyapatite chromatography and/or hydrophobic interaction chromatography).

In another aspect, the invention relates to a method for preparing a vaccine, comprising combining the HPV virus-like particle according to the invention with a pharmaceutically acceptable carrier and/or excipient.

In another aspect, the invention relates to a method for preventing HPV infection or a disease caused by HPV infection, comprising administering to a subject a prophylactically effective amount of the HPV virus-like particle or the pharmaceutical composition or vaccine according to the invention. In a preferred embodiment, the HPV infection is infection by one or more HPV types (e.g. HPV58 infection, HPV33 infection and/or HPV52 infection). In another preferred embodiment, the disease caused by HPV infection includes, but is not limited to cervical cancer and condyloma acuminatum. In another preferred embodiment, the subject is mammal, such as human.

In another aspect, the invention further relates to use of the mutated HPV58 L1 protein or a variant thereof or the HPV virus-like particle according to the invention in the manufacture of a pharmaceutical composition or vaccine for preventing HPV infection or a disease caused by HPV infection. In a preferred embodiment, the HPV infection is infection by one or more HPV types (e.g. HPV58 infection, HPV33 infection and/or HPV52 infection). In another preferred embodiment, the disease caused by HPV infection includes, but is not limited to, cervical cancer and condyloma acuminatum.

Definitions of Terms in Present Invention

In the invention, unless otherwise specified, the scientific and technical terms used herein have the meanings generally understood by a person skilled in the art. Moreover, the laboratory operations of cell culture, molecular genetics, nucleic acid chemistry, and immunology used herein are the routine operations widely used in the corresponding fields. Meanwhile, in order to better understand the invention, the definitions and explanations of the relevant terms are provided as follows.

According to the invention, the term "a second type of wild-type HPV" refers to a wild-type HPV type other than HPV58. In the invention, a second type of wild-type HPV is preferably wild type HPV33. According to the invention, the term "a third type of wild-type HPV" refers to a wild-type HPV type other than HPV58 and the second type of wild-type HPV. In the invention, a third type of wild-type HPV is preferably wild type HPV52.

According to the invention, the expression "corresponding positions" refers to the equivalent positions of the sequences being compared when the sequences are optimally aligned, i.e. the sequences are aligned to obtain a highest percentage of identity.

According to the invention, the term "wild type HPV58 L1 protein" refers to the naturally-occurring major capsid protein L1 in Human Papillomavirus Type 58 (HPV58). The sequence of wild type HPV58 L1 protein is well known in the art, and can be found in public database (such as Accession No. P26535.1, ACJ13480, ACX32376.1 and ACK37663.1 in NCBI database).

In the invention, when an amino acid sequence of wild type HPV58 L1 protein is mentioned, it is described by reference to the sequence as set forth in SEQ ID NO: 1. For example, the expression "amino acid residues at positions 80-87 of a wild type HPV58 L1 protein" refers to the amino acid residues at positions 80-87 of the polypeptide as set forth in SEQ ID NO: 1. However, a person skilled in the art understands that wild type HPV58 may include various isolates, and there might be difference in the amino acid sequence of L1 protein among various isolates. Furthermore, a person skilled in the art understands that although there might be difference in sequence, the amino acid sequences of L1 protein have a very high identity (generally higher than 95%, e.g. higher than 96%, higher than 97%, higher than 98%, or higher than 99%) among different HPV58 isolates, and have substantively the same biological function. Therefore, in the invention, the term "wild type HPV58 L1 protein" includes not only the protein as set forth in SEQ ID NO: 1, but also L1 protein of various HPV58 isolates (such as HPV58 L1 protein as set forth in P26535.1, ACJ13480, ACX32376.1 or ACK37663.1). Moreover, when a sequence fragment of a wild type HPV58 L1 protein is described, it includes not only the sequence fragment of SEQ ID NO: 1, but also the corresponding sequence fragment of a L1 protein of various HPV58 isolates. For example, the expression "amino acid residues at positions 80-87 of a wild type HPV58 L1 protein" includes the amino acid residues at positions 80-87 of SEQ ID NO: 1, and the corresponding fragment of a L1 protein of various HPV58 isolates.

According to the invention, the term "wild type HPV33 L1 protein" refers to the naturally-occurring major capsid protein L1 in Human Papillomavirus Type 33 (HPV33). The sequence of wild type HPV33 L1 protein is well known in the art, and can be found in public database (such as Accession No. P06416.1, ACV84008.1, ACV84011.1, ACV84012.1 and ACL12333.1 in NCBI database).

In the invention, when an amino acid sequence of wild type HPV33 L1 protein is mentioned, it is described by reference to the sequence as set forth in SEQ ID NO: 2. For example, the expression "amino acid residues at positions 54-61 of a wild type HPV33 L1 protein" refers to the amino acid residues at positions 54-61 of the polypeptide as set forth in SEQ ID NO: 2. However, a person skilled in the art understands that wild type HPV33 may include various isolates, and there might be difference in the amino acid sequence of L1 protein among various isolates. Furthermore, a person skilled in the art understands that although there might be difference in sequence, the amino acid sequences of L1 protein have a very high identity (generally higher than 95%, e.g. higher than 96%, higher than 97%, higher than 98%, or higher than 99%) among different HPV33 isolates, and have substantively the same biological function. Therefore, in the invention, the term "wild type HPV33 L1 protein" includes not only the protein as set forth in SEQ ID NO: 2, but also L1 protein of various HPV33 isolates (such as HPV33 L1 protein as set forth in P06416.1, ACV84008.1, ACV84011.1, ACV84012.1 or ACL12333.1). Moreover, when a sequence fragment of a wild type HPV33 L1 protein is described, it includes not only the sequence fragment of SEQ ID NO: 2, but also the corresponding sequence fragment of a L1 protein of various HPV33 isolates. For example, the expression "amino acid residues at positions 54-61 of a wild type HPV33 L1 protein" includes the amino acid residues at positions 54-61 of SEQ ID NO: 2, and the corresponding fragment of a L1 protein of various HPV33 isolates.

According to the invention, the term "wild type HPV52 L1 protein" refers to the naturally-occurring major capsid protein L1 in Human Papillomavirus Type 52 (HPV52). The sequence of wild type HPV52 L1 protein is well known in the art, and can be found in public database (such as Accession No. ACX32362.1, Q05138.2 or ABU55790.1 in NCBI database).

In the invention, when an amino acid sequence of wild type HPV52 L1 protein is mentioned, it is described by reference to the sequence as set forth in SEQ ID NO: 3. For example, the expression "amino acid residues at positions 146-170 of a wild type HPV52 L1 protein" refers to amino acid residues at positions 146-170 of the polypeptide as set forth in SEQ ID NO: 3. However, a person skilled in the art understands that wild type HPV52 may include various isolates, and there might be difference in the amino acid sequence of L1 protein among various isolates. Furthermore, a person skilled in the art understands that although there might be difference in sequence, the amino acid sequences of L1 protein have a very high identity (generally higher than 95%, e.g. higher than 96%, higher than 97%, higher than 98%, or higher than 99%) among different HPV52 isolates, and have substantively the same biological function. Therefore, in the invention, the term "wild type HPV52 L1 protein" includes not only the protein as set forth in SEQ ID NO: 3, but also L1 protein of various HPV52 isolates (such as HPV52 L1 protein as set forth in ACX32362.1, Q05138.2 or ABU55790.1). Moreover, when a sequence fragment of a wild type HPV52 L1 protein is described, it includes not only the sequence fragment of SEQ ID NO: 3, but also the corresponding sequence fragment of L1 protein of various HPV52 isolates. For example, the expression "amino acid residues at positions 146-170 of a wild type HPV52 L1 protein" includes the amino acid residues at positions 146-170 of SEQ ID NO: 3, and the corresponding fragment of L1 protein of various HPV52 isolates.

According to the invention, the expression "corresponding sequence fragments" or "corresponding fragments" refers to the fragments that are located at equivalent positions of the sequences being compared when the sequences are optimally aligned, i.e. the sequences are aligned to obtain a highest percentage of identity.

According to the invention, the expression "N-terminal truncation of X amino acids" or "having X amino acids truncated at N-terminal" refers to substitution of the amino acid residues from positions 1 to X at the N-terminal of a protein with methionine residue encoded by an initiator codon (for initiating protein translation). For example, a HPV58 L1 protein having 35 amino acids truncated at N-terminal refers to a protein resulted from substituting the amino acid residues from positions 1 to 35 at the N-terminal of wild type HPV58 L1 protein with methionine residue encoded by an initiator codon.

According to the invention, the term "variant" refers to a protein, whose amino acid sequence has substitution (preferably conservative substitution), addition or deletion of one or several (e.g. 1, 2, 3, 4, 5, 6, 7, 8 or 9) amino acids, or has an identity of at least 90%, 95%, 96%, 97%, 98%, or 99%, as compared with the mutated HPV58 L1 protein according to the invention (for example, the protein as set forth in SEQ ID NO: 4, 10, 11 and 14), and which retains a function of the mutated HPV58 L1 protein according to the invention. In the invention, the term "function of the mutated HPV58 L1 protein" refers to a capability of inducing generation of neutralizing antibodies against at least two HPV types (e.g. HPV58 and HPV33, or HPV58, HPV33 and HPV52). The term "identity" refers to a measure of similarity between nucleotide sequences or amino acid sequences. Generally, sequences were aligned to obtain a maximum matching. "Identity" has well-known meanings in the art and can be calculated by published algorithm (such as BLAST).

According to the invention, the term "identity" refers to the match degree between two polypeptides or between two nucleic acids. When two sequences for comparison have the same monomer sub-unit of base or amino acid at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by for example using a computer program such as Align program (DNAstar, Inc.) which is based on the method of Needleman, et al. (J. Mol. Biol. 48:443-453, 1970). The percent identity between two amino acid sequences can also be determined using the algorithm of E. Meyers and W. Miller (Comput. Appl. Biosci., 4:11-17 (1988)) which has been incorporated into the ALIGN program (version 2.0), using a PAM120 weight residue table, and with a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and with a gap weight of 16, 14, 12, 10, 8, 6, or 4 and a length weight of 1, 2, 3, 4, 5, or 6.

As used herein, the term "conservative substitution" refers to amino acid substitutions which would not disadvantageously affect or change the essential properties of a protein/polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having basic side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having β-branched side chains (such as threonine, valine, isoleucine) and amino acids having aromatic side chains (for example, tyrosine, phenylalanine, tryptophan, histidine). Therefore, generally a conservative substitution refers to a substitution of a corresponding amino acid residue with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl. Acad. Sci. USA 94: 412-417 (1997), which are incorporated herein by reference).

According to the invention, the term "E. coli expression system" refers to an expression system consisting of E. coli (strain) and a vector, wherein the E. coli (strain) is derived from the commercially available strains, including, but not limited to: ER2566, BL21 (DE3), B834 (DE3), and BLR (DE3).

According to the invention, the term "vector" refers to a nucleic acid carrier tool which can have a polynucleotide inserted therein. When the vector allows for the expression of the protein encoded by the polynucleotide inserted therein, the vector is called an expression vector. The vector can have the carried genetic material elements expressed in a host cell by transformation, transduction, or transfection into the host cell. Vectors are well known by a person skilled in the art, including, but not limited to plasmids, phages, cosmids, etc.

According to the invention, the term "a pharmaceutically acceptable carrier and/or excipient" refers to a carrier and/or excipient that is pharmacologically and/or physiologically compatible to a subject and active ingredients, which is well known in the art (see, for example, Remington's Pharmaceutical Sciences. Edited by Gennaro A R, 19th ed. Pennsylvania: Mack Publishing Company, 1995), including, but not limited to: pH regulators, surfactants, adjuvants, and ionic strength enhancers. For example, pH regulators include, but are not limited to, phosphate buffers; surfactants include, but are not limited to: cation surfactants, anion surfactants, or non-ionic surfactants, e.g., Tween-80; adjuvants include, but are not limited to, aluminium adjuvant (e.g., aluminium hydroxide), and Freund's adjuvant (e.g., Freund's complete adjuvant); and ionic strength enhancers include, but are not limited to, NaCl.

According to the invention, the term "an effective amount" refers to an amount that can effectively achieve the intended purpose. For example, an amount effective for preventing a disease (such as HPV infection) refers to an amount effective for preventing, suppressing, or delaying the occurrence of a disease (such as HPV infection). The determination of such an effective amount is within the ability of a person skilled in the art.

According to the invention, the term "chromatography" includes, but is not limited to: ion exchange chromatography (such as cation-exchange chromatography), hydrophobic interaction chromatography, absorbent chromatography (such as hydroxyapatite chromatography), gel filtration chromatography (gel exclusion chromatography), and affinity chromatography.

According to the invention, the term "lysate supernatant" refers to a solution produced by the following steps: host cells (such as E. coli) are disrupted in a lysis buffer, and the insoluble substances are then removed from the lysed solution containing the disrupted host cells. Various lysis buffers are well known in the art, including, but not limited to Tris buffers, phosphate buffers, HEPES buffers, MOPS buffers, etc. In addition, the disrupting of a host cell can be accomplished by methods well known by a person skilled in the art, including, but not limited to homogenizer disrupting, ultrasonic treatment, grinding, high pressure extrusion, lysozyme treatment, etc. Methods for removing insoluble substances are also well known by a person skilled in the art, including, but not limited to filtration and centrifugation.

Beneficial Effects of Invention

Studies show that although there is certain cross-protection between HPV58 and other HPV type(s) (such as HPV33 and HPV52), such cross-protection is very low, generally lower than one percent, even one thousandth of the protection level of VLP of the same HPV type. Therefore, a subject vaccinated with HPV58 vaccine, still has a high risk of being infected by other HPV type(s) (such as HPV33 and HPV52).

The invention provides a mutated HPV58 L1 protein and a HPV virus-like particle formed by the same. The HPV virus-like particle according to the invention can provide significant cross-protection against HPV58 and other HPV type(s) (such as HPV33 and HPV52). Especially, at the same immunizing dose, the HPV virus-like particle according to the invention can induce the generation of high-titer neutralizing antibodies against at least two HPV types (e.g. HPV58 and HPV33, or HPV58, HPV33 and HPV52) in organisms, and its effect is comparable to that of a mixture of VLPs of multiple HPV types (e.g. a mixture of HPV58 VLP and HPV33 VLP, or a mixture of HPV58 VLP, HPV33 VLP and HPV52 VLP). Therefore, the HPV virus-like particle according to the invention can be used to prevent infection by at least two HPV types (e.g. HPV58 and HPV33, or HPV58, HPV33 and HPV52) at the same time as well as diseases associated with the infection, and has significantly beneficial technical effects. This has particularly significant advantages in terms of extending the protection range of HPV vaccines and reducing the production cost of HPV vaccines.

The embodiments of the invention are further described in detail by reference to the drawings and examples. However, a person skilled in the art would understand that the following drawings and examples are intended for illustrating the invention only, rather than defining the scope of the invention. According to the detailed description of the following drawings and preferred embodiments, various purposes and advantages of the invention are apparent for a person skilled in the art.

DESCRIPTION OF DRAWINGS

FIG. 4A, HPV58N35 VLP; FIG. 4B, HPV33N9 VLP; FIG. 4C, HPV52N40 VLP; FIG. 4D, H58N35-33T1 VLP; FIG. 4E, H58N35-33T1-52S1 VLP; FIG. 4F, H58N35-33T1-52S4 VLP. The results showed that the sedimentation coefficient of H58N35-33T1 VLP, H58N35-33T1-52S1 VLP and H58N35-33T1-52S4 VLP was 109S, 113S and 109S, respectively, while the sedimentation coefficient of HPV58N35 VLP, HPV33N9 VLP and HPV52N40 VLP was 118S, 133S and 131S, respectively. This showed that H58N35-33T1, H58N35-33T1-52S1 and H58N35-33T1-52S4 were able to assemble into virus-like particles that were similar to wild type VLP in terms of size and morphology.

FIG. 5A, VLP assembled by HPV58N35; FIG. 5B, VLP assembled by H58N35-33T1; FIG. 5C, pentamer formed by H58N35-33T2, which failed to further assemble into VLP; FIG. 5D, VLP assembled by H58N35-33T3; FIG. 5E, VLP assembled by H58N35-33T4; FIG. 5F, VLP assembled by H58N35-33T5; FIG. 5G, VLP assembled by HPV33N9; FIG. 5H, VLP assembled by H58N35-33T1-52S1; FIG. 5I, VLP assembled by H58N35-33T1-52S2; FIG. 5J, VLP assembled by H58N35-33T1-52S3; FIG. 5K, VLP assembled by H58N35-33T1-52S4; FIG. 5L, VLP assembled by HPV52N40. The results showed that H58N35-33T1, H58N35-33T3, H58N35-33T4, H58N35-33T5, H58N35-33T1-52S1, H58N35-33T1-52S2, H58N35-33T1-52S3 and H58N35-33T1-52S4 were similar to HPV58N35, HPV33N9 and HPV52N40, and were able to assemble into VLPs with a radius of about 30 nm; while H58N35-33T2 could only form a pentamer with a radius of about 5 nm, and was unable to assemble into VLP.

FIG. 6A, HPV58N35 VLP; FIG. 6B, H58N35-33T1 VLP; FIG. 6C, H58N35-33T1-52S1 VLP; FIG. 6D, H58N35-33T1-52S1 VLP; FIG. 6E, H58N35-33T1-52S1 VLP; FIG. 6F, H58N35-33T1-52S4 VLP. The results showed that all the VLPs formed by these proteins had very high thermostability.

FIG. 8A: Aluminum adjuvant group 1 (at an immunizing dose of 10 μg, using aluminum adjuvant); FIG. 8B: Aluminum adjuvant group 2 (at an immunizing dose of 1 μg, using aluminum adjuvant); FIG. 8C: Aluminum adjuvant group 3 (at an immunizing dose of 0.1 μg, using aluminum adjuvant); FIG. 8D: Freund's adjuvant group (at an immunizing dose of 1 μg, using Freund's adjuvant). The result showed that H58N35-33T1 VLP could induce the generation of high-titer neutralizing antibodies against HPV58 in mice, and its protective effect was comparable to that of HPV58N35 VLP alone at the same dose, and was significantly superior to that of HPV33N9 VLP alone at the same dose; and it could induce the generation of high-titer neutralizing antibodies against HPV33 in mice, and its protective effect was comparable to that of HPV33N9 VLP alone at the same dose, and was significantly superior to that of HPV58N35 VLP alone at the same dose. This showed that H58N35-33T1 VLP had good cross-immunogenicity and cross-protection against HPV58 and HPV33.

FIG. 8E: Aluminum adjuvant group 1 (at an immunizing dose of 10 μg, using aluminum adjuvant); FIG. 8F: Aluminum adjuvant group 2 (at an immunizing dose of 1 μg, using aluminum adjuvant); FIG. 8G: Aluminum adjuvant group 3 (at an immunizing dose of 0.1 μg, using aluminum adjuvant). The result showed that H58N35-33T1-52S1 VLP and H58N35-33T1-52S4 VLP could induce the generation of high-titer neutralizing antibodies against HPV58 in mice, and its protective effect was comparable to that of HPV58N35 VLP alone and that of a mixture of HPV58N35 VLP, HPV33N9 VLP and HPV52N40 VLP at the same dose, and was significantly superior to that of HPV33N9 VLP alone or HPV52N40 VLP alone at the same dose; and they could induce the generation of high-titer neutralizing antibodies against HPV33 in mice, and their protective effect was comparable to that of HPV33N9 VLP alone and that of a mixture of HPV58N35 VLP, HPV33N9 VLP and HPV52N40 VLP at the same dose, and was significantly superior to that of HPV58N35 VLP alone or HPV52N40 VLP alone at the same dose; and they could induce the generation of high-titer neutralizing antibodies against HPV52 in mice, and their protective effect was slightly weaker than that of HPV52N40 VLP alone and that of a mixture of HPV58N35 VLP, HPV33N9 VLP and HPV52N40 VLP at the same dose, but was significantly superior to that of HPV58N35 VLP alone or HPV33N9 VLP alone at the same dose. This showed that H58N35-33T1-52S1 VLP and H58N35-33T1-52S4 VLP had good cross-immunogenicity and cross-protection against HPV58, HPV33 and HPV52.

FIG. 10A, the cryo-electron microscopy (cryoEM) photograph of H58N35-33T1 VLP; FIG. 10B, the reconstructed three-dimensional structure of H58N35-33T1 VLP; FIG. 10C, the cryo-electron microscopy (cryoEM) photograph of H58N35-33T1-52S4 VLP; FIG. 10D, the reconstructed three-dimensional structure of H58N35-33T1-52S4 VLP. The reconstructed three-dimensional structures showed that both H58N35-33T1 VLP and H58N35-33T1-52S4 VLP had a T=7 icosahedral structure (h=1, k=2) consisting of 72 capsomers (morphological subunit, pentamer). Unlike conventional icosahedral viral capsids consistent with quasi-equivalence principle, all the constitutive subunits in the structures of H58N35-33T1 VLP and H58N35-33T1-52S4 VLP were pentamers, without hexamer. Moreover, said two VLPs had an external diameter of about 60 nm. These were similar to the three-dimensional structures of the previously reported natural HPV viral particles and the HPV VLP prepared by eukaryotic expression system (e.g. poxvirus expression system) (Baker T S, Newcomb W W, Olson N H. et al. Biophys J. (1991), 60(6): 1445-1456. Hagensee M E, Olson N H, Baker T S, et al. J Virol. (1994), 68(7):4503-4505. Buck C B, Cheng N, Thompson C D. et al. J Virol. (2008), 82(11): 5190-7).

Sequence Information

Figure 1:
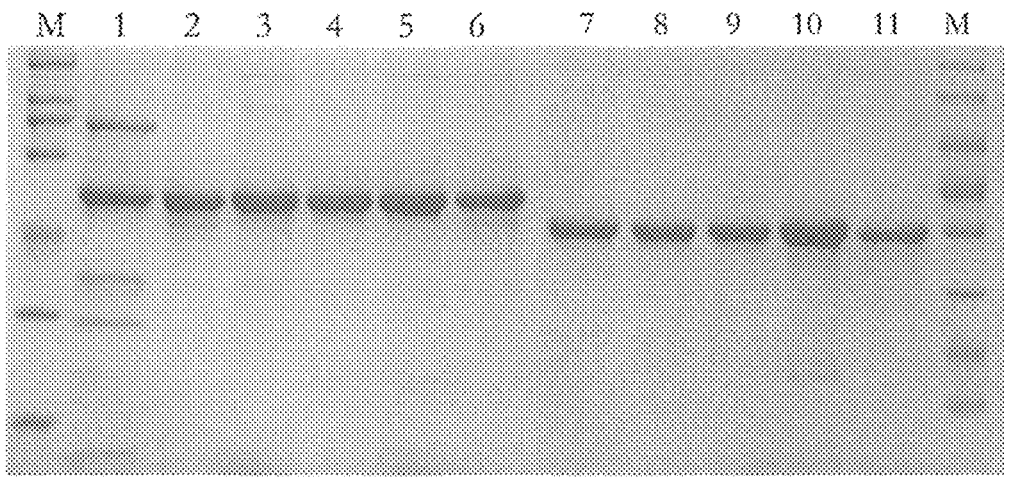
FIG. 1 shows the SDS-PAGE result of the purified mutated proteins in Example 1. Lane M: protein molecular weight marker; Lane 1: HPV58N35 (HPV58 L1 protein having 35 amino acids truncated at N-terminal); Lane 2: H58N35-33T1; Lane 3: H58N35-33T2; Lane 4: H58N35-33T3; Lane 5: H58N35-33T4; Lane 6: H58N35-33T5; Lane 7: H58N35-33T1; Lane 8: H58N35-33T1-52S1; Lane 9: H58N35-33T1-52S2; Lane 10: H58N35-33T1-52S3; Lane 11: H58N35-33T1-52S4. The result showed that after chromatographic purification, H58N35-33T1, 1158N35-33T2, H58N35-33T3, H58N35-33T4, H58N35-33T5, H58N35-33T1-52S1, H58N35-33T1-52S2, H58N35-33T1-52S3, and H58N35-33T1-52S4 protein reached a purity of above 95%.

Some of the sequences involved in the invention are provided in the following Table 1.

TABLE 1

Description of sequences

| SEQ ID NO: | Description |
| --- | --- |
| 1 | wild type HPV58 L1 protein |
| 2 | wild type HPV33 L1 protein |
| 3 | wild type HPV52 L1 protein |
| 4 | the mutated HPV58 L1 protein comprising Segment 1 of HPV33 L1 protein, H58N35-33T1 |
| 5 | H58N35-33T2-1 |
| 6 | H58N35-33T2-2 |
| 7 | the mutated HPV58 L1 protein comprising Segment 2 of HPV33 L1 protein, H58N35-33T2 |
| 8 | the mutated HPV58 L1 protein comprising Segment 3 of HPV33 L1 protein, H58N35-33T3 |
| 9 | the mutated HPV58 L1 protein comprising Segment 4 of HPV33 L1 protein, H58N35-33T4 |
| 10 | the mutated HPV58 L1 protein comprising Segment 5 of HPV33 L1 protein, H58N35-33T5 |
| 11 | the mutated HPV58 L1 protein comprising Segment 1 of HPV33 L1 protein and Segment 1 of HPV52 L1 protein, H58N35-33T1-52S1 |
| 12 | the mutated HPV58 L1 protein comprising Segment 1 of HPV33 L1 protein and Segment 2 of HPV52 L1 protein, H58N35-33T1-52S2 |
| 13 | the mutated HPV58 L1 protein comprising Segment 1 of HPV33 L1 protein and Segment 3 of HPV52 L1 protein, H58N35-33T1-52S3 |
| 14 | the mutated HPV58 L1 protein comprising Segment 1 of HPV33 L1 protein and Segment 4 of HPV52 L1 protein, H58N35-33T1-52S4 |
| 15 | the DNA sequence encoding SEQ ID NO: 1 |
| 16 | the DNA sequence encoding SEQ ID NO: 2 |
| 17 | the DNA sequence encoding SEQ ID NO: 3 |
| 18 | the DNA sequence encoding SEQ ID NO: 4 |
| 19 | the DNA sequence encoding SEQ ID NO: 5 |
| 20 | the DNA sequence encoding SEQ ID NO: 6 |
| 21 | the DNA sequence encoding SEQ ID NO: 7 |
| 22 | the DNA sequence encoding SEQ ID NO: 8 |
| 23 | the DNA sequence encoding SEQ ID NO: 9 |
| 24 | the DNA sequence encoding SEQ ID NO: 10 |
| 25 | the DNA sequence encoding SEQ ID NO: 11 |
| 26 | the DNA sequence encoding SEQ ID NO: 12 |
| 27 | the DNA sequence encoding SEQ ID NO: 13 |
| 28 | the DNA sequence encoding SEQ ID NO: 14 |
| 59 | the sequence of the amino acid residues at positions 54 to 61 of wild type HPV33 L1 protein |
| 60 | the sequence of the amino acid residues at positions 350 to 357 of wild type HPV33 L1 protein |
| 61 | the sequence of the amino acid residues at positions 146 to 170 of wild type HPV52 L1 protein |
| 62 | the sequence of the amino acid residues at positions 380 to 388 of wild type HPV52 L1 protein |

```
Sequence 1 (SEQ ID NO: 1):
MVLILCCTLAILFCVADVNVFHIFLQMSVWRPSEATVYLPPVPVSKVVSTDEYVSRTSIYYYAGSSRLL

AVGNPYFSIKSPNNNKKVLVPKVSGLQYRVFRVRLPDPNKFGFPDTSFYNPDTQRLVWACVGLEIGR

GQPLGVGVSGHPYLNKFDDTETSNRYPAQPGSDNRECLSMDYKQTQLCLIGCKPPTGEHWGKGVAC

NNNAAATDCPPLELFNSIIEDGDMVDTGFGCMDFGTLQANKSDVPIDICNSTCKYPDYLKMASEPYG

DSLFFFLRREQMFVRHFFNRAGKLGEAVPDDLYIKGSGNTAVIQSSAFFPTPSGSIVTSESQLFNKPYW

LQRAQGHNNGICWGNQLFVTVVDTTRSTNMTLCTEVTKEGTYKNDNFKEYVRHVEEYDLQFVFQLC

KITLTAEIMTYIHTMDSNILEDWQFGLTPPPSASLQDTYRFVTSQAITCQKTAPPKEKEDPLNKYTFWE

VNLKEKFSADLDQFPLGRKFLLQSGLKAKPRLKRSAPTTRAPSTKRKKVKK

Sequence 2 (SEQ ID NO: 2):
MSVWRPSEATVYLPPVPVSKVVSTDEYVSRTSIYYYAGSSRLLAVGHPYFSIKNPTNAKKLLVPKVSG

LQYRVFRVRLPDPNICFGFPDTSFYNPDTQRLVWACVGLEIGRGQPLGVGISGHPLLNKFDDTETGNK
```

YPGQPGADNRECLSMDYKQTQLCLLGCKPPTGEHWGKGVACINAAPANDCPPLELINTIIEDGDMVD

TGFGCNIEDFKTLQANICSDVPIDICGSTCKYPDYLKMTSEPYGDSLFFFLRREQMFVRHFFNRAGTLGEA

VPDDLYIKGSGTTASIQSSAFFPTP SGSMVTSESQLFNKPYWLQRAQGHNNGICWGNQVFVTVVDTTR

STNMLCTQVTSDSTYKNENFKEYIRHVEEYDLQFVFQLCKVTLTAEVMTYIHAMNPDILEDWQFGL

TPPPSASLQDTYRFVTSQAITCQKTVPPKEKEDPLGKYTFWEVDLICEKFSADLDQFPLGRICFLLQAGL

KAKPKLKRAAPTSTRTSSAICRICKVICK

Sequence 3 (SEQ ID NO: 3):
MVQILFYILVIFYYVAGVNVFHIFLQMSVWRPSEATVYLPPVPVSKVVSTDEYVSRTSIYYYAGSSRLL

TVGHPYFSIKNTSSGNGKKVLVPKVSGLQYRVFRIKLPDPNKFGFPDTSFYNPETQRLVWACTGLEIG

RGQPLGVGISGHPLLNKFDDTETSNKYAGKPGIDNRECLSMDYKQTQLCILGCKPPIGEHWGKGTPCN

NNSGNPGDCPPLQL1NSVIQDGDMVDTGFGCMDFNTLQASKSDVPIDICSSVCKYPDYLQMASEPYGD

SLFFFLRREQMFVRHFFNRAGTLGDPVPGDLYIQGSNSGNTATVQSSAFFPTPSGSMVTSESQLFNKPY

WLQRAQGHNNGICWGNQLFVTVVDTTRSINMTLCAEVICKESTYKNENFICEYLRHGEEFDLQFIFQL

CKITLTADVMTYIHKMDATILEDWQFGLTPPPSASLEDTYRFVTSTAITCQKNTPPKGKEDPLKDYMF

WEVDLKEKFSADLDQFPLGRICFLLQAGLQARPKLKRPASSAPRTSTKICICKVICR

Sequence 4 (SEQ ID NO: 4):
MTVYLPPVPVSKVVSTDEYVSRTSIYYYAGSSRLLAVGNPYFSIKNPTNAKKLLVPKVSGLQYRVFRV

RLPDPNICFGFPDTSFYNPDTQRLVWACVGLEIGRGQPLGVGVSGHPYLNKFDDTETSNRYPAQPGSD

NRECLSMDYKQTQLCLIGCKPPTGEHWGKGVACNNNAAATDCPPLELFNSIIEDGDMVDTGFGCMD

FGTLQANKSDVPIDICNSTCKYPDYLKMASEPYGDSLFFFLRREQMFVRHFFNRAGKLGEAVPDDLYI

KGSGNTAVIQSSAFFPTPSGSIVTSESQLFNICPYWLQRAQGHNNGICWGNQLFVTVVDTIRSTNMTLC

TEVTKEGTYKNDNFKEYVRHVEEYDLQFVFQLCKITLTAEIMTYIHTMDSNILEDWQFGLTPPPSASL

QDTYRFVTSQAITCQKTAPPKEKEDPLNKYTFWEVNLICEKFSADLDQFPLGRKFLLQSGLKAKPRLK

RSAPTTRAPSTKRKKVICK

Sequence 5 (SEQ ID NO: 5):
MTVYLPPVPVSKVVSTDEYVSRTSIYYYAGSSRLLAVGNPYFSIKSPNNNICKVLVPKVSGLQYRVFRV

RLPDPNKFGFPDTSFYNPDTQRLVWACVGLEIGRGQPLGVGISGHPLLNKFDDTETSNRYPAQPGSDN

RECLSMDYKQTQLCLIGCKPPTGEHWGKGVACNNNAAATDCPPLELFNSIIEDGDMVDTGFGCMDF

GTLQANKSDVPIDICNSTCKYPDYLICMASEPYGDSLFFFLRREQMFVRHFFNRAGICLGEAVPDDLYIK

GSGNTAVIQSSAFFPTPSGSIVTSESQLFNKPYWLQRAQGHNNGICWGNQLFVTVVDTTRSTNMTLCT

EVTKEGTYKNDNFKEYVRHVEEYDLQFVFQLCKITLTAEIMTYIHTMDSNILEDWQFGLTPPPSASLQ

DTYRFVTSQAITCQKTAPPKEKEDPLNKYTFWEVNLKEKFSADLDQFPLGRKFLLQSGLKAKPRLICRS

APTTRAPSTKRKKVKK

Sequence 6 (SEQ ID NO: 6):
MTVYLPPVPVSKVVSTDEYVSRTSIYYYAGSSRLLAVGNPYFSIKSPNNNKICVLVPKVSGLQYRVFRV

RLPDPNKFGFPDTSFYNPDTQRLVWACVGLEIGRGQPLGVGISGHPLLNKFDDTETGNKYPAQPGSDN

RECLSMDYKQTQLCLIGCKPPTGEHWGKGVACNNNAAATDCPPLELFNSIIEDGDMVDTGFGCMDF

GTLQANKSDVPIDICNSTCKYPDYLKMASEPYGDSLFFFLRREQMFVRHFFNRAGICLGEAVPDDLYIK

GSGNTAVIQSSAFFPTPSGSIVTSESQLFNKPYWLQRAQGHNNGICWGNQLFVTVVDTTRSTNMTLCT

EVTKEGTYKNDNFKEYVRHVEEYDLQFVFQLCKITLTAEIMTYIHTMDSNILEDWQFGLTPPPSASLQ

DTYRFVTSQAITCQKTAPPICEKEDPLNKYTFWEVNLKEICFSADLDQFPLGRKFLLQSGLKAKPRLICRS

APTTRAPSTKRKKVICK

Sequence 7 (SEQ ID NO: 7):
MTVYLPPVPVSKVVSTDEYVSRTSIYYYAGSSRLLAVGNPYFSIKSPNNNKKVLVPKVSGLQYRVFRV
RLPDPNKFGFPDTSFYNPDTQRLVWACVGLEIGRGQPLGVGISGHPLLNICFDDTETGNKYPGQPGAD
NRECLSMDYKQTQLCLIGCKPPTGEHWGKGVACNNNAAATDCPPLELFNSIIEDGDMVDTGFGCMD
FGTLQANKSDVPIDICNSTCKYPDYLKMASEPYGDSLFFFLRREQMFVRHFFNRAGKLGEAVPDDLYI
KGSGNTAVIQSSAFFPTPSGSIVTSESQLFNKPYWLQRAQGHNNGICWGNQLFVTVVDTIRSTNMTLC
TEVTKEGTYICNDNFKEYVRHVEEYDLQFVFQLCKITLTAEIMTY1HTMDSNILEDWQFGLTPPPSASL
QDTYRFVTSQAITCQKTAPPICEKEDPLNKYTFWEVNLKEKFSADLDQFPLGRKFLLQSGLKAKPRLK
RSAPTTRAPSTKRICKVICK Sequence 8 (SEQ ID NO: 8):
MTVYLPPVPVSKVVSTDEYVSRTSIYYYAGSSRLLAVGNPYFSIKSPNNNKKVLVPKVSGLQYRVFRV
RLPDPNICFGFPDTSFYNPDTQRLVWACVGLEIGRGQPLGVGVSGHPYLNKFDDTETSNRYPAQPGSD
NRECLSMDYKQTQLCLIGCKPPTGEHWGKGVACTNAAPANDCPPLELFNSIIEDGDMVDTGFGCMDF
GTLQANKSDVPIDICNSTCKYPDYLICMASEPYGDSLFFFLRREQMFVRHFFNRAGKLGEAVPDDLYIK
GSGNTAVIQ SSAFFPTP SGSIVTSESQLFNICPYWLQRAQGHNNGICWGNQLFVTVVDTTRSTNMTLCT
EVTKEGTYKNDNFKEYVRHVEEYDLQFVFQLCKITLTAEIMTYIHTMDSNILEDWQFGLTPPPSASLQ
DTYRFVTSQAITCQKTAPPKEKEDPLNKYTFWEVNLKEKFSADLDQFPLGRKFLLQSGLKAKPRLKRS
APTTRAPSTKRKKVKK Sequence 9 (SEQ ID NO: 9):
MTVYLPPVPVSKVVSTDEYVSRTSIYYYAGSSRLLAVGNPYFSIKSPNNNKKVLVPKVSGLQYRVFRV
RLPDPNKFGFPDTSFYNPDTQRLVWACVGLEIGRGQPLGVGVSGHPYLNICFDDTETSNRYPAQPGSD
NRECLSMDYKQTQLCLIGCKPPTGEHWGKGVACNNNAAATDCPPLELFNSIIEDGDMVDTGFGCMD
FGTLQANKSDVPIDICNSTCKYPDYLKMASEPYGDSLFFFLRREQMFVRHFFNRAGKLGEAVPDDLYI
KGSGTTASIQSSAFFPTPSGSIVTSESQLFNKPYWLQRAQGHNNGICWGNQLFVTVVDTTRSTNMTLC
TEVTKEGTYKNDNFKEYVRHVEEYDLQFVFQLCKITLTAEIMTYIEITMDSNILEDWQFGLTPPPSASL
QDTYRFVTSQATTCQKTAPPKEKEDPLNKYTFWEVNLICEKFSADLDQFPLGRICFLLQSGLKAKPRLK
RSAPTTRAPSTICRIUCVKK Sequence 10 (SEQ ID NO: 10):
MTVYLPPVPVSKVVSTDEYVSRTSIYYYAGSSRLLAVGNPYFSIKSPNNNKKVLVPKVSGLQYRVFRV
RLPDPNICFGFPDTSFYNPDTQRLVWACVGLEIGRGQPLGVGVSGHPYLNKFDDTETSNRYPAQPGSD
NRECLSMDYKQTQLCLIGCKPPTGEHWGKGVACNNNAAATDCPPLELFNSIIEDGDMVDTGFGCMD
FGTLQANICSDVPIDICNSTCKYPDYLKMASEPYGDSLFFFLRREQMFVRHFFNRAGICLGEAVPDDLYI
KGSGNTAVIQSSAFFPTPSGSIVTSESQLFNICPYWLQRAQGHNNGICWGNQLFVTVVDTTRSTNMTLC
TEVTSDSTYKNENFKEYVRHVEEYDLQFVFQLCKTTLTAEIMTYIHTMDSNILEDWQFGLTPPPSASLQ
DTYRFVTSQAITCQKTAPPKEKEDPLNKYTFWEVNLKEKFSADLDQFPLGRKFLLQSGLKAKPRLKRS
APTTRAPSTKRIUCVKK Sequence 11 (SEQ ID NO: 11):
MTVYLPPVPVSKVVSTDEYVSRTSIYYYAGSSRLLAVGNPYFSIKNPTNAICKLLVPKVSGLQYRVFRV
RLPDPNICFGFPDTSFYNPDTQRLVWACVGLEIGRGQPLGVGISGHPLLNICFDDTETSNKYAGKPGIDN
RECLSMDYKQTQLCLIGCKPPTGEHWGKGVACNNNAAATDCPPLELFNSIIEDGDMVDTGFGCMDF
GTLQANKSDVPIDICNSTCKYPDYLICMASEPYGDSLFFFLRREQMFVRHFFNRAGICLGEAVPDDLYIK
GSGNTAVIQSSAFFPTPSGSIVTSESQLFNKPYWLQRAQGHNNGICWGNQLFVTVVDTTRSTNMTLCT
EVTKEGTYKNDNFKEYVRHVEEYDLQFVFQLCKITLTAEIMTYIHTMDSNILEDWQFGLTPPPSASLQ -continued

DTYRFVTSQAITCQKTAPPKEICEDPLNKYTFWEVNLKEKFSADLDQFPLGRICFLLQSGLKAICPRLICRS

APTTRAPSTICRKKVICK

Sequence 12 (SEQ ID NO: 12):
MTVYLPPVPVSKVVSTDEYVSRTSIYYYAGSSRLLAVGNPYFSIKNPTNAKKLLVPKVSGLQYRVFRV

RLPDPNKFGFPDTSFYNPDTQRLVWACVGLEIGRGQPLGVGVSGHPYLNICFDDTETSNRYPAQPGSD

NRECLSMDYKQTQLCLIGCKPPTGEHWGKGTPCNNNSGNPGDCPPLELFNSIIEDGDMVDTGFGCMD

FGTLQANKSDVPIDICNSTCKYPDYLKMASEPYGDSLFFFLRREQMFVRHFFNRAGKLGEAVPDDLYI

KGSGNTAVIQSSAFFPTPSGSIVTSESQLFNKPYWLQRAQGHNNGICWGNQLFVTVVDTTRSTNMTLC

TEVTKEGTYKNDNFKEYVRHVEEYDLQFVFQLCKITLTAEIMTYIFITMDSNILEDWQFGLTPPPSASL

QDTYRFVTSQAITCQKTAPPKEKEDPLNKYTFWEVNLKEKFSADLDQFPLGRKFLLQSGLKAKPRLK

RSAPTTRAPSTICRICKVICK

Sequence 13 (SEQ ID NO: 13):
MTVYLPPVPVSKVVSTDEYVSRTSIYYYAGSSRLLAVGNPYFSIKNPTNAKKLLVPKVSGLQYRVFRV

RLPDPNKFGFPDTSFYNPDTQRLVWACVGLEIGRGQPLGVGVSGHPYLNICFDDTETSNRYPAQPGSD

NRECLSMDYKQTQLCLIGCKPPTGEHWGKGVACNNNAAATDCPPLELFNSIIEDGDMVDTGFGCMD

FGTLQANKSDVPIDICNSTCKYPDYLKMASEPYGDSLFFFLRREQMFVRHFFNRAGTLGDPVPGDLYI

QGSNSGNTATVQSSAFFPTPSGSIVTSESQLFNKPYWLQRAQGHNNGICWGNQLFVTVVDTTRSTNM

TLCTEVTKEGTYKNDNFKEYVRHVEEYDLQFVFQLCKITLTAEIMTYIHTMDSNILEDWQFGLTPPPS

ASLQDTYRFVTSQAITCQKTAPPKEKEDPLNKYTFWEVNLKEKFSADLDQFPLGRKFLLQSGLKAKPR

LKRSAPTTRAPSTKRKKVICK

Sequence 14 (SEQ ID NO: 14):
MTVYLPPVPVSICVVSTDEYVSRTSIYYYAGSSRLLAVGNPYFSIKNPTNAKICLLVPKVSGLQYRVFRV

RLPDPNKFGFPDTSFYNPDTQRLVINACVGLEIGRGQPLGVGVSGHPYLNICFDDTETSNRYPAQPGSD

NRECLSMDYKQTQLCLIGCKPPTGEHWGKGVACNNNAAATDCPPLELFNSIIEDGDMVDTGFGCMD

FGTLQANKSDVPIDICNSTCKYPDYLKMASEPYGDSLFFFLRREQMFVRHFFNRAGKLGEAVPDDLYI

KGSGNTAVIQSSAFFPTPSGSIVTSESQLFNKPYWLQRAQGHNNGICWGNQLFVTVVDTTRSTNMTLC

TEVKKESTYKNENFKEYVRHVEEYDLQFVFQLCKITLTAEIMTYIHTMDSNILEDWQFGLTPPPSASLQ

DTYRFVTSQAITCQKTAPPKEKEDPLNKYTFWEVNLKEKFSADLDQFPLGRKFLLQSGLKAKPRLKRS

APTTRAPSTKRKKVKK

Sequence 15 (SEQ ID NO: 15):
ATGGTGCTGATCCTGTGCTGCACCCTGGCCATCCTGTTCTGCGTGGCCGACGTGAACGTGTTCCAC

ATCTTCCTGCAGATGAGCGTGTGGAGGCCCAGCGAGGCCACCGTGTACCTGCCCCCCGTGCCCGT

GAGCAAGGTGGTGAGCACCGACGAGTACGTGAGCAGGACCAGCATCTACTACTACGCCGGCAGC

AGCAGGCTGCTGGCCGTGGGCAACCCCTACTTCAGCATCAAGAGCCCCAACAACAACAAGAAGG

TGCTGGTGCCCAAGGTGAGCGGCCTGCAGTACAGGGTGTTCAGGGTGAGGCTGCCCGACCCCAA

CAAGTTCGGCTTCCCCGACACCAGCTTCTACAACCCCGACACCCAGAGGCTGGTGTGGGCCTGCG

TGGGCCTGGAGATCGGCAGGGGCCAGCCCCTGGGCGTGGGCGTGAGCGGCCACCCCTACCTGAA

CAAGTTCGACGACACCGAGACCAGCAACAGGTACCCCGCCCAGCCCGGCAGCGACAACAGGGAG

TGCCTGAGCATGGACTACAAGCAGACCCAGCTGTGCCTGATCGGCTGCAAGCCCCCCACCGGCG

AGCACTGGGGCAAGGGCGTGGCCTGCAACAACAACGCCGCCGCCACCGACTGCCCCCCCCTGGA

GCTGTTCAACAGCATCATCGAGGACGGCGACATGGTGGACACCGGCTTCGGCTGCATGGACTTCG

GCACCCTGCAGGCCAACAAGAGCGACGTGCCCATCGACATCTGCAACAGCACCTGCAAGTACCC

CGACTACCTGAAGATGGCCAGCGAGCCCTACGGCGACAGCCTGTTCTTCTTCCTGAGGAGGGAGC

AGATGTTCGTGAGGCACTTCTTCAACAGGGCCGGCAAGCTGGGCGAGGCCGTGCCCGACGACCT

GTACATCAAGGGCAGCGGCAACACCGCCGTGATCCAGAGCAGCGCCTTCTTCCCCACCCCCAGCG

GCAGCATCGTGACCAGCGAGAGCCAGCTGTTCAACAAGCCCTACTGGCTGCAGAGGGCCCAGGG

CCACAACAACGGCATCTGCTGGGGCAACCAGCTGTTCGTGACCGTGGTGGACACCACCAGGAGC

ACCAACATGACCCTGTGCACCGAGGTGACCAAGGAGGGCACCTACAAGAACGACAACTTCAAGG

AGTACGTGAGGCACGTGGAGGAGTACGACCTGCAGTTCGTGTTCCAGCTGTGCAAGATCACCCTG

ACCGCCGAGATCATGACCTACATCCACACCATGGACAGCAACATCCTGGAGGACTGGCAGTTCG

GCCTGACCCCCCCCCCCAGCGCCAGCCTGCAGGACACCTACAGGTTCGTGACCAGCCAGGCCATC

ACCTGCCAGAAGACCGCCCCCCCCAAGGAGAAGGAGGACCCCCTGAACAAGTACACCTTCTGGG

AGGTGAACCTGAAGGAGAAGTTCAGCGCCGACCTGGACCAGTTCCCCCTGGGCAGGAAGTTCCT

GCTGCAGAGCGGCCTGAAGGCCAAGCCCAGGCTGAAGAGGAGCGCCCCCACCACCAGGGCCCCC

AGCACCAAGAGGAAGAAGGTGAAGAAGTGA

Sequence 16 (SEQ ID NO: 16):
ATGAGCGTGTGGAGGCCCAGCGAGGCCACCGTGTACCTGCCCCCCGTGCCCGTGAGCAAGGTGG

TGAGCACCGACGAGTACGTGAGCAGGACCAGCATCTACTACTACGCCGGCAGCAGCAGGCTGCT

GGCCGTGGGCCACCCCTACTTCAGCATCAAGAACCCCACCAACGCCAAGAAGCTGCTGGTGCCC

AAGGTGAGCGGCCTGCAGTACAGGGTGTTCAGGGTGAGGCTGCCCGACCCCAACAAGTTCGGCT

TCCCCGACACCAGCTTCTACAACCCCGACACCCAGAGGCTGGTGTGGGCCTGCGTGGGCCTGGAG

ATCGGCAGGGGCCAGCCCCTGGGCGTGGGCATCAGCGGCCACCCCCTGCTGAACAAGTTCGACG

ACACCGAGACCGGCAACAAGTACCCCGGCCAGCCCGGCGCCGACAACAGGGAGTGCCTGAGCAT

GGACTACAAGCAGACCCAGCTGTGCCTGCTGGGCTGCAAGCCCCCCACCGGCGAGCACTGGGGC

AAGGGCGTGGCCTGCACCAACGCCGCCCCCGCCAACGACTGCCCCCCCCTGGAGCTGATCAACA

CCATCATCGAGGACGGCGACATGGTGGACACCGGCTTCGGCTGCATGGACTTCAAGACCCTGCA

GGCCAACAAGAGCGACGTGCCCATCGACATCTGCGGCAGCACCTGCAAGTACCCCGACTACCTG

AAGATGACCAGCGAGCCCTACGGCGACAGCCTGTTCTTCTTCCTGAGGAGGGAGCAGATGTTCGT

GAGGCACTTCTTCAACAGGGCCGGCACCCTGGGCGAGGCCGTGCCCGACGACCTGTACATCAAG

GGCAGCGGCACCACCGCCAGCATCCAGAGCAGCGCCTTCTTCCCCACCCCCAGCGGCAGCATGGT

GACCAGCGAGAGCCAGCTGTTCAACAAGCCCTACTGGCTGCAGAGGGCCCAGGGCCACAACAAC

GGCATCTGCTGGGGCAACCAGGTGTTCGTGACCGTGGTGGACACCACCAGGAGCACCAACATGA

CCCTGTGCACCCAGGTGACCAGCGACAGCACCTACAAGAACGAGAACTTCAAGGAGTACATCAG

GCACGTGGAGGAGTACGACCTGrCAGTTCGTGTTCCAGCTGTGCAAGGTGACCCTGACCGCCGAG

GTGATGACCTACATCCACGCCATGAACCCCGACATCCTGGAGGACTGGCAGTTCGGCCTGACCCC

CCCCCCCAGCGCCAGCCTGCAGGACACCTACAGGTTCGTGACCAGCCAGGCCATCACCTGCCAGA

AGACCGTGCCCCCCAAGGAGAAGGAGGACCCCCTGGGCAAGTACACCTTCTGGGAGGTGGACCT

GAAGGAGAAGTTCAGCGCCGACCTGGACCAGTTCCCCCTGGGCAGGAAGTTCCTGCTGCAGGCC

GGCCTGAAGGCCAAGCCCAAGCTGAAGAGGGCCGCCCCCACCAGCACCAGGACCAGCAGCGCCA

AGAGGAAGAAGGTGAAGAAGTGA

Sequence 17 (SEQ ID NO: 17):
ATGGTGCAGATCCTGTTCTACATCCTGGTGATCTTCTACTACGTGGCCGGCGTGAACGTGTTCCAC

ATCTTCCTGCAGATGAGCGTGTGGAGGCCCAGCGAGGCCACCGTGTACCTGCCCCCCGTGCCCGT

GAGCAAGGTGGTGAGCACCGACGAGTACGTGAGCAGGACCAGCATCTACTACTACGCCGGCAGC

-continued
AGCAGGCTGCTGACCGTGGGCCACCCCTACTTCAGCATCAAGAACACCAGCAGCGGCAACGGCA

AGAAGGTGCTGGTGCCCAAGGTGAGCGGCCTGCAGTACAGGGTGTTCAGGATCAAGCTGCCCGA

CCCCAACAAGTTCGGCTTCCCCGACACCAGCTTCTACAACCCCGAGACCCAGAGGCTGGTGTGGG

CCTGCACCGGCCTGGAGATCGGCAGGGGCCAGCCCCTGGGCGTGGGCATCAGCGGCCACCCCCT

GCTGAACAAGTTCGACGACACCGAGACCAGCAACAAGTACGCCGGCAAGCCCGGCATCGACAAC

AGGGAGTGCCTGAGCATGGACTACAAGCAGACCCAGCTGTGCATCCTGGGCTGCAAGCCCCCCA

TCGGCGAGCACTGGGGCAAGGGCACCCCCTGCAACAACAACAGCGGCAACCCCGGCGACTGCCC

CCCCCTGCAGCTGATCAACAGCGTGATCCAGGACGGCGACATGGTGGACACCGGCTTCGGCTGC

ATGGACTTCAACACCCTGCAGGCCAGCAAGAGCGACGTGCCCATCGACATCTGCAGCAGCGTGT

GCAAGTACCCCGACTACCTGCAGATGGCCAGCGAGCCCTACGGCGACAGCCTGTTCTTCTTCCTG

AGGAGGGAGCAGATGTTCGTGAGGCACTTCTTCAACAGGGCCGGCACCCTGGGCGACCCCGTGC

CCGGCGACCTGTACATCCAGGGCAGCAACAGCGGCAACACCGCCACCGTGCAGAGCAGCGCCTT

CTTCCCCACCCCCAGCGGCAGCATGGTGACCAGCGAGAGCCAGCTGTTCAACAAGCCCTACTGGC

TGCAGAGGGCCCAGGGCCACAACAACGGCATCTGCTGGGGCAACCAGCTGTTCGTGACCGTGGT

GGACACCACCAGGAGCACCAACATGACCCTGTGCGCCGAGGTGAAGAAGGAGAGCACCTACAA

GAACGAGAACTTCAAGGAGTACCTGAGGCACGGCGAGGAGTTCGACCTGCAGTTCATCTTCCAG

CTGTGCAAGATCACCCTGACCGCCGACGTGATGACCTACATCCACAAGATGGACGCCACCATCCT

GGAGGACTGGCAGTTCGGCCTGACCCCCCCCCCCAGCGCCAGCCTGGAGGACACCTACAGGTTC

GTGACCAGCACCGCCATCACCTGCCAGAAGAACACCCCCCCCAAGGGCAAGGAGGACCCCCTGA

AGGACTACATGTTCTGGGAGGTGGACCTGAAGGAGAAGTTCAGCGCCGACCTGGACCAGTTCCC

CCTGGGCAGGAAGTTCCTGCTGCAGGCCGGCCTGCAGGCCAGGCCCAAGCTGAAGAGGCCCGCC

AGCAGCGCCCCCAGGACCAGCACCAAGAAGAAGAAGGTGAAGAGGTGA

Sequence 18 (SEQ ID NO: 18):
ATGACCGTGTACCTGCCCCCCGTGCCCGTGAGCAAGGTGGTGAGCACCGACGAGTACGTGAGCA

GGACCAGCATCTACTACTACGCCGGCAGCAGCAGGCTGCTGGCCGTGGGCAACCCCTACTTCAGC

ATCAAGAATCCCACTAACGCTAAAAAATTACTGGTGCCCAAGGTGAGCGGCCTGCAGTACAGGG

TGTTCAGGGTGAGGCTGCCCGACCCCAACAAGTTCGGCTTCCCCGACACCAGCTTCTACAACCCC

GACACCCAGAGGCTGGTGTGGGCCTGCGTGGGCCTGGAGATCGGCAGGGGCCAGCCCCTGGGCG

TGGGCGTGAGCGGCCACCCCCTACCTGAACAAGTTCGACGACACCGAGACCAGCAACAGGTACCC

CGCCCAGCCCGGCAGCGACAACAGGGAGTGCCTGAGCATGGACTACAAGCAGACCCAGCTGTGC

CTGATCGGCTGCAAGCCCCCCACCGGCGAGCACTGGGGCAAGGGCGTGGCCTGCAACAACAACG

CCGCCGCCACCGACTGCCCCCCCCTGGAGCTGTTCAACAGCATCATCGAGGACGGCGACATGGTG

GACACCGGCTTCGGCTGCATGGACTTCGGCACCCTGCAGGCCAACAAGAGCGACGTGCCCATCG

ACATCTGCAACAGCACCTGCAAGTACCCCGACTACCTGAAGATGGCCAGCGAGCCCTACGGCGA

CAGCCTGTTCTTCTTCCTGAGGAGGGAGCAGATGTTCGTGAGGCACTTCTTCAACAGGGCCGGCA

AGCTGGGCGAGGCCGTGCCCGACGACCTGTACATCAAGGGCAGCGGCAACACCGCCGTGATCCA

GAGCAGCGCCTTCTTCCCCACCCCCAGCGGCAGCATCGTGACCAGCGAGAGCCAGCTGTTCAACA

AGCCCTACTGGCTGCAGAGGGCCCAGGGCCACAACAACGGCATCTGCTGGGGCAACCAGCTGTT

CGTGACCGTGGTGGACACCACCAGGAGCACCAACATGACCCTGTGCACCGAGGTGACCAAGGAG

GGCACCTACAAGAACGACAACTTCAAGGAGTACGTGAGGCACGTGGAGGAGTACGACCTGCAGT

TCGTGTTCCAGCTGTGCAAGATCACCCTGACCGCCGAGATCATGACCTACATCCACACCATGGAC

-continued
```
AGCAACATCCTGGAGGACTGGCAGTTCGGCCTGACCCCCCCCCCAGCGCCAGCCTGCAGGACA

CCTACAGGTTCGTGACCAGCCAGGCCATCACCTGCCAGAAGACCGCCCCCCCCAAGGAGAAGGA

GGACCCCCTGAACAAGTACACCTTCTGGGAGGTGAACCTGAAGGAGAAGTTCAGCGCCGACCTG

GACCAGTTCCCCCTGGGCAGGAAGTTCCTGCTGCAGAGCGGCCTGAAGGCCAAGCCCAGGCTGA

AGAGGAGCGCCCCCACCACCAGGGCCCCCAGCACCAAGAGGAAGAAGGTGAAGAAGTAA
```
Sequence 19 (SEQ ID NO: 19):
```
ATGACCGTGTACCTGCCCCCCGTGCCCGTGAGCAAGGTGGTGAGCACCGACGAGTACGTGAGCA

GGACCAGCATCTACTACTACGCCGGCAGCAGCAGGCTGCTGGCCGTGGGCAACCCCTACTTCAGC

ATCAAGAGCCCCAACAACAACAAGAAGGTGCTGGTGCCCAAGGTGAGCGGCCTGCAGTACAGGG

TGTTCAGGGTGAGGCTGCCCGACCCCAACAAGTTCGGCTTCCCCGACACCAGCTTCTACAACCCC

GACACCCAGAGGCTGGTGTGGGCCTGCGTGGGCCTGGAGATCGGCAGGGGCCAGCCCCTGGGCG

TCGGAATAAGCGGCCACCCCTTACTGAACAAGTTCGACGACACCGAGACCAGCAACAGGTACCC

CGCCCAGCCCGGCAGCGACAACAGGGAGTGCCTGAGCATGGACTACAAGCAGACCCAGCTGTGC

CTGATCGGCTGCAAGCCCCCCACCGGCGAGCACTGGGGCAAGGGCGTGGCCTGCAACAACAACG

CCGCCGCCACCGACTGCCCCCCCCTGGAGCTGTTCAACAGCATCATCGAGGACGGCGACATGGTG

GACACCGGCTTCGGCTGCATGGACTTCGGCACCCTGCAGGCCAACAAGAGCGACGTGCCCATCG

ACATCTGCAACAGCACCTGCAAGTACCCCGACTACCTGAAGATGGCCAGCGAGCCCTACGGCGA

CAGCCTGTTCTTCTTCCTGAGGAGGGAGCAGATGTTCGTGAGGCACTTCTTCAACAGGGCCGGCA

AGCTGGGCGAGGCCGTGCCCGACGACCTGTACATCAAGGGCAGCGGCAACACCGCCGTGATCCA

GAGCAGCGCCTTCTTCCCCACCCCCAGCGGCAGCATCGTGACCAGCGAGAGCCAGCTGTTCAACA

AGCCCTACTGGCTGCAGAGGGCCCAGGGCCACAACAACGGCATCTGCTGGGGCAACCAGCTGTT

CGTGACCGTGGTGGACACCACCAGGAGCACCAACATGACCCTGTGCACCGAGGTGACCAAGGAG

GGCACCTACAAGAACGACAACTTCAAGGAGTACGTGAGGCACGTGGAGGAGTACGACCTGCAGT

TCGTGTTCCAGCTGTGCAAGATCACCCTGACCGCCGAGATCATGACCTACATCCACACCATGGAC

AGCAACATCCTGGAGGACTGGCAGTTCGGCCTGACCCCCCCCCCAGCGCCAGCCTGCAGGACA

CCTACAGGTTCGTGACCAGCCAGGCCATCACCTGCCAGAAGACCGCCCCCCCCAAGGAGAAGGA

GGACCCCCTGAACAAGTACACCTTCTGGGAGGTGAACCTGAAGGAGAAGTTCAGCGCCGACCTG

GACCAGTTCCCCCTGGGCAGGAAGTTCCTGCTGCAGAGCGGCCTGAAGGCCAAGCCCAGGCTGA

AGAGGAGCGCCCCCACCACCAGGGCCCCCAGCACCAAGAGGAAGAAGGTGAAGAAGTGA
```
Sequence 20 (SEQ ID NO: 20):
```
ATGACCGTGTACCTGCCCCCCGTGCCCGTGAGCAAGGTGGTGAGCACCGACGAGTACGTGAGCA

GGACCAGCATCTACTACTACGCCGGCAGCAGCAGGCTGCTGGCCGTGGGCAACCCCTACTTCAGC

ATCAAGAGCCCCAACAACAACAAGAAGGTGCTGGTGCCCAAGGTGAGCGGCCTGCAGTACAGGG

TGTTCAGGGTGAGGCTGCCCGACCCCAACAAGTTCGGCTTCCCCGACACCAGCTTCTACAACCCC

GACACCCAGAGGCTGGTGTGGGCCTGCGTGGGCCTGGAGATCGGCAGGGGCCAGCCCCTGGGCG

TCGGAATAAGCGGCCACCCCTTACTGAACAAGTTCGACGACACCGAGACCGGAAACAAGTACCC

CGCCCAGCCCGGCAGCGACAACAGGGAGTGCCTGAGCATGGACTACAAGCAGACCCAGCTGTGC

CTGATCGGCTGCAAGCCCCCCACCGGCGAGCACTGGGGCAAGGGCGTGGCCTGCAACAACAACG

CCGCCGCCACCGACTGCCCCCCCCTGGAGCTGTTCAACAGCATCATCGAGGACGGCGACATGGTG

GACACCGGCTTCGGCTGCATGGACTTCGGCACCCTGCAGGCCAACAAGAGCGACGTGCCCATCG

ACATCTGCAACAGCACCTGCAAGTACCCCGACTACCTGAAGATGGCCAGCGAGCCCTACGGCGA

CAGCCTGTTCTTCTTCCTGAGGAGGGAGCAGATGTTCGTGAGGCACTTCTTCAACAGGGCCGGCA
```

AGCTGGGCGAGGCCGTGCCCGACGACCTGTACATCAAGGGCAGCGGCAACACCGCCGTGATCCA

GAGCAGCGCCTTCTTCCCCACCCCCAGCGGCAGCATCGTGACCAGCGAGAGCCAGCTGTTCAACA

AGCCCTACTGGCTGCAGAGGGCCCAGGGCCACAACAACGGCATCTGCTGGGGCAACCAGCTGTT

CGTGACCGTGGTGGACACCACCAGGAGCACCAACATGACCCTGTGCACCGAGGTGACCAAGGAG

GGCACCTACAAGAACGACAACTTCAAGGAGTACGTGAGGCACGTGGAGGAGTACGACCTGCAGT

TCGTGTTCCAGCTGTGCAAGATCACCCTGACCGCCGAGATCATGACCTACATCCACACCATGGAC

AGCAACATCCTGGAGGACTGGCAGTTCGGCCTGACCCCCCCCCCAGCGCCAGCCTGCAGGACA

CCTACAGGTTCGTGACCAGCCAGGCCATCACCTGCCAGAAGACCGCCCCCCCCAAGGAGAAGGA

GGACCCCCTGAACAAGTACACCTTCTGGGAGGTGAACCTGAAGGAGAAGTTCAGCGCCGACCTG

GACCAGTTCCCCCTGGGCAGGAAGTTCCTGCTGCAGAGCGGCCTGAAGGCCAAGCCCAGGCTGA

AGAGGAGCGCCCCCACCACCAGGGCCCCCAGCACCAAGAGGAAGAAGGTGAAGAAGTGA

Sequence 21 (SEQ ID NO: 21):
ATGACCGTGTACCTGCCCCCCGTGCCCGTGAGCAAGGTGGTGAGCACCGACGAGTACGTGAGCA

GGACCAGCATCTACTACTACGCCGGCAGCAGCAGGCTGCTGGCCGTGGGCAACCCCTACTTCAGC

ATCAAGAGCCCCAACAACAACAAGAAGGTGCTGGTGCCCAAGGTGAGCGGCCTGCAGTACAGGG

TGTTCAGGGTGAGGCTGCCCGACCCCAACAAGTTCGGCTTCCCCGACACCAGCTTCTACAACCCC

GACACCCAGAGGCTGGTGTGGGCCTGCGTGGGCCTGGAGATCGGCAGGGGCCAGCCCCTGGGCG

TCGGAATAAGCGGCCACCCCTTACTGAACAAGTTCGACGACACCGAGACCGGAAACAAGTACCC

CGGACAGCCCGGCGCTGACAACAGGGAGTGCCTGAGCATGGACTACAAGCAGACCCAGCTGTGC

CTGATCGGCTGCAAGCCCCCCACCGGCGAGCACTGGGGCAAGGGCGTGGCCTGCAACAACAACG

CCGCCGCCACCGACTGCCCCCCCCTGGAGCTGTTCAACAGCATCATCGAGGACGGCGACATGGTG

GACACCGGCTTCGGCTGCATGGACTTCGGCACCCTGCAGGCCAACAAGAGCGACGTGCCCATCG

ACATCTGCAACAGCACCTGCAAGTACCCCGACTACCTGAAGATGGCCAGCGAGCCCTACGGCGA

CAGCCTGTTCTTCTTCCTGAGGAGGGAGCAGATGTTCGTGAGGCACTTCTTCAACAGGGCCGGCA

AGCTGGGCGAGGCCGTGCCCGACGACCTGTACATCAAGGGCAGCGGCAACACCGCCGTGATCCA

GAGCAGCGCCTTCTTCCCCACCCCCAGCGGCAGCATCGTGACCAGCGAGAGCCAGCTGTTCAACA

AGCCCTACTGGCTGCAGAGGGCCCAGGGCCACAACAACGGCATCTGCTGGGGCAACCAGCTGTT

CGTGACCGTGGTGGACACCACCAGGAGCACCAACATGACCCTGTGCACCGAGGTGACCAAGGAG

GGCACCTACAAGAACGACAACTTCAAGGAGTACGTGAGGCACGTGGAGGAGTACGACCTGCAGT

TCGTGTTCCAGCTGTGCAAGATCACCCTGACCGCCGAGATCATGACCTACATCCACACCATGGAC

AGCAACATCCTGGAGGACTGGCAGTTCGGCCTGACCCCCCCCCCAGCGCCAGCCTGCAGGACA

CCTACAGGTTCGTGACCAGCCAGGCCATCACCTGCCAGAAGACCGCCCCCCCCAAGGAGAAGGA

GGACCCCCTGAACAAGTACACCTTCTGGGAGGTGAACCTGAAGGAGAAGTTCAGCGCCGACCTG

GACCAGTTCCCCCTGGGCAGGAAGTTCCTGCTGCAGAGCGGCCTGAAGGCCAAGCCCAGGCTGA

AGAGGAGCGCCCCCACCACCAGGGCCCCCAGCACCAAGAGGAAGAAGGTGAAGAAGTAA

Sequence 22 (SEQ ID NO: 22):
ATGACCGTGTACCTGCCCCCCGTGCCCGTGAGCAAGGTGGTGAGCACCGACGAGTACGTGAGCA

GGACCAGCATCTACTACTACGCCGGTAGCAGCAGGCTGCTGGCCGTGGGCAACCCCTACTTCAGC

ATCAAGAGCCCCAACAACAACAAGAAGGTGCTGGTGCCCAAGGTGAGCGGCCTGCAGTACAGGG

TGTTCAGGGTGAGGCTGCCCGACCCCAACAAGTTCGGCTTCCCCGACACCAGCTTCTACAACCCC

GACACCCAGAGGCTGGTGTGGGCCTGCGTGGGCCTGGAGATCGGCAGGGGCCAGCCCCTGGGCG

-continued
```
TGGGCGTGAGCGGCCACCCCTACCTGAACAAGTTCGACGACACCGAGACCAGCAACAGGTACCC

CGCCCAGCCCGGCAGCGACAACAGGGAGTGCCTGAGCATGGACTACAAGCAGACCCAGCTGTGC

CTGATCGGCTGCAAGCCCCCCACCGGCGAGCACTGGGGCAAGGGAGTAGCATGTACAAACGCTG

CACCTGCCAACGACTGCCCCCCCCTGGAGCTGTTCAACAGCATCATCGAGGACGGCGACATGGTG

GACACCGGCTTCGGCTGCATGGACTTCGGCACCCTGCAGGCCAACAAGAGCGACGTGCCCATCG

ACATCTGCAACAGCACCTGCAAGTACCCCGACTACCTGAAGATGGCCAGCGAGCCCTACGGCGA

CAGCCTGTTCTTCTTCCTGAGGAGGGAGCAGATGTTCGTGAGGCACTTCTTCAACAGGGCCGGCA

AGCTGGGCGAGGCCGTGCCCGACGACCTGTACATCAAGGGCAGCGGCAACACCGCCGTGATCCA

GAGCAGCGCCTTCTTCCCCACCCCCAGCGGCAGCATCGTGACCAGCGAGAGCCAGCTGTTCAACA

AGCCCTACTGGCTGCAGAGGGCCCAGGGCCACAACAACGGCATCTGCTGGGGCAACCAGCTGTT

CGTGACCGTGGTGGACACCACCAGGAGCACCAACATGACCCTGTGCACCGAGGTGACCAAGGAG

GGCACCTACAAGAACGACAACTTCAAGGAGTACGTGAGGCACGTGGAGGAGTACGACCTGCAGT

TCGTGTTCCAGCTGTGCAAGATCACCCTGACCGCCGAGATCATGACCTACATCCACACCATGGAC

AGCAACATCCTGGAGGACTGGCAGTTCGGCCTGACCCCCCCCCCAGCGCCAGCCTGCAGGACA

CCTACAGGTTCGTGACCAGCCAGGCCATCACCTGCCAGAAGACCGCCCCCCCCAAGGAGAAGGA

GGACCCCCTGAACAAGTACACCTTCTGGGAGGTGAACCTGAAGGAGAAGTTCAGCGCCGACCTG

GACCAGTTCCCCCTGGGCAGGAAGTTCCTGCTGCAGAGCGGCCTGAAGGCCAAGCCCAGGCTGA

AGAGGAGCGCCCCCACCACCAGGGCCCCCAGCACCAAGAGGAAGAAGGTGAAGAAGTAA

Sequence 23 (SEQ ID NO: 23):
ATGACCGTGTACCTGCCCCCCGTGCCCGTGAGCAAGGTGGTGAGCACCGACGAGTACGTGAGCA

GGACCAGCATCTACTACTACGCCGGCAGCAGCAGGCTGCTGGCCGTGGGCAACCCCTACTTCAGC

ATCAAGAGCCCCAACAACAACAAGAAGGTGCTGGTGCCCAAGGTGAGCGGCCTGCAGTACAGGG

TGTTCAGGGTGAGGCTGCCCGACCCCAACAAGTTCGGCTTCCCCGACACCAGCTTCTACAACCCC

GACACCCAGAGGCTGGTGTGGGCCTGCGTGGGCCTGGAGATCGGCAGGGGCCAGCCCCTGGGCG

TGGGCGTGAGCGGCCACCCCTACCTGAACAAGTTCGACGACACCGAGACCAGCAACAGGTACCC

CGCCCAGCCCGGCAGCGACAACAGGGAGTGCCTGAGCATGGACTACAAGCAGACCCAGCTGTGC

CTGATCGGCTGCAAGCCCCCCACCGGCGAGCACTGGGGCAAGGGCGTGGCCTGCAACAACAACG

CCGCCGCCACCGACTGCCCCCCCCTGGAGCTGTTCAACAGCATCATCGAGGACGGCGACATGGTG

GACACCGGCTTCGGCTGCATGGACTTCGGCACCCTGCAGGCCAACAAGAGCGACGTGCCCATCG

ACATCTGCAACAGCACCTGCAAGTACCCCGACTACCTGAAGATGGCCAGCGAGCCCTACGGCGA

CAGCCTGTTCTTCTTCCTGAGGAGGGAGCAGATGTTCGTGAGGCACTTCTTCAACAGGGCCGGCA

AGCTGGGCGAGGCCGTGCCCGACGACCTGTACATCAAGGGCAGCGGCACAACAGCAAGTATCCA

GAGCAGCGCCTTCTTCCCCACCCCCAGCGGCAGCATCGTGACCAGCGAGAGCCAGCTGTTCAACA

AGCCCTACTGGCTGCAGAGGGCCCAGGGCCACAACAACGGCATCTGCTGGGGCAACCAGCTGTT

CGTGACCGTGGTGGACACCACCAGGAGCACCAACATGACCCTGTGCACCGAGGTGACCAAGGAG

GGCACCTACAAGAACGACAACTTCAAGGAGTACGTGAGGCACGTGGAGGAGTACGACCTGCAGT

TCGTGTTCCAGTTGTGCAAGATCACCCTGACCGCCGAGATCATGACCTACATCCACACCATGGAC

AGCAACATCCTGGAGGACTGGCAGTTCGGCCTGACCCCCCCCCCAGCGCCAGCCTGCAGGACA

CCTACAGGTTCGTGACCAGCCAGGCCATCACCTGCCAGAAGACCGCCCCCCCCAAGGAGAAGGA

GGACCCCCTGAACAAGTACACCTTCTGGGAGGTGAACCTGAAGGAGAAGTTCAGCGCCGACCTG
```

-continued

GACCAGTTCCCCCTGGGCAGGAAGTTCCTGCTGCAGAGCGGCCTGAAGGCCAAGCCCAGGCTGA

AGAGGAGCGCCCCCACCACCAGGGCCCCCAGCACCAAGAGGAAGAAGGTGAAGAAGTAA

Sequence 24 (SEQ ID NO: 24):
ATGACCGTGTACCTGCCCCCCGTGCCCGTGAGCAAGGTGGTGAGCACCGACGAGTACGTGAGCA

GGACCAGCATCTACTACTACGCCGGCAGCAGCAGGCTGCTGGCCGTGGGCAACCCCTACTTCAGC

ATCAAGAGCCCCAACAACAACAAGAAGGTGCTGGTGCCCAAGGTGAGCGGCCTGCAGTACAGGG

TGTTCAGGGTGAGGCTGCCCGACCCCAACAAGTTCGGCTTCCCCGACACCAGCTTCTACAACCCC

GACACCCAGAGGCTGGTGTGGGCCTGCGTGGGCCTGGAGATCGGCAGGGGCCAGCCCCTGGGCG

TGGGCGTGAGCGGCCACCCCTACCTGAACAAGTTCGACGACACCGAGACCAGCAACAGGTACCC

CGCCCAGCCCGGCAGCGACAACAGGGAGTGCCTGAGCATGGACTACAAGCAGACCCAGCTGTGC

CTGATCGGCTGCAAGCCCCCCACCGGCGAGCACTGGGGCAAGGGCGTGGCCTGCAACAACAACG

CCGCCGCCACCGACTGCCCCCCCCTGGAGCTGTTCAACAGCATCATCGAGGACGGCGACATGGTG

GACACCGGCTTCGGCTGCATGGACTTCGGCACCCTGCAGGCCAACAAGAGCGACGTGCCCATCG

ACATCTGCAACAGCACCTGCAAGTACCCCGACTACCTGAAGATGGCCAGCGAGCCCTACGGCGA

CAGCCTGTTCTTCTTCCTGAGGAGGGAGCAGATGTTCGTGAGGCACTTCTTCAACAGGGCCGGCA

AGCTGGGCGAGGCCGTGCCCGACGACCTGTACATCAAGGGCAGCGGCAACACCGCCGTGATCCA

GAGCAGCGCCTTCTTCCCCACCCCCAGCGGCAGCATCGTGACCAGCGAGAGCCAGCTGTTCAACA

AGCCCTACTGGCTGCAGAGGGCCCAGGGCCACAACAACGGCATCTGCTGGGGCAACCAGCTGTT

CGTGACCGTGGTGGACACCACCAGGAGCACCAACATGACCCTGTGCACCGAGGTGACCAGCGAC

AGCACGTACAAGAACGAGAACTTCAAGGAGTACGTGAGGCACGTGGAGGAGTACGACCTGCAGT

TCGTGTTCCAGCTGTGCAAGATCACCCTGACCGCCGAGATCATGACCTACATCCACACCATGGAC

AGCAACATCCTGGAGGACTGGCAGTTCGGCCTGACCCCCCCCCCAGCGCCAGCCTGCAGGACA

CCTACAGGTTCGTGACCAGCCAGGCCATCACCTGCCAGAAGACCGCCCCCCCCAAGGAGAAGGA

GGACCCCCTGAACAAGTACACCTTCTGGGAGGTGAACCTGAAGGAGAAGTTCAGCGCCGACCTG

GACCAGTTCCCCCTGGGCAGGAAGTTCCTGCTGCAGAGCGGCCTGAAGGCCAAGCCCAGGCTGA

AGAGGAGCGCCCCCACCACCAGGGCCCCCAGCACCAAGAGGAAGAAGGTGAAGAAGTAA

Sequence 25 (SEQ ID NO: 25):
ATGACCGTGTACCTGCCCCCCGTGCCCGTGAGCAAGGTGGTGAGCACCGACGAGTACGTGAGCA

GGACCAGCATCTACTACTACGCCGGCAGCAGCAGGCTGCTGGCCGTGGGCAACCCCTACTTCAGC

ATCAAGAATCCCACTAACGCTAAAAAATTACTGGTGCCCAAGGTGAGCGGCCTGCAGTACAGGG

TGTTCAGGGTGAGGCTGCCCGACCCCAACAAGTTCGGCTTCCCCGACACCAGCTTCTACAACCCC

GACACCCAGAGGCTGGTGTGGGCCTGCGTGGGCCTGGAGATCGGCAGGGGCCAGCCCCTGGGCG

TGGGCATCAGCGGCCACCCCCTGCTGAACAAGTTCGACGACACCGAGACCAGCAACAAGTACGC

CGGCAAGCCCGGCATCGACAACAGGGAGTGCCTGAGCATGGACTACAAGCAGACCCAGCTGTGC

CTGATCGGCTGCAAGCCCCCCACCGGCGAGCACTGGGGCAAGGGCGTGGCCTGCAACAACAACG

CCGCCGCCACCGACTGCCCCCCCCTGGAGCTGTTCAACAGCATCATCGAGGACGGCGACATGGTG

GACACCGGCTTCGGCTGCATGGACTTCGGCACCCTGCAGGCCAACAAGAGCGACGTGCCCATCG

ACATCTGCAACAGCACCTGCAAGTACCCCGACTACCTGAAGATGGCCAGCGAGCCCTACGGCGA

CAGCCTGTTCTTCTTCCTGAGGAGGGAGCAGATGTTCGTGAGGCACTTCTTCAACAGGGCCGGCA

AGCTGGGCGAGGCCGTGCCCGACGACCTGTACATCAAGGGCAGCGGCAACACCGCCGTGATCCA

GAGCAGCGCCTTCTTCCCCACCCCCAGCGGCAGCATCGTGACCAGCGAGAGCCAGCTG.TTCAACA

```
Sequence 26 (SEQ ID NO: 26):
AGCCCTACTGGCTGCAGAGGGCCCAGGGCCACAACAACGGCATCTGCTGGGGCAACCAGCTGTT

CGTGACCGTGGTGGACACCACCAGGAGCACCAACATGACCCTGTGCACCGAGGTGACCAAGGAG

GGCACCTACAAGAACGACAACTTCAAGGAGTACGTGAGGCACGTGGAGGAGTACGACCTGCAGT

TCGTGTTCCAGCTGTGCAAGATCACCCTGACCGCCGAGATCATGACCTACATCCACACCATGGAC

AGCAACATCCTGGAGGACTGGCAGTTCGGCCTGACCCCCCCCCCCAGCGCCAGCCTGCAGGACA

CCTACAGGTTCGTGACCAGCCAGGCCATCACCTGCCAGAAGACCGCCCCCCCCAAGGAGAAGGA

GGACCCCCTGAACAAGTACACCTTCTGGGAGGTGAACCTGAAGGAGAAGTTCAGCGCCGACCTG

GACCAGTTCCCCCTGGGCAGGAAGTTCCTGCTGCAGAGCGGCCTGAAGGCCAAGCCCAGGCTGA

AGAGGAGCGCCCCCACCACCAGGGCCCCCAGCACCAAGAGGAAGAAGGTGAAGAAGTAA
```

Sequence 26 (SEQ ID NO: 26):
```
ATGACCGTGTACCTGCCCCCCGTGCCCGTGAGCAAGGTGGTGAGCACCGACGAGTACGTGAGCA

GGACCAGCATCTACTACTACGCCGGCAGCAGCAGGCTGCTGGCCGTGGGCAACCCCTACTTCAGC

ATCAAGAATCCCACTAACGCTAAAAAATTACTGGTGCCCAAGGTGAGCGGCCTGCAGTACAGGG

TGTTCAGGGTGAGGCTGCCCGACCCCAACAAGTTCGGCTTCCCCGACACCAGCTTCTACAACCCC

GACACCCAGAGGCTGGTGTGGGCCTGCGTGGGCCTGGAGATCGGCAGGGGCCAGCCCCTGGGCG

TGGGCGTGAGCGGCCACCCCTACCTGAACAAGTTCGACGACACCGAGACCAGCAACAGGTACCC

CGCCCAGCCCGGCAGCGACAACAGGGAGTGCCTGAGCATGGACTACAAGCAGACCCAGCTGTGC

CTGATCGGCTGCAAGCCCCCCACCGGCGAGCACTGGGGCAAGGGCACCCCCTGCAACAACAACA

GCGGCAACCCCGGCGACTGCCCCCCCCTGGAGCTGTTCAACAGCATCATCGAGGACGGCGACAT

GGTGGACACCGGCTTCGGCTGCATGGACTTCGGCACCCTGCAGGCCAACAAGAGCGACGTGCCC

ATCGACATCTGCAACAGCACCTGCAAGTACCCCGACTACCTGAAGATGGCCAGCGAGCCCTACG

GCGACAGCCTGTTCTTCTTCCTGAGGAGGGAGCAGATGTTCGTGAGGCACTTCTTCAACAGGGCC

GGCAAGCTGGGCGAGGCCGTGCCCGACGACCTGTACATCAAGGGCAGCGGCAACACCGCCGTGA

TCCAGAGCAGCGCCTTCTTCCCCACCCCCAGCGGCAGCATCGTGACCAGCGAGAGCCAGCTGTTC

AACAAGCCCTACTGGCTGCAGAGGGCCCAGGGCCACAACAACGGCATCTGCTGGGGCAACCAGC

TGTTCGTGACCGTGGTGGACACCACCAGGAGCACCAACATGACCCTGTGCACCGAGGTGACCAA

GGAGGGCACCTACAAGAACGACAACTTCAAGGAGTACGTGAGGCACGTGGAGGAGTACGACCTG

CAGTTCGTGTTCCAGCTGTGCAAGATCACCCTGACCGCCGAGATCATGACCTACATCCACACCAT

GGACAGCAACATCCTGGAGGACTGGCAGTTCGGCCTGACCCCCCCCCCCAGCGCCAGCCTGCAG

GACACCTACAGGTTCGTGACCAGCCAGGCCATCACCTGCCAGAAGACCGCCCCCCCCAAGGAGA

AGGAGGACCCCCTGAACAAGTACACCTTCTGGGAGGTGAACCTGAAGGAGAAGTTCAGCGCCGA

CCTGGACCAGTTCCCCCTGGGCAGGAAGTTCCTGCTGCAGAGCGGCCTGAAGGCCAAGCCCAGG

CTGAAGAGGAGCGCCCCCACCACCAGGGCCCCCAGCACCAAGAGGAAGAAGGTGAAGAAGTAA
```

Sequence 27 (SEQ ID NO: 27):
```
ATGACCGTGTACCTGCCCCCCGTGCCCGTGAGCAAGGTGGTGAGCACCGACGAGTACGTGAGCA

GGACCAGCATCTACTACTACGCCGGCAGCAGCAGGCTGCTGGCCGTGGGCAACCCCTACTTCAGC

ATCAAGAATCCCACTAACGCTAAAAAATTACTGGTGCCCAAGGTGAGCGGCCTGCAGTACAGGG

TGTTCACrGGTGAGGCTGCCCGACCCCAACAAGTTCGGCTTCCCCGACACCAGCTTCTACAACCCC

GACACCCAGAGGCTGGTGTGGGCCTGCGTGGGCCTGGAGATCGGCAGGGGCCAGCCCCTGGGCG

TGGGCGTGAGCGGCCACCCCTACCTGAACAAGTTCGACGACACCGAGACCAGCAACAGGTACCC

CGCCCAGCCCGGCAGCGACAACAGGGAGTGCCTGAGCATGGACTACAAGCAGACCCAGCTGTGC

CTGATCGGCTGCAAGCCCCCCACCGGCGAGCACTGGGGCAAGGGCGTGGCCTGCAACAACAACG
```

-continued

CCGCCGCCACCGACTGCCCCCCCCTGGAGCTGTTCAACAGCATCATCGAGGACGGCGACATGGTG
GACACCGGCTTCGGCTGCATGGACTTCGGCACCCTGCAGGCCAACAAGAGCGACGTGCCCATCG
ACATCTGCAACAGCACCTGCAAGTACCCCGACTACCTGAAGATGGCCAGCGAGCCCTACGGCGA
CAGCCTGTTCTTCTTCCTGAGGAGGGAGCAGATGTTCGTGAGGCACTTCTTCAACAGGGCCGGCA
CCCTGGGCGACCCCGTGCCCGGCGACCTGTACATCCAGGGCAGCAACAGCGGCAACACCGCCAC
CGTGCAGAGCAGCGCCTTCTTCCCCACCCCCAGCGGCAGCATCGTGACCAGCGAGAGCCAGCTGT
TCAACAAGCCCTACTGGCTGCAGAGGGCCCAGGGCCACAACAACGGCATCTGCTGGGGCAACCA
GCTGTTCGTGACCGTGGTGGACACCACCAGGAGCACCAACATGACCCTGTGCACCGAGGTGACC
AAGGAGGGCACCTACAAGAACGACAACTTCAAGGAGTACGTGAGGCACGTGGAGGAGTACGAC
CTGCAGTTCGTGTTCCAGCTGTGCAAGATCACCCTGACCGCCGAGATCATGACCTACATCCACAC
CATGGACAGCAACATCCTGGAGGACTGGCAGTTCGGCCTGACCCCCCCCCCCAGCGCCAGCCTGC
AGGACACCTACAGGTTCGTGACCAGCCAGGCCATCACCTGCCAGAAGACCGCCCCCCCCAAGGA
GAAGGAGGACCCCCTGAACAAGTACACCTTCTGGGAGGTGAACCTGAAGGAGAAGTTCAGCGCC
GACCTGGACCAGTTCCCCCTGGGCAGGAAGTTCCTGCTGCAGAGCGGCCTGAAGGCCAAGCCCA
GGCTGAAGAGGAGCGCCCCCACCACCAGGGCCCCCAGCACCAAGAGGAAGAAGGTGAAGAAGT
AA

Sequence 28 (SEQ ID NO: 28):
ATGACCGTGTACCTGCCCCCCGTGCCCGTGAGCAAGGTGGTGAGCACCGACGAGTACGTGAGCA
GGACCAGCATCTACTACTACGCCGGCAGCAGCAGGCTGCTGGCCGTGGGCAACCCCTACTTCAGC
ATCAAGAATCCCACTAACGCTAAAAAATTACTGGTGCCCAAGGTGAGCGGCCTGCAGTACAGGG
TGTTCAGGGTGAGGCTGCCCGACCCCAACAAGTTCGGCTTCCCCGACACCAGCTTCTACAACCCC
GACACCCAGAGGCTGGTGTGGGCCTGCGTGGGCCTGGAGATCGGCAGGGCCAGCCCCTGGGCG
TGGGCGTGAGCGGCCACCCCTACCTGAACAAGTTCGACGACACCGAGACCAGCAACAGGTACCC
CGCCCAGCCCGGCAGCGACAACAGGGAGTGCCTGAGCATGGACTACAAGCAGACCCAGCTGTGC
CTGATCGGCTGCAAGCCCCCCACCGGCGAGCACTGGGGCAAGGGCGTGGCCTGCAACAACAACG
CCGCCGCCACCGACTGCCCCCCCCTGGAGCTGTTCAACAGCATCATCGAGGACGGCGACATGGTG
GACACCGGCTTCGGCTGCATGGACTTCGGCACCCTGCAGGCCAACAAGAGCGACGTGCCCATCG
ACATCTGCAACAGCACCTGCAAGTACCCCGACTACCTGAAGATGGCCAGCGAGCCCTACGGCGA
CAGCCTGTTCTTCTTCCTGAGGAGGGAGCAGATGTTCGTGAGGCACTTCTTCAACAGGGCCGGCA
AGCTGGGCGAGGCCGTGCCCGACGACCTGTACATCAAGGGCAGCGGCAACACCGCCGTGATCCA
GAGCAGCGCCTTCTTCCCCACCCCCAGCGGCAGCATCGTGACCAGCGAGAGCCAGCTGTTCAACA
AGCCCTACTGGCTGCAGAGGGCCCAGGGCCACAACAACGGCATCTGCTGGGGCAACCAGCTGTT
CGTGACCGTGGTGGACACCACCAGGAGCACCAACATGACCCTGTGCACCGAGGTGAAGAAGGAG
AGCACCTACAAGAACGAGAACTTCAAGGAGTACGTGAGGCACGTGGAGGAGTACGACCTGCAGT
TCGTGTTCCAGCTGTGCAAGATCACCCTGACCGCCGAGATCATGACCTACATCCACACCATGGAC
AGCAACATCCTGGAGGACTGGCAGTTCGGCCTGACCCCCCCCCCCAGCGCCAGCCTGCAGGACA
CCTACAGGTTCGTGACCAGCCAGGCCATCACCTGCCAGAAGACCGCCCCCCCCAAGGAGAAGGA
GGACCCCCTGAACAAGTACACCTTCTGGGAGGTGAACCTGAAGGAGAAGTTCAGCGCCGACCTG
GACCAGTTCCCCCTGGGCAGGAAGTTCCTGCTGCAGAGCGGCCTGAAGGCCAAGCCCAGGCTGA
AGAGGAGCGCCCCCACCACCAGGGCCCCCAGCACCAAGAGGAAGAAGGTGAAGAAGTAA -continued Sequence 59 (SEQ ID NO: 59):
NPTNAKKL Sequence 60 (SEQ ID NO: 60):
SDSTYKNE Sequence 61 (SEQ ID NO: 61):
ISGHPLLNKFDDTETSNKYAGKPGI Sequence 62 (SEQ ID NO: 62):
KKESTYKNE Specific Modes for Carrying Out the Invention The present invention is further described by reference to the examples as follows, wherein the examples are used only for the purpose of illustrating the present invention, rather than limiting the present invention.

Unless indicated otherwise, the molecular biological experimental methods and immunological assays used in the present invention are carried out substantially in accordance with the methods as described in Sambrook J et al., Molecular Cloning: A Laboratory Manual (Second Edition), Cold Spring Harbor Laboratory Press, 1989, and F. M. Ausubel et al., Short Protocols in Molecular Biology, 3rd Edition, John Wiley & Sons, Inc., 1995; and restriction enzymes are used under the conditions recommended by the manufacturers. Those skilled in the art understand that the examples are used for illustrating the present invention, but not intended to limit the protection scope of the present invention.

EXAMPLE 1. EXPRESSION AND PURIFICATION OF THE MUTATED HPV58 L1 PROTEINS

Construction of Expression Vectors

An expression vector encoding the mutated HPV58 L1 protein comprising a segment from HPV33 L1 protein was constructed by PCR for multi-site mutagenesis, wherein the initial template used was the plasmid pTO-T7-HPV58L1N35C (encoding the HPV58 L1 protein having 35 amino acids truncated at N-terminal; abbreviated as 58L1N35 in Table 2). The templates and primers for each PCR were shown in Table 2, and the amplification conditions for PCR were as followed: denaturation at 94° C. for 10 min; 25 cycles (denaturation at 94° C. for 50 sec, annealing at a given temperature for a certain period of time, and extension at 72° C. for 7.5 min); and final extension at 72° C. for 10 min. The sequences of the PCR primers used were listed in Table 3.

To the amplification product (50 μL), 2 μL restriction endonuclease DpnI was added, and the resultant mixture was incubated at 37° C. for 60 min. 10 μL of the product of digestion was used to transform 40 μL competent *E. coli* ER2566 (purchased from New England Biolabs) prepared by the Calcium chloride method. The transformed *E. coli* was spread onto solid LB medium (the components of the LB medium: 10 g/L peptone, 5 g/L yeast powder, 10 g/L NaCl, the same hereinafter) containing kanamycin (at a final concentration of 25 mg/mL, the same hereinafter), and was subjected to static culture at 37° C. for 10-12 h until single colonies could be observed clearly. Single colony was picked and inoculated into a tube containing 4 mL liquid LB medium (containing kanamycin), and cultured with shaking at 220 rpm for 10 h at 37° C., and then 1 ml bacterial solution was taken and stored at −70° C. Plasmids were extracted from *E. coli*, and T7 primer was used to sequence the nucleotide sequences of the fragments of interest inserted into the plasmids. The sequencing result showed that the nucleotide sequences of the fragments of interest inserted into the constructed plasmids (expression vectors) were SEQ ID NO: 18, 19, 20, 21, 22, 23, and 24, respectively, and their encoded amino acid sequences were SEQ ID NO: 4, 5, 6, 7, 8, 9, and 10, respectively (the corresponding proteins were designated as H58N35-33T1, H58N35-33T2-1, H58N35-33T2-2, H58N35-33T2, H58N35-33T3, H58N35-33T4 and H58N35-33T5, respectively).

The mutated protein H58N35-33T1 differs from HPV58N35 by: the substitution of the amino acid residues from positions 80 to 87 of wild type HPV58 L1 protein with the amino acid residues from positions 54 to 61 of wild type HPV33 L1 protein. The mutated protein H58N35-33T2 differs from HPV58N35 by: the substitution of the amino acid residues from positions 144 to 168 of wild type HPV58 L1 protein with the amino acid residues from positions 118 to 142 of wild type HPV33 L1 protein. The mutated protein H58N35-33T3 differs from HPV58N35 by: the substitution of the amino acid residues from positions 203 to 209 of wild type HPV58 L1 protein with the amino acid residues from positions 177 to 183 of wild type HPV33 L1 protein. The mutated protein H58N35-33T4 differs from HPV58N35 by: the substitution of the amino acid residues from positions 308 to 311 of wild type HPV58 L1 protein with the amino acid residues from positions 282 to 285 of wild type HPV33 L1 protein. The mutated protein H58N35-33T5 differs from HPV58N35 by: the substitution of the amino acid residues from positions 376 to 383 of wild type HPV58 L1 protein with the amino acid residues from positions 350 to 357 of wild type HPV33 L1 protein.

Gibson assembly (Gibson D G, Young L, Chuang R Y, Venter J C, Hutchison C A, Smith H O. Enzymatic assembly of DNA molecules up to several hundred kilobases. Nat Methods. 2009; 6:343-5. doi: 10.1038/ntneth.1318) was used to construct the expression vector encoding the mutated HPV58 L1 protein having double substitutions, wherein the mutated HPV58 L1 protein comprised a segment from HPV33 L1 and a segment from HPV52L1. In brief, a short fragment comprising mutations and a long fragment comprising no mutation were obtained by PCR, and Gibson assembly system was then used to ligate the two fragments to form a ring. The initial template used comprised the plasmid pTO-T7-H58N35-33T1 (encoding the mutated protein H58N35-33T1; abbreviated as H58N35-33T1 in Table 2) and the plasmid pTO-T7-HPV52N40C (encoding the HPV52 L1 protein having 40 amino acids truncated at N-terminal; abbreviated as 52L1N40 in Table 2). The templates and primers for each PCR were shown in Table 2, and, the amplification conditions for PCR for amplifying the short fragment were as followed: denaturation at 94° C. for 10 min; 25 cycles (denaturation at 94° C. for 50 sec, annealing at a given temperature for a certain period of time, and extension at 72° C. for 1 min); and final extension at 72° C. for 10 min. The amplification conditions for PCR for amplifying the long fragment were as followed: denaturation at 94° C. for 10 min; 25 cycles (denaturation at 94° C. for 50 sec, annealing at a given temperature for a certain period of time, and extension at 72° C. for 7.5 min); and final extension at 72° C. for 10 min. The sequences of the PCR primers used were listed in Table 3. The amplification product was subjected to electrophoresis, the fragment of interest was then recovered by using DNA Extraction Kit, and its concentration was determined. The short fragment and long fragment obtained by amplification were mixed at a molar ratio of 2:1 (a total volume of 3 μL), and 34 of 2× Gibson Assembly Master Mix (purchased from NEB, containing 15 exonuclease, Phusion DNA polymerase, Taq DNA ligase) was then added, and reacted at 50° C. for 1 h.

The assembled product (64) was used to transform 40 μL competent *E. coli* ER2566 (purchased from New England Biolabs) prepared by the Calcium chloride method. The transformed *E. coli* were spread onto solid LB medium containing kanamycin, and were subjected to static culture at 37° C. for 10-12 h until single colonies could be observed clearly. Single colony was picked and inoculated into a tube containing 4 mL liquid LB medium (containing kanamycin), and cultured with shaking at 220 rpm for 10 h at 37° C., and then 1 ml bacterial solution was taken and stored at −70° C. Plasmids were extracted from *E. coli*, and T7 primer was used to sequence the nucleotide sequences of the fragments of interest inserted into the plasmids. The sequencing result showed that the nucleotide sequences of the fragments of interest inserted into the constructed plasmids (expression vectors) were SEQ ID NO: 25, 26, 27, and 28, respectively, and their encoded amino acid sequences were SEQ ID NO: 11, 12, 13, and 14, respectively (the corresponding proteins were designated as H58N35-33T1-52S1, H58N35-33T1-52S2, 1-158N35-33T1-52S3, and H58N35-33T1-52S4, respectively).

The mutated protein H58N35-33T1-52S1 differs from HPV58N35 by: the substitution of the amino acid residues from positions 80 to 87 of wild type HPV58 L1 protein with the amino acid residues from positions 54 to 61 of wild type HPV33 L1 protein, and the substitution of the amino acid residues from positions 144 to 168 of wild type HPV58 L1 protein with the amino acid residues from positions 146 to 170 of wild type HPV52 L1 protein. The mutated protein H58N35-33T1-52S2 differs from HPV58N35 by: the substitution of the amino acid residues from positions 80 to 87 of wild type HPV58 L1 protein with the amino acid residues from positions 54 to 61 of wild type HPV33 L1 protein, and the substitution of the amino acid residues from positions 200 to 209 of wild type HPV58 L1 protein with the amino acid residues from positions 202 to 212 of wild type HPV52 L1 protein. The mutated protein H58N35-33T1-52S3 differs from HPV58N35 by: the substitution of the amino acid residues from positions 80 to 87 of wild type HPV58 L1 protein with the amino acid residues from positions 54 to 61 of wild type HPV33 L1 protein, and the substitution of the amino acid residues from positions 292 to 312 of wild type HPV58 L1 protein with the amino acid residues from positions 295 to 317 of wild type HPV52 L1 protein. The mutated protein H58N35-33T1-52S4 differs from HPV58N35 by: the substitution of the amino acid residues from positions 80 to 87 of wild type HPV58 L1 protein with the amino acid residues from positions 54 to 61 of wild type HPV33 L1 protein, and the substitution of the amino acid residues from positions 375 to 383 of wild type HPV58 L1 protein with the amino acid residues from positions 380 to 388 of wild type HPV52 L1 protein.

TABLE 2

PCR templates and primers for constructing expression vectors

| Template | Upstream primer | Downstream primer | Product |
| --- | --- | --- | --- |
| 58L1N35 | H58N35-33T1-F | H58N35-33T1-R | H58N35-33T1 |
| 58L1N35 | H58N35-33T2-1F | H58N35-33T2-1R | H58N35-33T2-1 |
| H58N35-33T2-1 | H58N35-33T2-2F | H58N35-33T2-2R | H58N35-33T2-2 |
| H58N35-33T2-2 | H58N35-33T2-3F | H58N35-33T2-3R | H58N35-33T2 |
| 58L1N35 | H58N35-33T3-F | H58N35-33T3-R | H58N35-33T3 |
| 58L1N35 | H58N35-33T4-F | H58N35-33T4-R | H58N35-33T4 |
| 58L1N35 | H58N35-33T5-F | H58N35-33T5-R | H58N35-33T5 |
| H58N35-33T1 | G-V-H58N35-33T1-52S1-F | G-V-H58N35-33T1-52S1-R | H58N35-33T1-52S1 long fragment |
| H58N35-33T1 | G-V-H58N35-33T1-52S2-F | G-V-H58N35-33T1-52S2-R | H58N35-33T1-52S2 long fragment |
| H58N35-33T1 | G-V-H58N35-33T1-52S3-F | G-V-H58N35-33T1-52S3-R | H58N35-33T1-52S3 long fragment |
| H58N35-33T1 | G-V-H58N35-33T1-52S4-F | G-V-H58N35-33T1-52S4-R | H58N35-33T1-52S4 long fragment |
| 52L1N40 | G-H58N35-33T1-52S1-F | G-H58N35-33T1-52S1-R | H58N35-33T1-52S1 short fragment |
| 52L1N40 | G-H58N35-33T1-52S2-F | G-H58N35-33T1-52S2-R | H58N35-33T1-52S2 short fragment |
| 52L1N40 | G-H58N35-33T1-52S3-F | G-H58N35-33T1-52S3-R | H58N35-33T1-52S3 short fragment |
| 52L1N40 | G-H58N35-33T1-52S4-F | G-H58N35-33T1-52S4-R | H58N35-33T1-52S4 short fragment |

TABLE 3

Sequences of the primers used (SEQ ID NOs: 29-58)

| SEQ ID NO: | Primer name | Primer sequence (5'-3') |
|---|---|---|
| 29 | H58N35-33T1-F | CTTCAGCATCAAGAATCCCACTAACGCTAAAAAATTACTGGTGCCCAAGG |
| 30 | H58N35-33T1-R | CCTTGGGCACCAGTAATTTTTTAGCGTTAGTGGGATTCTTGATGCTGAAG |
| 31 | H58N35-33T2-1F | CCTGGGCGTCGGAATAAGCGGCCACCCCTTACTGAACAAGTTCG |
| 32 | H58N35-33T2-1R | CGAACTTGTTCAGTAAGGGGTGGCCGCTTATTCCGACGCCCAGG |
| 33 | H58N35-33T2-2F | CGACACCGAGACCGGAAACAAGTACCCCGCCCAGC |
| 34 | H58N35-33T2-2R | GCTGGGCGGGGTACTTGTTTCCGGTCTCGGTGTCG |
| 35 | H58N35-33T2-3F | AACAAGTACCCCGGACAGCCCGGCGCTGACAACAGGGAGT |
| 36 | H58N35-33T2-3R | ACTCCCTGTTGTCAGCGCCGGGCTGTCCGGGGTACTTGTT |
| 37 | H58N35-33T3-F | GGGGCAAGGGAGTAGCATGTACAAACGCTGCACCTGCCAACGACTGC |
| 38 | H58N35-33T3-R | GCAGTCGTTGGCAGGTGCAGCGTTTGTACATGCTACTCCCTTGCCCC |
| 39 | H58N35-33T4-F | CAAGGGCAGCGGCACAACAGCAAGTATCCAGAGCAGCG |
| 40 | H58N35-33T4-R | CGCTGCTCTGGATACTTGCTGTTGTGCCGCTGCCCTTG |
| 41 | H58N35-33T5-F | CCGAGGTGACCAGCGACAGCACGTACAAGAACGAGAACTTCAAGGAG |
| 42 | H58N35-33T5-R | CTCCTTGAAGTTCTCGTTCTTGTACGTGCTGTCGCTGGTCACCTCGG |
| 43 | G-V-H58N35-33T1-52S1-F | CTGATCGGCTGCAAGCCCCCCAC |
| 44 | G-V-H58N35-33T1-52S1-R | CACGCAGGCCCACACCAGCC |
| 45 | G-V-H58N35-33T1-52S2-F | GAGCTGTTCAACAGCATCATCGAGG |
| 46 | G-V-H58N35-33T1-52S2-R | GGTGGGGGGCTTGCAGCCGATC |
| 47 | G-V-H58N35-33T1-52S3-F | ATCGTGACCAGCGAGAGCCAGC |
| 48 | G-V-H58N35-33T1-52S3-R | CTTCAGGTAGTCGGGGTACTTGC |
| 49 | G-V-H58N35-33T1-52S4-F | GTGAGGCACGTGGAGGAGTACG |
| 50 | G-V-H58N35-33T1-52S4-R | GGTGCACAGGGTCATGTTGGTG |
| 51 | G-H58N35-33T1-52S1-F | GAGGCTGGTGTGGGCCTGCGTGGGCCTGGAGATCGGCAGG |
| 52 | G-H58N35-33T1-52S1-R | TGGGGGGCTTGCAGCCGATCAGGCACAGCTGGGTCTGCTTG |
| 53 | G-H58N35-33T1-52S2-F | TGATCGGCTGCAAGCCCCCCACCGGCGAGCACTGGGCAAGGG |
| 54 | G-H58N35-33T1-52S2-R | TCGATGATGCTGTTGAACAGCTCCAGGGGGGGCAGTCGCCG |

TABLE 3-continued

Sequences of the primers used (SEQ ID NOs: 29-58)

| SEQ ID NO: | Primer name | Primer sequence (5'-3') |
|---|---|---|
| 55 | G-H58N35-33T1-52S3-F | GCAAGTACCCCGACTACCTGAAGATGGCCAGCGAGCCCT |
| 56 | G-H58N35-33T1-52S3-R | GCTGGCTCTCGCTGGTCACGATGCTGCCGCTGGGGGTG |
| 57 | G-H58N35-33T1-52S4-F | CACCAACATGACCCTGTGCACCGAGGTGAAGAAGGAGAG |
| 58 | G-H58N35-33T1-52S4-R | CGTACTCCTCCACGTGCCTCACGTACTCCTTGAAGTTCTCG |

Expression of the Mutated Proteins on a Large Scale

The E. coli solutions comprising the recombinant plasmid pTO-T7-H58N35-33T1, pTO-T7-H58N35-33T2, pTO-T7-H58N35-33T3, pTO-T7-H58N35-33T4, pTO-T7-H58N35-33T5, pTO-T7-H58N35-33T1-52S1, pTO-T7-H58N35-33T1-52S2, pTO-T7-H58N35-33T1-52S3, and pTO-T7-H58N35-33T1-52S4, respectively, were taken from −70° C. refrigerator, were seeded in 100 mL LB liquid medium containing kanamycin, and incubated at 200 rpm and 37° C. for about 8 h. Then, the culture was transferred to 500 mL LB medium containing kanamycin (1 ml bacterial solution was transferred), and was further incubated. When the bacterial concentration reached an $OD_{600}$ of about 0.6, the culturing temperature was lowered to 25° C. and 500 μL IPTG was added to each culture bottle. The incubation was further performed for 8 h. After the incubation was finished, the bacteria were collected by centrifugation. The bacteria expressing H58N35-33T1, H58N35-33T2, H58N35-33T3, H58N35-33T4, H58N35-33T5, H58N35-33T1-52S1, H58N35-33T1-52S2, H58N35-33T1-52S3, and H58N35-33T1-52S4 protein, were obtained, respectively.

Disruption of Bacteria Expressing the Mutated Proteins

The bacteria obtained were re-suspended at a ratio of 1 g bacteria to 10 mL lysis buffer (20 mM Tris buffer, pH7.2, 300 mM NaCl). The bacteria were disrupted by using an ultrasonic apparatus for 30 min. The lysis solution containing the disrupted bacteria were centrifuged at 13500 rpm (30000 g) for 15 min, and the supernatant (i.e. the supernatant of disrupted bacteria) was obtained.

Chromatographic Purification of the Mutated Protein

Equipment: AKTA Explorer 100 preparative liquid chromatography system produced by GE Healthcare (i.e. the original Amershan Pharmacia Co.)

Chromatographic media: SP Sepharose 4 Fast Flow (GE Healthcare Co.), CHT-II (purchased from Bio-RAD) and Butyl Sepharose 4 Fast Flow (GE Healthcare Co.)

Buffer: 20 mM phosphate buffer, pH8.0, 20 mM DTT; and, 20 mM phosphate buffer, pH8.0, 20 mM DTT, 2 M NaCl.

Sample: the supernatants of disrupted bacteria containing H58N35-33T1, H58N35-33T2, H58N35-33T3, H58N35-33T4, H58N35-33T5, H58N35-33T1-52S1, H58N35-33T1-52S2, H58N35-33T1-52S3, and H58N35-33T1-52S4, respectively, as obtained above.

Elution Protocol (1) Cation exchange purification of the supernatant of disrupted bacteria by SP Sepharose 4 Fast Flow: the sample was loaded on the column, undesired proteins were then eluted with a buffer containing 400 mM NaCl, followed by the elution of the protein of interest with a buffer containing 800 mM NaCl, and the fraction eluted with the buffer containing 800 mM NaCl was collected;

(2) Chromatographic purification of the elution fraction obtained in the step (1) by CHTII (hydroxyapatite chromatography): the elution fraction obtained in the step (1) was diluted so that the NaCl concentration was decreased to 0.5 M; the sample was loaded on the column, undesired proteins were then eluted with a buffer containing 500 mM NaCl, followed by the elution of the protein of interest with a buffer containing 1000 mM NaCl, and the fraction eluted with the buffer containing 1000 mM NaCl was collected;

(3) Chromatographic purification of the elution fraction obtained in the step (2) by HIC (hydrophobic interaction chromatography): the sample was loaded on the column, undesired proteins were then eluted with a buffer containing 1000 mM NaCl, followed by the elution of the protein of interest with a buffer containing 200 mM NaCl, and the fraction eluted with the buffer containing 200 mM NaCl was collected.

150 μL elution fraction obtained in the step (3) was added to 30 μL of 6× Loading Buffer. The resultant solution was mixed homogeneously and incubated in 80° C. water bath for 10 mM. 10 μl of the resultant sample was then subjected to 10% SDS-PAGE at 120V for 120 mM; and the electrophoretic bands were stained by Coomassie brilliant blue. The electrophoretic result was shown in FIG. 1. The result showed that after said purification steps, H58N35-33T1, H58N35-33T2, H58N35-33T3, H58N35-33T4, H58N35-33T5, H58N35-33T1-52S1, H58N35-33T1-52S2, H58N35-33T1-52S3, and H58N35-33T1-52S4 protein had a purity of above 95%.

By similar methods, HPV58N35 protein was prepared and purified by using E. coli and the plasmid pTO-T7-HPV58L1N35C; HPV52N40 protein was prepared and purified by using E. coli and the plasmid pTO-T7-HPV52N40C; and HPV33N9 protein was prepared and purified by using E. coli and the plasmid pTO-T7-HPV33L1N9C (encoding HPV33N9 protein).

Western Blot Assay of the Mutated Proteins

Figure 2:
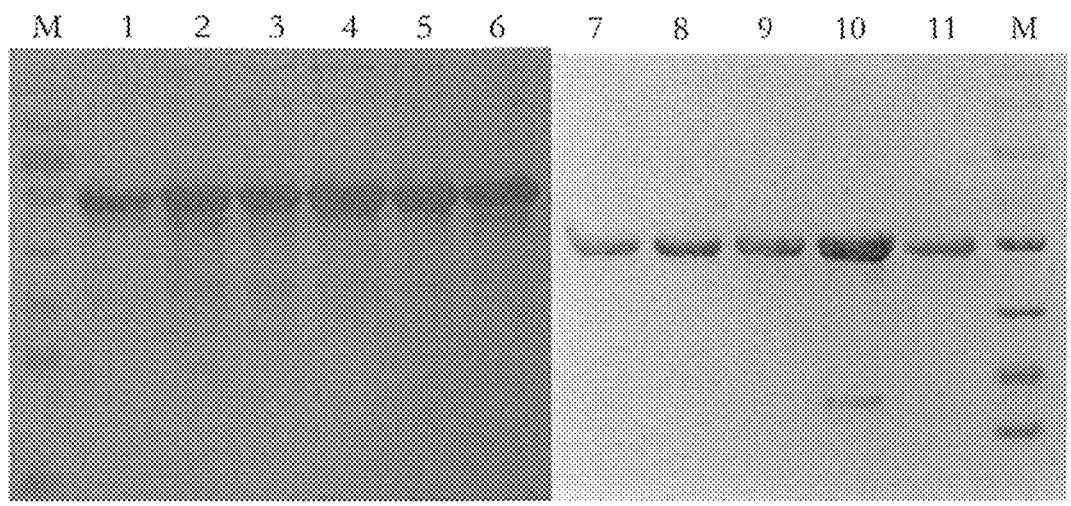
FIG. 2 shows the Western Blot result of H58N35-33T1, H58N35-33T2, H58N35-33T3, H58N35-33T4, H58N35-33T5, H58N35-33T1-52S1, H58N35-33T1-52S2, H58N35-33T1-52S3, and H58N35-33T1-52S4 prepared in Example 1, as determined by using a broad-spectrum antibody 4B3. Lane M: protein molecular weight marker; Lane 1: HPV58N35; Lane 2: H58N35-33T1; Lane 3: H58N35-33T2; Lane 4: H58N35-33T3; Lane 5: H58N35-33T4; Lane 6: H58N35-33T5; Lane 7: H58N35-33T1; Lane 8: H58N35-33T1-52S1; Lane 9: H58N35-33T1-52S2; Lane 10: H58N35-33T1-52S3; Lane 11: H58N35-33T1-52S4. The result showed that the mutated proteins H58N35-33T1, H58N35-33T2, H58N35-33T3, H58N35-33T4, H58N35-33T5, H58N35-33T1-52S1, H58N35-33T1-52S2, H58N35-33T1-52S3, and H58N35-33T1-52S4 could be specifically recognized by the broad-spectrum antibody 4B3.
Figure 3A:
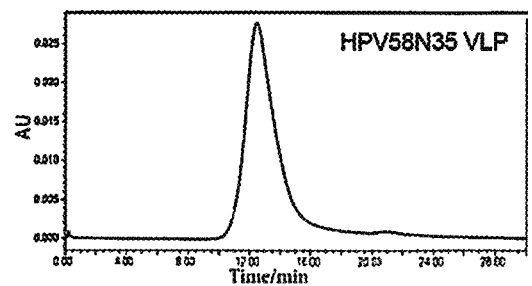
FIGS. 3A-3L show the results of the samples comprising the protein HPV58N35, H58N35-33T1, H58N35-33T2, H58N35-33T3, H58N35-33T4, H58N35-33T5, HPV33N9 (HPV33 L1 protein having 9 amino acids truncated at N-terminal), H58N35-33T1-52S1, H58N35-33T1-52S2, H58N35-33T1-52S3, H58N35-33T1-52S4, and HPV52N40 (HPV52 L1 protein having 40 amino acids truncated at N-terminal), as analyzed by molecular sieve chromatography. The results showed that the first protein peak of the samples comprising the protein H58N35-33T1, H58N35-33T3, H58N35-33T4, H58N35-33T5, H58N35-33T1-52S1, H58N35-33T1-52S2, H58N35-33T1-52S3, or H58N35-33T1-52S4 appeared at about 12 min, which was comparable to that of HPV58N35 VLP, HPV33N9 VLP and HPV52N40 VLP. This showed that all these proteins were able to assemble into VLPs. However, the first protein peak of the sample comprising the protein H58N35-33T2 appeared at about 16 min, which was comparable to the retention time of the pentamer of HPV58 L1 protein, indicating that the protein was unable to assemble into VLP.
Figure 3B:
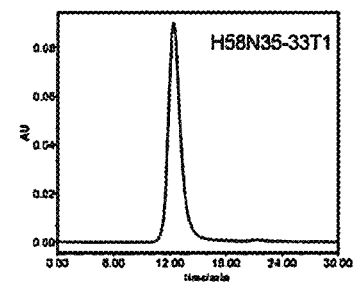
Figure 3C:
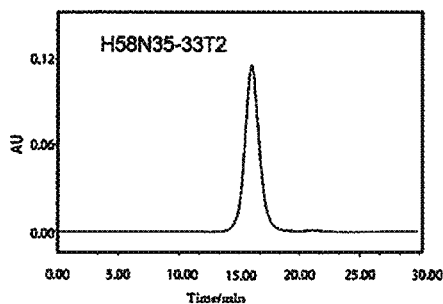
Figure 3D:
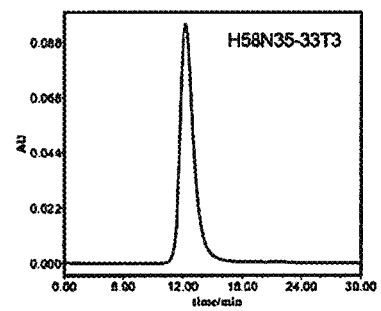
Figure 3E:
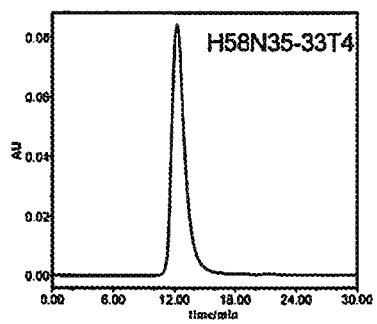
Figure 3F:
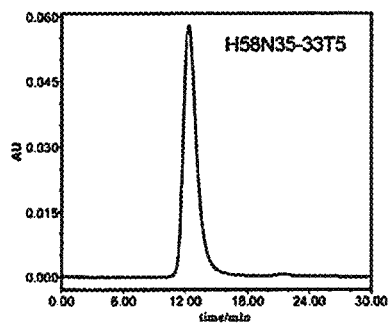
Figure 3G:
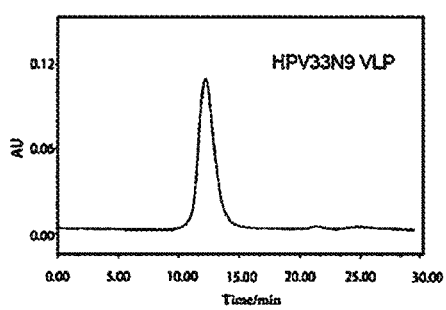
Figure 3H:
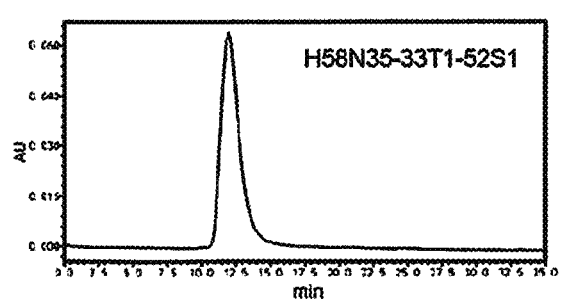
Figure 3I:
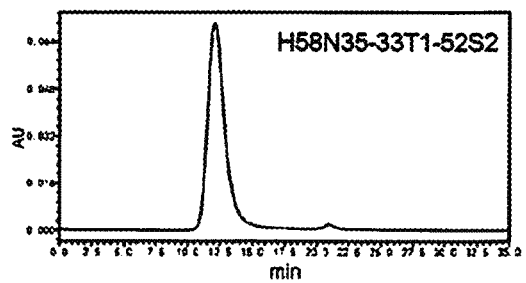
Figure 3J:
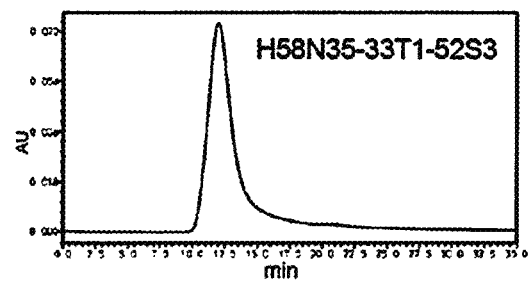
Figure 3K:
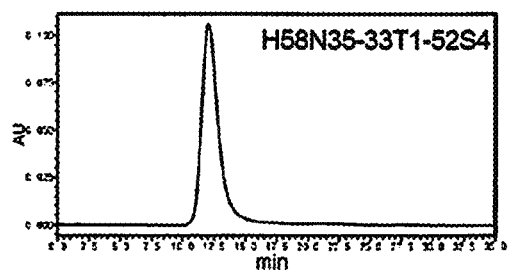
Figure 3L:
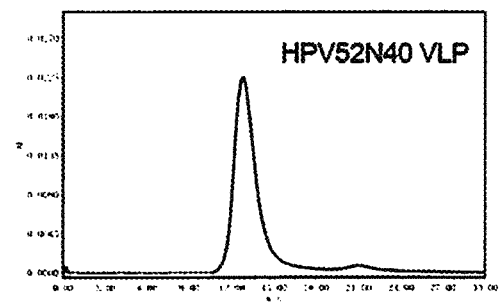
Figure 4A:
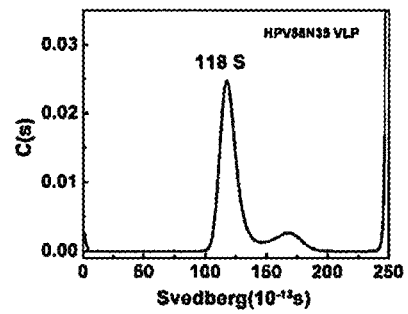
FIGS. 4A-4F show the results of sedimentation velocity analysis of HPV58N35 VLP, HPV33N9 VLP, HPV52N40 VLP, H58N35-33T1 VLP, H58N35-33T1-52S1 VLP, and H58N35-33T1-52S4 VLP.
Figure 4B:
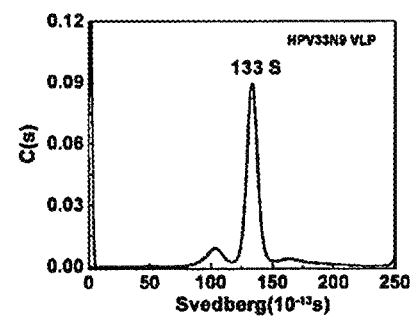
Figure 4C:
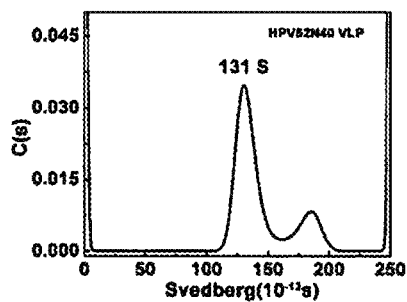
Figure 4D:
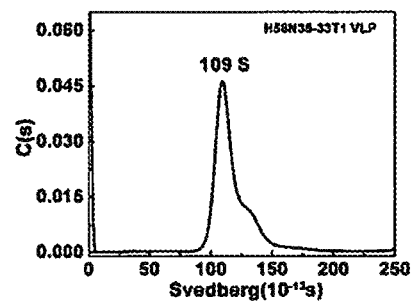
Figure 4E:
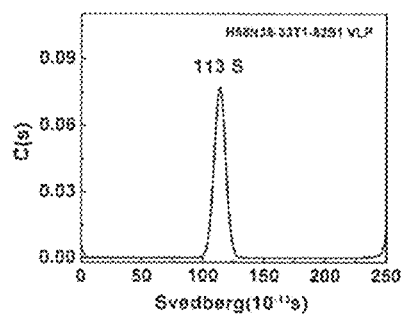
Figure 4F:
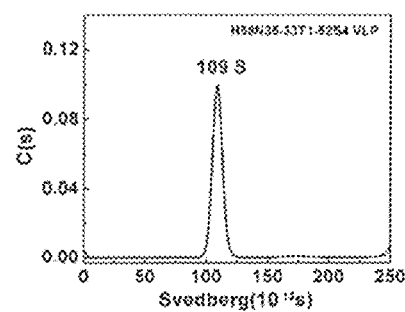
Figure 5A:
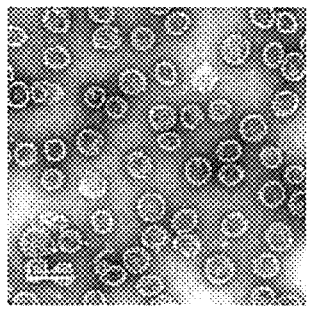
FIGS. 5A-5L show the transmission electron microscopy (TEM) photographs (taken at 100,000× magnification, Bar=0.1 μm) of various VLP samples.
Figure 5B:
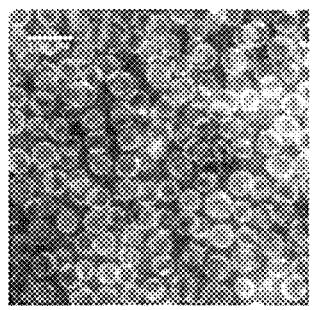
Figure 5C:
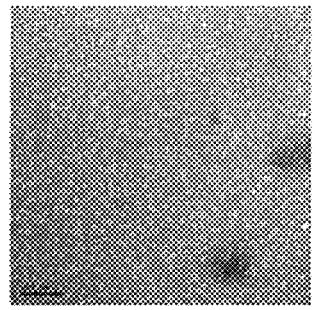
Figure 5D:
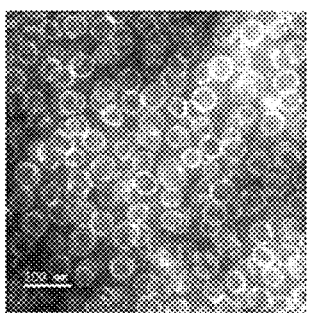
Figure 5E:
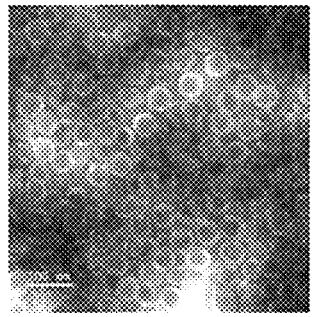
Figure 5F:
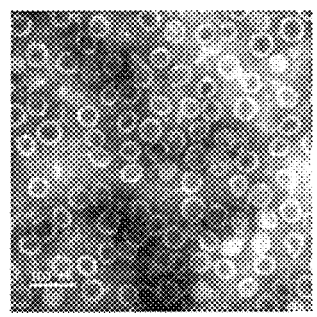
Figure 5G:
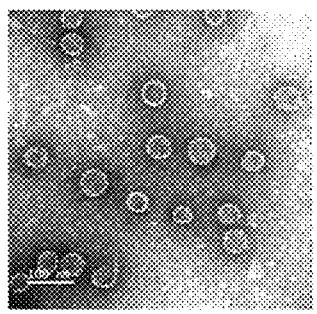
Figure 5H:
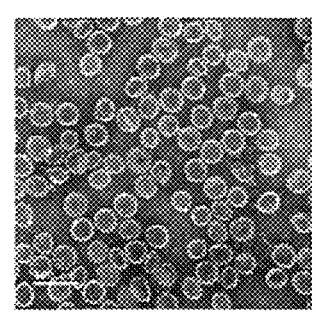
Figure 5I:
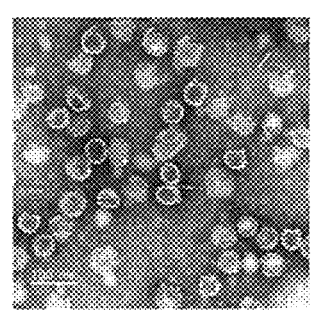
Figure 5J:
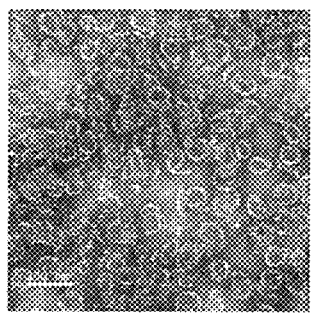
Figure 5K:
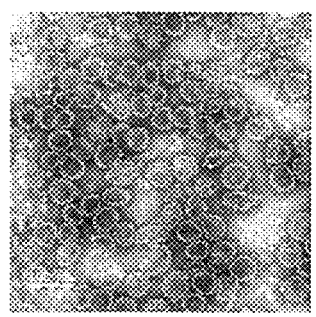
Figure 5L:
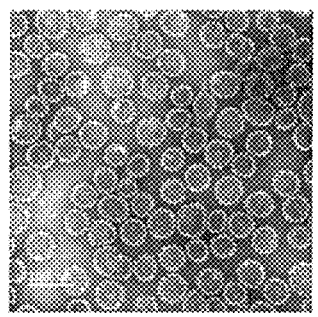
Figure 6A:
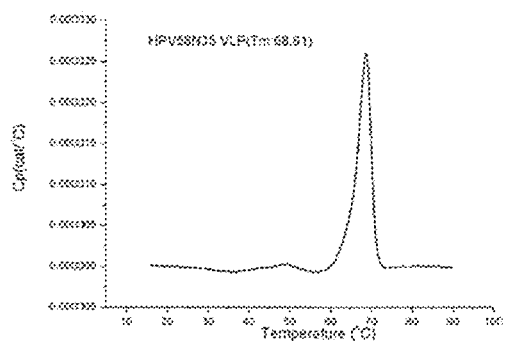
FIGS. 6A-6F show the detection results of thermostability of H58N35-33T1 VLP, H58N35-33T1-52S1 VLP, H58N35-33T1-52S2 VLP, H58N35-33T1-52S3 VLP, and H58N35-33T1-52S4 VLP.
Figure 6B:
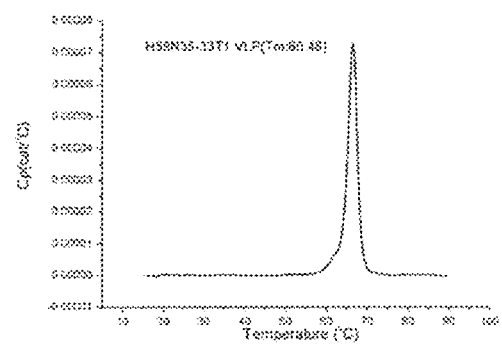
Figure 6C:
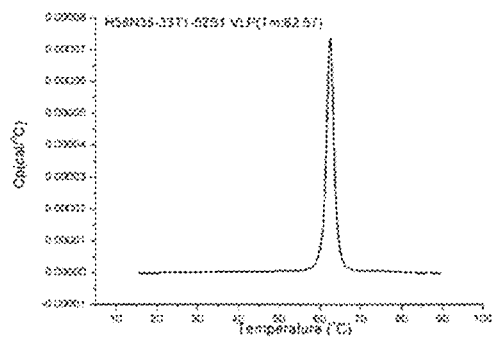
Figure 6D:
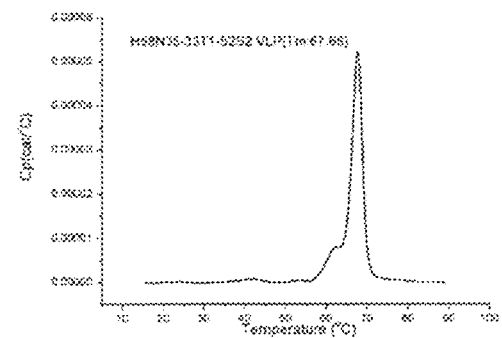
Figure 6E:
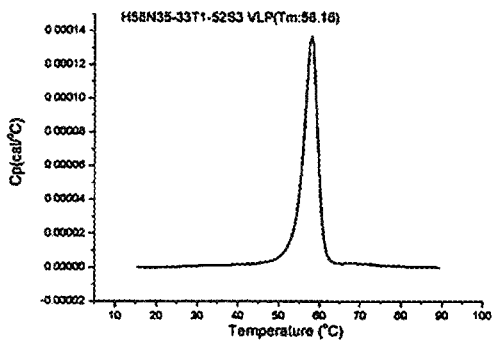
Figure 6F:
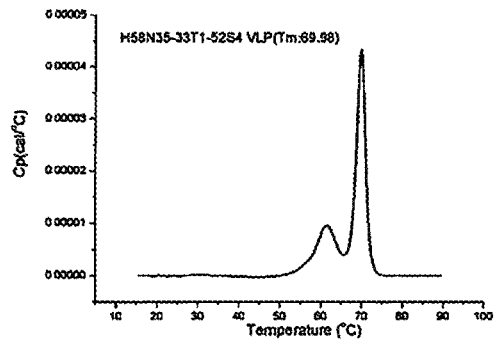

The H58N35-33T1, H58N35-33T2, H58N35-33T3, H58N35-33T4, H58N35-33T5, H58N35-33T1-52S1, H58N35-33T1-52S2, H58N35-33T1-52S3, and H58N35-33T1-52S4 purified by the method above were subjected to electrophoresis. After electrophoresis, Western Blot assay was carried out by using a broad-spectrum antibody 4B3 against HPV L1 protein, and the result was shown in FIG. 2. The result showed that H58N35-33T1, H58N35-33T2, H58N35-33T3, H58N35-33T4, H58N35-33T5, H58N35-33T1-52S1, H58N35-33T1-52S2, H58N35-33T1-52S3, and H58N35-33T1-52S4 could be specifically recognized by the broad-spectrum antibody 4B3.

EXAMPLE 2: ASSEMBLY OF HPV VIRUS-LIKE PARTICLES AND MORPHOLOGICAL DETECTION OF PARTICLES

Assembly of HPV Virus-Like Particles

A given volume (about 2 ml) of the protein H58N35-33T1, H58N35-33T2, H58N35-33T3, H58N35-33T4, H58N35-33T5, H58N35-33T1-52S1, H58N35-33T1-52S2, H58N35-33T1-52S3, or H58N35-33T1-52S4, was dialyzed to (1) 2 L storage buffer (20 mM sodium phosphate buffer pH 6.5, 0.5 M NaCl); (2) 2 L renaturation buffer (50 mM sodium phosphate buffer pH 6.0, 2 mM $CaCl_2$, 2 mM $MgCl_2$, 0.5 M NaCl); and (3) 20 mM sodium phosphate buffer pH 7.0, 0.5 M NaCl, successively. The dialysis was performed in each of the three buffers for 12 h.

By similar methods, the HPV58N35, HPV33N9 and HPV52N40 protein were assembled into HPV58N35 VLP, HPV33N9 VLP and HPV52N40 VLP, respectively.

Molecular Sieve Chromatographic Analysis

The dialyzed sample was subjected to molecular sieve chromatographic analysis by 1120 Compact LC High Performance Liquid Chromatographic System (Agilent Technologies), wherein the analytical column used was TSK Gel PW5000xl 7.8×300 mm. The analysis results were shown in FIGS. 3A-3L. The results showed that the first protein peak of the samples comprising the protein H58N35-33T1, H58N35-33T3, H58N35-33T4, H58N35-33T5, H58N35-33T1-52S1, H58N35-33T1-52S2, H58N35-33T1-52S3, and H58N35-33T1-52S4 appeared at about 12 min, which was comparable to that of HPV58N35 VLP, HPV33N9 VLP and HPV52N40 VLP. This showed that all these protein were able to assemble into VLPs. However, the first protein peak of the sample comprising the protein H58N35-33T2 appeared at about 16 min, which was comparable to the retention time of the pentamer of HPV58 L1 protein, indicating that the protein was unable to assemble into VLP.

Sedimentation Velocity Analysis

The apparatus for sedimentation velocity analysis was Beckman XL-A Analytical Ultracentrifuge, equipped with optical inspection system and An-50Ti and An-60Ti rotor. The sedimentation coefficient of H58N35 VLP, HPV33N9 VLP and H58N35-33T1 VLP was analyzed by sedimentation velocity method. The results were shown in FIGS. 4A-4F. The results showed that the sedimentation coefficient of H58N35-33T1 VLP, H58N35-33T1-52S1 VLP and H58N35-33T1-52S4 VLP was 109S, 113S and 109S, respectively, while the sedimentation coefficient of HPV58N35 VLP, HPV33N9 VLP and HPV52N40 VLP was 118S, 133S and 131S, respectively. This showed that H58N35-33T1, H58N35-33T1-52S1 and H58N35-33T1-52S4 were able to assemble into virus-like particles that were similar to wild type VLP in terms of size and morphology.

Morphological Test of Virus-Like Particles

A 100 µL sample comprising VLP was observed by transmission electron microscope (TEM). The equipment used was a 100 kV Transmission Electron Microscope supplied by JEOL Ltd. (100,000× magnification). In brief, a 13.5 µL sample was negatively stained with 2% phosphotungstic acid (pH 7.0), fixed on a carbon-coated copper grid, and then observed by TEM. The results were shown in FIGS. 5A-5L. The results showed that H58N35-33T1, H58N35-33T3, H58N35-33T4, H58N35-33T5, H58N35-33T1-52S1, H58N35-33T1-52S2, H58N35-33T1-52S3, and H58N35-33T1-52S4 were able to assemble into virus-like particles. In addition, the results also showed that the particles assembled by these mutated proteins had a radius of about 30 nm, and were uniform in size. This indicated that these mutated proteins were similar to the L1 protein of HPV33, HPV58 and HPV52, and were able to assemble into VLPs with a uniform size. H58N35-33T2 could only form pentamer, but was unable to assemble into virus-like particle.

EXAMPLE 3: EVALUATION OF THERMOSTABILITY OF VIRUS-LIKE PARTICLES

The VLPs formed by H58N35-33T1, H58N35-33T1-52S1, H58N35-33T1-52S2, H58N35-33T1-52S3, and H58N35-33T1-52S4 were evaluated for their thermostability by using a differential scanning calorimeter VP Capillary DSC purchased from GE Company (i.e. the MicroCal Co.), wherein the storage buffer for the protein was used as control, and the proteins were scanned at a heating rate of 1.5° C./min within a temperature range of 10° C.-90° C. The detection results were shown in FIGS. 6A-6F. The results showed that all these VLPs formed by the proteins had very high thermostability.

EXAMPLE 4: EVALUATION 1 OF IMMUNE PROTECTION OF VIRUS-LIKE PARTICLES IN ANIMALS

The immune protection of the VLPs formed by H58N35-33T1, H58N35-33T3, H58N35-33T4, H58N35-33T5, H58N35-33T1-52S1, H58N35-33T1-52S2, H58N35-33T1-52S3, and H58N35-33T1-52S4, was evaluated in mice. Animals for vaccination were BALB/c mice (ordinary grade), 5-6 weeks old (purchased from Shanghai SLAC Laboratory Animal Co. LTD.).

Figure 7A:
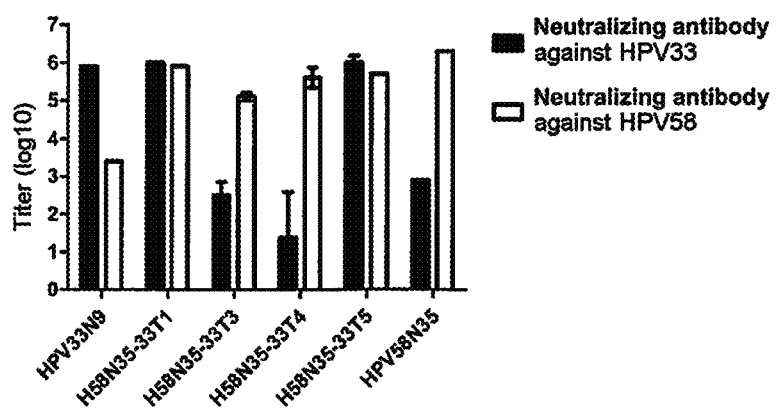
FIG. 7A shows the evaluation result of immune protection of H58N35-33T1 VLP, H58N35-33T3 VLP, H58N35-33T4 VLP and H58N35-33T5 VLP in mice of the Experimental groups, and of HPV58N35 VLP and HPV33N9 VLP in mice of the Control groups. The result showed that either of H58N35-33T1 VLP and H58N35-33T5 VLP could induce the generation of high-titer neutralizing antibodies against HPV33 and HPV58 in mice; and their protective effects against HPV58 were comparable to that of HPV58N35 VLP alone, and were significantly higher than that of HPV33N9 VLP alone; and their protective effects against HPV33 were comparable to that of HPV33N9 VLP alone, and were significantly higher than that of HPV58N35 VLP alone. This showed that H58N35-33T1 VLP and H58N35-33T5 VLP could be used as effective vaccines for preventing HPV58 infection and HPV33 infection, and could be used in place of a mixed vaccine comprising HPV58 VLP and HPV33 VLP.

The H58N35-33T1 VLP, H58N35-33T3 VLP, H58N35-33T4 VLP, H58N35-33T5 VLP, HPV58N35 VLP and HPV33N9 VLP as prepared above were absorbed onto Freund's adjuvant, respectively. Mice were divided into 6 groups depending on immunogen, and each group included 3 mice. Vaccination procedure was as followed: the first vaccination at Week 0, and the booster vaccination at Weeks 2 and 4, respectively. Mice were vaccinated via subcutaneous injection. The immunogens used and doses thereof were shown in Table 4. At Week 8 after the first vaccination, venous blood was collected from eyeball, and serum was separated. The titers of neutralizing antibodies in the serum were determined. The detection result was shown in FIG. 7A. The result showed that either of H58N35-33T1 VLP and H58N35-33T5 VLP could induce the generation of high-titer neutralizing antibodies against HPV33 and HPV58 in mice; and their protective effects against HPV58 were comparable to that of HPV58N35 VLP alone, and were significantly higher than that of HPV33N9 VLP alone; and their protective effects against HPV33 were comparable to that of HPV33N9 VLP alone, and were significantly higher than that of HPV58N35 VLP alone. This showed that H58N35-33T1 VLP and H58N35-33T5 VLP could be used as effective vaccines for preventing HPV58 infection and HPV33 infection, and could be used in place of a mixed vaccine comprising HPV58 VLP and HPV33 VLP.

TABLE 4

Vaccination schedule

| Antigen for vaccination | Adjuvant | Immunizing dose | Number | Vaccination procedure (week) |
|---|---|---|---|---|
| HPV33N9 VLP | Freund's adjuvant | 100 μg | 3 | 0, 2, 4 |
| HPV58N35 VLP | Freund's adjuvant | 100 μg | 3 | 0, 2, 4 |
| H58N35-33T1VLP | Freund's adjuvant | 100 μg | 3 | 0, 2, 4 |
| H58N35-33T3 VLP | Freund's adjuvant | 100 μg | 3 | 0, 2, 4 |
| H58N35-33T4 VLP | Freund's adjuvant | 100 μg | 3 | 0, 2, 4 |
| H58N35-33T5 VLP | Freund's adjuvant | 100 μg | 3 | 0, 2, 4 |

Figure 7B:
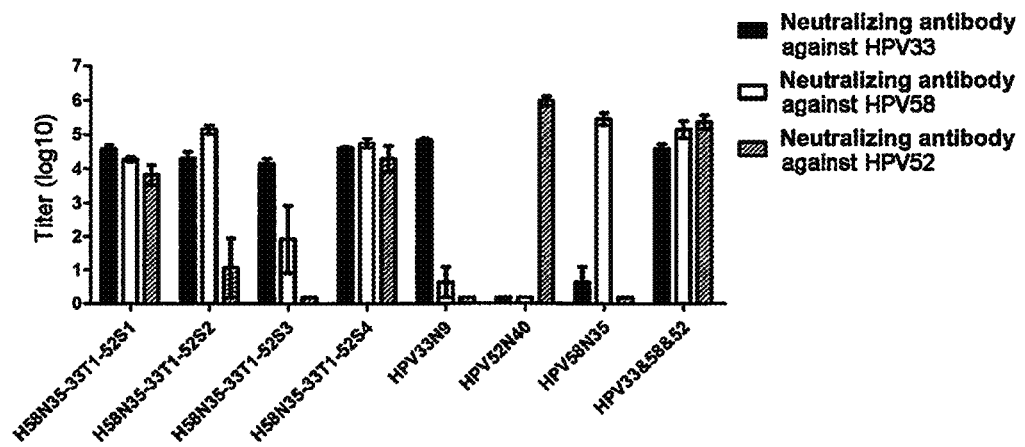
FIG. 7B shows the evaluation result of immune protection of H58N35-33T1-52S1, H58N35-33T1-52S2, H58N35-33T1-52S3 and H58N35-33T1-52S4 in mice of the Experimental groups, and of HPV58N35 VLP, HPV33N9 VLP, HPV52N40 VLP, and the mixed HPV58/HPV33/HPV52 VLP in mice of the Control groups. The result showed that either of 1158N35-33T1-52S1 VLP and H58N35-33T1-52S4 VLP could induce the generation of high-titer neutralizing antibodies against HPV58, HPV33 and HPV52 in mice; and their protective effects against HPV58 was comparable to that of HPV58N35 VLP alone and that of the mixed HPV58/HPV33/HPV52 VLP, and were significantly higher than that of HPV33N9 VLP alone and that of HPV52N40 VLP alone; and their protective effects against HPV33 were comparable to that of HPV33N9 VLP alone and that of the mixed HPV58/HPV33/HPV52 VLP, and were significantly higher than that of HPV58N35 VLP alone and that of HPV52N40 VLP alone; and their protective effects against HPV52 were comparable to that of HPV52N40 VLP alone and that of the mixed HPV58/HPV33/HPV52 VLP, and were significantly higher than that of HPV33N9 VLP alone and that of HPV58N35 VLP alone. This showed that H58N35-33T1-52S1 VLP and H58N35-33T1-52S4 VLP could be used as effective vaccines for preventing HPV58 infection, HPV33 infection and HPV52 infection, and could be used in place of a mixed vaccine comprising HPV58 VLP, HPV33 VLP and HPV52 VLP.

In addition, the H58N35-33T1-52S1 VLP, H58N35-33T1-52S2 VLP, H58N35-33T1-52S3 VLP, H58N35-33T1-52S4 VLP, HPV58N35 VLP, HPV33N9 VLP, HPV52N40 VLP and a mixed HPV58/HPV33/HPV52 VLP (i.e. a mixture of HPV58N35 VLP, HPV33N9 VLP and HPV52N40 VLP) as prepared above were absorbed onto aluminum adjuvant. Mice were divided into 8 groups depending on immunogen, and each group included 4 mice. Vaccination procedure was as followed: the first vaccination at Week 0, and the booster vaccination at Weeks 2 and 4, respectively. Mice were vaccinated via intraperitoneal injection. The immunogens and doses thereof were shown in Table 5. At Week 8 after the first vaccination, venous blood was collected from eyeball, and serum was separated. The titers of neutralizing antibodies in the serum were determined. The detection result was shown in FIG. 7B. The result showed that either of H58N35-33T1-52S1 VLP and H58N35-33T1-52S4 VLP could induce the generation of high-titer neutralizing antibodies against HPV58, HPV33 and HPV52 in mice; and their protective effects against HPV58 was comparable to that of HPV58N35 VLP alone and that of the mixed HPV58/HPV33/HPV52 VLP, and were significantly higher than that of HPV33N9 VLP alone and that of HPV52N40 VLP alone; and their protective effects against HPV33 were comparable to that of HPV33N9 VLP alone and that of the mixed HPV58/HPV33/HPV52 VLP, and were significantly higher than that of HPV58N35 VLP alone and that of HPV52N40 VLP alone; and their protective effects against HPV52 were comparable to that of HPV52N40 VLP alone and that of the mixed HPV58/HPV33/HPV52 VLP, and were significantly higher than that of HPV33N9 VLP alone and that of HPV58N35 VLP alone. This showed that H58N35-33T1-52S1 VLP and H58N35-33T1-52S4 VLP could be used as effective vaccines for preventing HPV58 infection, HPV33 infection and HPV52 infection, and could be used in place of a mixed vaccine comprising HPV58 VLP, HPV33 VLP and HPV52 VLP.

TABLE 5

Vaccination schedule

| Antigen for vaccination | Adjuvant | Immunizing dose | Number | Vaccination procedure (week) |
|---|---|---|---|---|
| HPV33N9 VLP | aluminum adjuvant | 5 μg | 4 | 0, 2, 4 |
| HPV52N40 VLP | aluminum adjuvant | 5 μg | 4 | 0, 2, 4 |
| HPV58N35 VLP | aluminum adjuvant | 5 μg | 4 | 0, 2, 4 |
| H58N35-33T1-52S1 VLP | aluminum adjuvant | 5 μg | 4 | 0, 2, 4 |
| H58N35-33T1-52S2 VLP | aluminum adjuvant | 5 μg | 4 | 0, 2, 4 |
| H58N35-33T1-52S3 VLP | aluminum adjuvant | 5 μg | 4 | 0, 2, 4 |
| H58N35-33T1-52S4 VLP | aluminum adjuvant | 5 μg | 4 | 0, 2, 4 |
| HPV58/HPV33/HPV52 VLP | aluminum adjuvant | 5 μg for each VLP | 4 | 0, 2, 4 |

EXAMPLE 5: EVALUATION 2 OF IMMUNE PROTECTION OF VIRUS-LIKE PARTICLES IN ANIMALS $ED_{50}$ of H58N35-33T1 VLP 6-week old BalB/c female mice (8 mice) were vaccinated with aluminum adjuvant by single intraperitoneal injection, wherein H58N35-33T1 VLP was used in the Experimental groups, and HPV58N35 VLP alone or HPV33N9 VLP alone was used in the Control groups; the immunizing dose was 0.300 μg, 0.100 μg, 0.033 μg, 0.011 μg or 0.004 μg; the immunizing volume was 1 mL. At Week 5 after vaccination, venous blood was collected from eyeball. Antibodies against HPV in the blood were detected, and by Reed-Muench method (Reed L J M H. A simple method of estimating fifty percent endpoints. Am J Hyg. 1938; 27:493-7), $ED_{50}$ for inducing seroconversion (i.e. inducing the generation of antibodies in mice) was calculated for each sample. The results were shown in Tables 6-8.

TABLE 6

ED$_{50}$ of HPV33N9 VLP for inducing the generation of antibodies against HPV33, HPV58 in mice

| Type | Dose (μg) | Total number of mice | Number of mice with positive conversion | Positive conversion rate | ED$_{50}$ (μg) |
|---|---|---|---|---|---|
| HPV33 | 0.300 | 8 | 8 | 100.00% | 0.066 |
|  | 0.100 | 8 | 5 | 70.00% |  |
|  | 0.033 | 8 | 1 | 16.67% |  |
|  | 0.011 | 8 | 1 | 5.56% |  |
|  | 0.004 | 8 | 0 | 0.00% |  |
| HPV58 | 0.300 | 8 | 0 | 0.00% | >0.3 |
|  | 0.100 | 8 | 0 | 0.00% |  |
|  | 0.033 | 8 | 0 | 0.00% |  |
|  | 0.011 | 8 | 0 | 0.00% |  |
|  | 0.004 | 8 | 0 | 0.00% |  |

TABLE 7

ED$_{50}$ of H58N35-33T1 VLP for inducing the generation of antibodies against HPV33, HPV58 in mice

| Type | Dose (μg) | Total number of mice | Number of mice with positive conversion | Positive conversion rate | ED50 (μg) |
|---|---|---|---|---|---|
| HPV33 | 0.300 | 8 | 7 | 94.74% | 0.043 |
|  | 0.100 | 8 | 6 | 78.57% |  |
|  | 0.033 | 8 | 4 | 41.67% |  |
|  | 0.011 | 8 | 0 | 6.25% |  |
|  | 0.004 | 8 | 1 | 4.35% |  |
| HPV58 | 0.300 | 8 | 8 | 100.00% | 0.019 |
|  | 0.100 | 8 | 8 | 100.00% |  |
|  | 0.033 | 8 | 7 | 88.89% |  |
|  | 0.011 | 8 | 1 | 11.11% |  |
|  | 0.004 | 8 | 0 | 0.00% |  |

TABLE 8

ED$_{50}$ of HPV58N35 VLP for inducing the generation of antibodies against HPV33, HPV58 in mice

| Type | Dose (μg) | Total number of mice | Number of mice with positive conversion | Positive conversion rate | ED$_{50}$ (μg) |
|---|---|---|---|---|---|
| HPV33 | 0.300 | 8 | 0 | 0.00% | >0.3 |
|  | 0.100 | 8 | 0 | 0.00% |  |
|  | 0.033 | 8 | 0 | 0.00% |  |
|  | 0.011 | 8 | 0 | 0.00% |  |
|  | 0.004 | 8 | 0 | 0.00% |  |
| HPV58 | 0.300 | 8 | 8 | 100.00% | 0.006 |
|  | 0.100 | 8 | 8 | 100.00% |  |
|  | 0.033 | 8 | 7 | 94.12% |  |
|  | 0.011 | 8 | 6 | 75.00% |  |
|  | 0.004 | 8 | 3 | 27.27% |  |

The results showed that 5 weeks after vaccination of mice, ED$_{50}$ of H58N35-33T1 VLP for inducing the generation of antibodies against HPV58 in mice was comparable to that of HPV58N35 VLP alone, and was significantly superior to that of HPV33N9 VLP alone; and its ED$_{50}$ for inducing the generation of antibodies against HPV33 in mice was comparable to that of HPV33N9 VLP alone, and was significantly superior to that of HPV58N35 VLP alone. This showed that H58N35-33T1 VLP had good cross-immunogenicity and cross-protection against HPV58 and HPV33.

ED$_{50}$ of H58N35-33T1-52S1 VLP and H58N35-58T1-52S4 VLP 6-week old BalB/c female mice (8 mice) were vaccinated with aluminum adjuvant by single intraperitoneal injection, wherein H58N35-33T1-52S1 VLP or H58N35-58T1-52S4 VLP was used in the Experimental groups (at an immunizing dose of 0.900 μg, 0.300 μg, 0.100 μg, 0.033 μg, 0.011 μg or 0.004 μg); HPV33N9 VLP alone, HPV58N35 VLP alone or HPV52N40 VLP alone (at an immunizing dose of 0.300 μg, 0.100 μg, 0.033 μg, 0.011 μg or 0.004 μg), or a mixture of HPV33N9 VLP, HPV58N35 VLP and HPV52N40 VLP (for each VLP, the immunizing dose was 0.300 μg, 0.100 μg, 0.033 μg, 0.011 μg or 0.004 μg) was used in the Control groups; and the immunizing volume was 1 mL. At Week 5 after vaccination, venous blood was collected from eyeball. Antibodies against HPV in the blood were detected, and by Reed-Muench method (Reed L J M H. A simple method of estimating fifty percent endpoints. Am J Hyg. 1938; 27:493-7), ED$_{50}$ for inducing seroconversion (i.e. inducing the generation of antibodies in mice) was calculated for each sample. The results were shown in Tables 9-14.

TABLE 9

ED$_{50}$ of HPV33N9 VLP for inducing the generation of antibodies against HPV33, HPV58 and HPV52 in mice

| Type | Dose (μg) | Total number of mice | Number of mice with positive conversion | Positive conversion rate | ED50 (μg) |
|---|---|---|---|---|---|
| HPV33 | 0.300 | 8 | 8 | 100.00% | 0.013 |
|  | 0.100 | 8 | 7 | 94.74% |  |
|  | 0.033 | 8 | 6 | 78.57% |  |
|  | 0.011 | 8 | 5 | 45.45% |  |
|  | 0.004 | 8 | 0 | 0.00% |  |
| HPV58 | 0.300 | 8 | 0 | 0.00% | >0.3 |
|  | 0.100 | 8 | 0 | 0.00% |  |
|  | 0.033 | 8 | 0 | 0.00% |  |
|  | 0.011 | 8 | 0 | 0.00% |  |
|  | 0.004 | 8 | 0 | 0.00% |  |
| HPV52 | 0.300 | 8 | 0 | 0.00% | >0.3 |
|  | 0.100 | 8 | 0 | 0.00% |  |
|  | 0.033 | 8 | 0 | 0.00% |  |
|  | 0.011 | 8 | 0 | 0.00% |  |
|  | 0.004 | 8 | 0 | 0.00% |  |

TABLE 10

ED$_{50}$ of HPV58N35 VLP for inducing the generation of antibodies against HPV33, HPV58 and HPV52 in mice

| Type | Dose (μg) | Total number of mice | Number of mice with positive conversion | Positive conversion rate | ED50 (μg) |
|---|---|---|---|---|---|
| HPV33 | 0.300 | 8 | 1 | 12.50% | >0.3 |
|  | 0.100 | 8 | 0 | 0.00% |  |
|  | 0.033 | 8 | 0 | 0.00% |  |
|  | 0.011 | 8 | 0 | 0.00% |  |
|  | 0.004 | 8 | 0 | 0.00% |  |
| HPV58 | 0.300 | 8 | 8 | 100.00% | 0.021 |
|  | 0.100 | 8 | 7 | 93.75% |  |
|  | 0.033 | 8 | 7 | 80.00% |  |
|  | 0.011 | 8 | 1 | 10.00% |  |
|  | 0.004 | 8 | 0 | 0.00% |  |
| HPV52 | 0.300 | 8 | 0 | 0.00% | >0.3 |
|  | 0.100 | 8 | 0 | 0.00% |  |
|  | 0.033 | 8 | 0 | 0.00% |  |
|  | 0.011 | 8 | 0 | 0.00% |  |
|  | 0.004 | 8 | 0 | 0.00% |  |

TABLE 11

ED$_{50}$ of HPV52N40 VLP for inducing the generation of antibodies against HPV33, HPV58 and HPV52 in mice

| Type | Dose (μg) | Total number of mice | Number of mice with positive conversion | Positive conversion rate | ED50 (μg) |
|---|---|---|---|---|---|
| HPV33 | 0.300 | 8 | 0 | 0.00% | >0.3 |
|  | 0.100 | 8 | 0 | 0.00% |  |
|  | 0.033 | 8 | 0 | 0.00% |  |
|  | 0.011 | 8 | 0 | 0.00% |  |
|  | 0.004 | 8 | 0 | 0.00% |  |
| HPV58 | 0.300 | 8 | 0 | 0.00% | >0.3 |
|  | 0.100 | 8 | 0 | 0.00% |  |
|  | 0.033 | 8 | 0 | 0.00% |  |
|  | 0.011 | 8 | 0 | 0.00% |  |
|  | 0.004 | 8 | 0 | 0.00% |  |
| HPV52 | 0.300 | 8 | 8 | 100.00% | 0.046 |
|  | 0.100 | 8 | 7 | 90.91% |  |
|  | 0.033 | 8 | 3 | 33.33% |  |
|  | 0.011 | 8 | 0 | 0.00% |  |
|  | 0.004 | 8 | 0 | 0.00% |  |

TABLE 12

ED$_{50}$ of a mixture of HPV33N9 VLP, HPV58N35 VLP and HPV52N40 VLP for inducing the generation of antibodies against HPV33, HPV58 and HPV52 in mice

| Type | Dose (μg) | Total number of mice | Number of mice with positive conversion | Positive conversion rate | ED50 (μg) |
|---|---|---|---|---|---|
| HPV33 | 0.300 for each VLP | 8 | 6 | 93.33% | 0.009 |
|  | 0.100 for each VLP | 8 | 8 | 91.67% |  |
|  | 0.033 for each VLP | 8 | 6 | 77.78% |  |
|  | 0.011 for each VLP | 8 | 7 | 61.54% |  |
|  | 0.004 for each VLP | 8 | 1 | 7.69% |  |
| HPV58 | 0.300 for each VLP | 8 | 6 | 93.10% | 0.009 |
|  | 0.100 for each VLP | 8 | 8 | 91.30% |  |
|  | 0.033 for each VLP | 8 | 5 | 72.22% |  |
|  | 0.011 for each VLP | 8 | 8 | 61.54% |  |
|  | 0.004 for each VLP | 8 | 0 | 0.00% |  |
| HPV52 | 0.300 for each VLP | 8 | 6 | 92.31% | 0.017 |
|  | 0.100 for each VLP | 8 | 8 | 90.00% |  |
|  | 0.033 for each VLP | 8 | 5 | 66.67% |  |
|  | 0.011 for each VLP | 8 | 5 | 38.46% |  |
|  | 0.004 for each VLP | 8 | 0 | 0.00% |  |

TABLE 13

ED$_{50}$ of H58N35-33T1-52S1 VLP for inducing the generation of antibodies against HPV33, HPV58 and HPV52 in mice

| Type | Dose (μg) | Total number of mice | Number of mice with positive conversion | Positive conversion rate | ED50 (μg) |
|---|---|---|---|---|---|
| HPV33 | 0.900 | 8 | 8 | 100.00% | 0.009 |
|  | 0.300 | 8 | 8 | 100.00% |  |
|  | 0.100 | 8 | 7 | 95.24% |  |
|  | 0.033 | 8 | 5 | 76.47% |  |
|  | 0.011 | 8 | 6 | 57.14% |  |
|  | 0.004 | 8 | 2 | 14.29% |  |
| HPV58 | 0.900 | 8 | 8 | 100.00% | 0.014 |
|  | 0.300 | 8 | 7 | 96.15% |  |
|  | 0.100 | 8 | 7 | 90.00% |  |
|  | 0.033 | 8 | 4 | 64.71% |  |
|  | 0.011 | 8 | 6 | 46.67% |  |
|  | 0.004 | 8 | 1 | 6.25% |  |
| HPV52 | 0.900 | 8 | 7 | 91.67% | 0.341 |
|  | 0.300 | 8 | 4 | 44.44% |  |
|  | 0.100 | 8 | 0 | 0.00% |  |
|  | 0.033 | 8 | 0 | 0.00% |  |
|  | 0.011 | 8 | 0 | 0.00% |  |
|  | 0.004 | 8 | 0 | 0.00% |  |

TABLE 14

ED$_{50}$ of H58N35-33T1-52S4 VLP for inducing the generation of antibodies against HPV33, HPV58 and HPV52 in mice

| Type | Dose (μg) | Total number of mice | Number of mice with positive conversion | Positive conversion rate | ED50 (μg) |
|---|---|---|---|---|---|
| HPV33 | 0.900 | 8 | 8 | 100.00% | 0.065 |
|  | 0.300 | 8 | 8 | 100.00% |  |
|  | 0.100 | 8 | 5 | 70.00% |  |
|  | 0.033 | 8 | 2 | 18.18% |  |
|  | 0.011 | 8 | 0 | 0.00% |  |
|  | 0.004 | 8 | 0 | 0.00% |  |
| HPV58 | 0.900 | 8 | 8 | 100.00% | 0.041 |
|  | 0.300 | 8 | 8 | 100.00% |  |
|  | 0.100 | 8 | 7 | 91.67% |  |
|  | 0.033 | 8 | 3 | 40.00% |  |
|  | 0.011 | 8 | 1 | 7.14% |  |
|  | 0.004 | 8 | 0 | 0.00% |  |

TABLE 14-continued

ED$_{50}$ of H58N35-33T1-52S4 VLP for inducing the generation of antibodies against HPV33, HPV58 and HPV52 in mice

| Type | Dose (µg) | Total number of mice | Number of mice with positive conversion | Positive conversion rate | ED50 (µg) |
|---|---|---|---|---|---|
| HPV52 | 0.900 | 8 | 8 | 100.00% | 0.058 |
|  | 0.300 | 8 | 8 | 100.00% |  |
|  | 0.100 | 8 | 6 | 80.00% |  |
|  | 0.033 | 8 | 2 | 20.00% |  |
|  | 0.011 | 8 | 0 | 0.00% |  |
|  | 0.004 | 8 | 0 | 0.00% |  |

The results showed that 5 weeks after vaccination of mice, ED$_{50}$ of H58N35-33T1-52S1 VLP and H58N35-33T1-52S4 VLP for inducing the generation of antibodies against HPV58 in mice was comparable to that of HPV58N35 VLP alone and of a mixture of HPV58N35 VLP, HPV33N9 VLP and HPV52N40 VLP, and was significantly superior to that of HPV33N9 VLP alone and HPV52N40 VLP alone; and their ED$_{50}$ for inducing the generation of antibodies against HPV33 in mice was comparable to that of HPV33N9 VLP alone and of a mixture of HPV58N35 VLP, HPV33N9 VLP and HPV52N40 VLP, and was significantly superior to that of HPV58N35 VLP alone and of HPV52N40 VLP alone; and their ED$_{50}$ for inducing the generation of antibodies against HPV52 in mice was comparable to that of HPV52N40 VLP alone and of a mixture of HPV58N35 VLP, HPV33N9 VLP and HPV52N40 VLP, and was significantly superior to that of HPV33N9 VLP alone and of HPV58N35 VLP alone. This showed that H33N9-58T5-52S2 VLP and H33N9-58T5-52S4 VLP had good cross-immunogenicity and cross-protection against HPV58, HPV33 and HPV52.

Evaluation of Neutralizing Antibody Titer in Serum of Mice Vaccinated with H58N35-33T1 VLP In this experiment, vaccination schedule was shown in Table 15. All the mice (6-week old BalB/c female mice) were divided into 4 groups: Freund's adjuvant group (at an immunizing dose of 1 µg, using Freund's adjuvant), Aluminum adjuvant group 1 (at an immunizing dose of 10 µg, using aluminum adjuvant), Aluminum adjuvant group 2 (at an immunizing dose of 1 µg, using aluminum adjuvant), and Aluminum adjuvant group 3 (at an immunizing dose of 0.1 µg, using aluminum adjuvant). Each group was further divided into 3 subgroups. The Control subgroups 1 and 2 were vaccinated with HPV33N9 VLP alone and HPV58N35 VLP alone, respectively, and the Experimental subgroup was vaccinated with H58N35-33T1 VLP.

In Freund's adjuvant group, 6 mice/subgroup were vaccinated by subcutaneous injection, at an immunizing dose of 1 µg, and an injection volume of 200 µl. In Aluminum adjuvant groups 1-3, 6 mice/subgroup were vaccinated by intraperitoneal injection, at an immunizing dose 10 µg, 1 µg, and 0.1 µg, respectively, and an injection volume of 1 mL. All the mice were subjected to the first vaccination at Week 0, and then subjected to the booster vaccination at Weeks 2 and 4, respectively. At Week 8, blood sample was collected via orbital bleeding, and the titers of antibodies against HPV58 and HPV33 in serum were analyzed. The analysis results were shown in FIGS. 8A-8D. The results showed that H58N35-33T1 VLP could induce the generation of high-titer neutralizing antibodies against HPV58 in mice, and its protective effect was comparable to that of HPV58N35 VLP alone at the same dose, was significantly superior to that of HPV33N9 VLP alone at the same dose; and it could induce the generation of high-titer neutralizing antibodies against HPV33 in mice, and its protective effect was comparable to that of HPV33N9 VLP alone at the same dose, and was significantly superior to that of HPV58N35 VLP alone at the same dose. This showed that H58N35-33T1 VLP had good cross-immunogenicity and cross-protection against HPV58 and HPV33.

TABLE 15

Vaccination schedule

| Group | Antigen for vaccination | Adjuvant | Immunizing dose | Number | Vaccination procedure (week) |
|---|---|---|---|---|---|
| Freund's adjuvant group | HPV58N35 VLP | Freund's adjuvant | 1 µg | 6 | 0, 2, 4 |
|  | HPV33N9 VLP | Freund's adjuvant | 1 µg | 6 | 0, 2, 4 |
|  | H58N35-33T1 VLP | Freund's adjuvant | 1 µg | 6 | 0, 2, 4 |
| Aluminum adjuvant group 1 | HPV58N35 VLP | aluminum adjuvant | 10 µg | 6 | 0, 2, 4 |
|  | HPV33N9 VLP | aluminum adjuvant | 10 µg | 6 | 0, 2, 4 |
|  | H58N35-33T1 VLP | aluminum adjuvant | 10 µg | 6 | 0, 2, 4 |
| Aluminum adjuvant group 2 | HPV58N35 VLP | aluminum adjuvant | 1 µg | 6 | 0, 2, 4 |
|  | HPV33N9 VLP | aluminum adjuvant | 1 µg | 6 | 0, 2, 4 |
|  | H58N35-33T1 VLP | aluminum adjuvant | 1 µg | 6 | 0, 2, 4 |
| Aluminum adjuvant group 3 | HPV58N35 VLP | aluminum adjuvant | 0.1 µg | 6 | 0, 2, 4 |
|  | HPV33N9 VLP | aluminum adjuvant | 0.1 µg | 6 | 0, 2, 4 |
|  | H58N35-33T1 VLP | aluminum adjuvant | 0.1 µg | 6 | 0, 2, 4 |

Evaluation of Neutralizing Antibody Titer in Serum of Mice Vaccinated with H58N35-33T1-52S1 VLP or H58N35-33T1-52S4 VLP In this experiment, vaccination schedule was shown in Table 16. All the mice (6-week old BalB/c female mice) were divided into 3 groups: Aluminum adjuvant group 1 (at an immunizing dose of 10 μg, using aluminum adjuvant), Aluminum adjuvant group 2 (at an immunizing dose of 1 μg, using aluminum adjuvant), and Aluminum adjuvant group 3 (at an immunizing dose of 0.1 μg, using aluminum adjuvant). Each group was further divided into 6 subgroups. The Control subgroups 1, 2 and 3 were vaccinated with HPV58N35 VLP alone, HPV33N9 VLP alone and HPV52N40 VLP alone, respectively; the Control subgroup 4 was vaccinated with a mixture of HPV58N35 VLP, HPV33N9 VLP and HPV52N40 VLP; and the Experimental subgroups 1 and 2 were vaccinated with H58N35-33T1-52S1 VLP alone and H58N35-33T1-52S4 VLP alone, respectively.

Figure 8A:
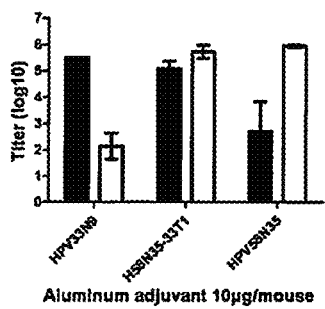
FIGS. 8A-8D show the result of neutralizing antibody titer in mouse serum after vaccination of mice with H58N35-33T1 VLP.
Figure 8B:
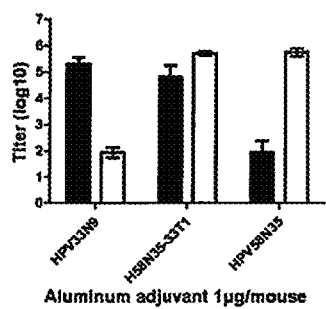
Figure 8C:
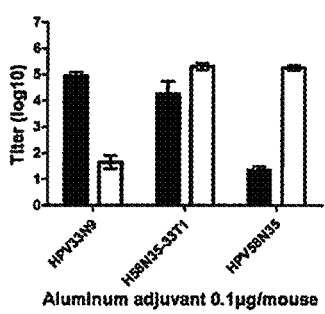
Figure 8D:
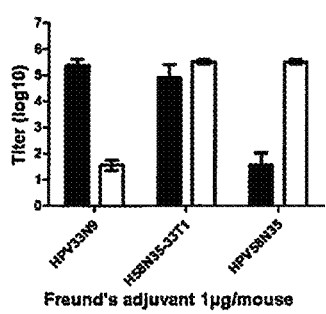
Figure 8E:
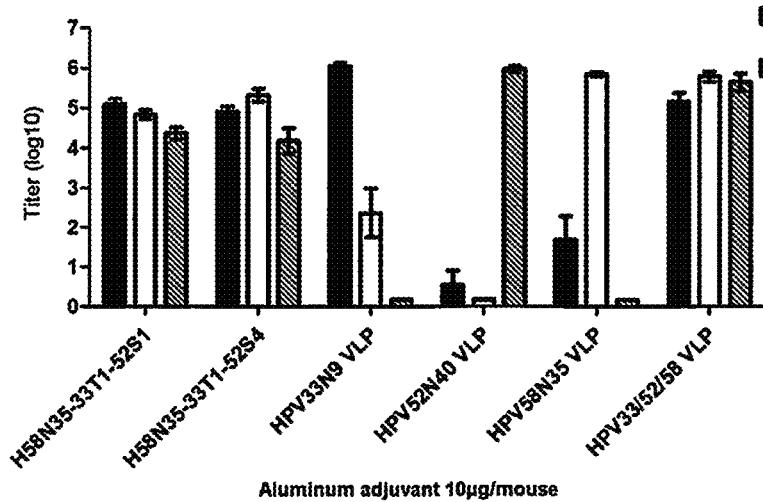
FIG. 8E-8G show the result of neutralizing antibody titer in mouse serum after vaccination of mice with H58N35-33T1-52S1 VLP or H58N35-33T1-52S4 VLP.
Figure 8F:
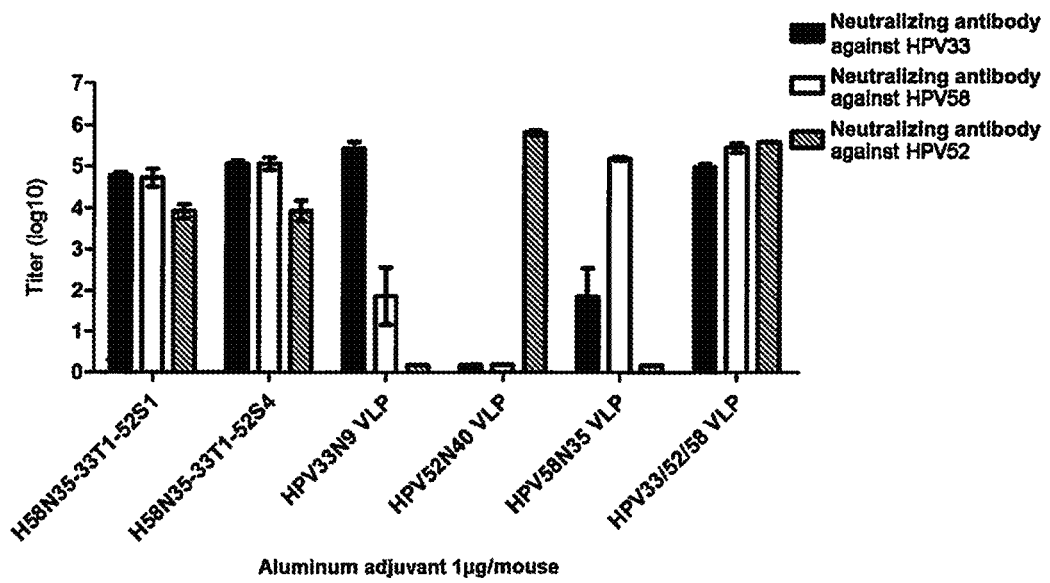
Figure 8G:
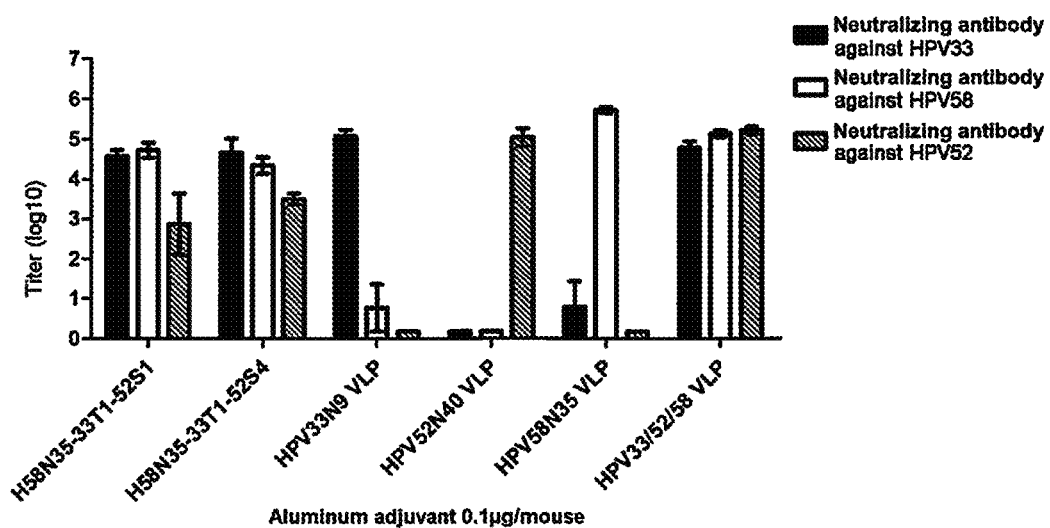

In Aluminum adjuvant groups 1-3, 6 mice/subgroup were vaccinated by intraperitoneal injection, at an immunizing dose of 10 μg, 1 μg, and 0.1 μg, respectively, and an injection volume of 1 mL. All the mice were subjected to the first vaccination at Week 0, and then subjected to the booster vaccination at Weeks 2 and 4, respectively. At Week 8, blood sample was collected via orbital bleeding, and the titers of antibodies against HPV58, HPV33 and HPV52 in serum were analyzed. The analysis results were shown in FIGS. 8E-8G. The results showed that H58N35-33T1-52S1 VLP and H58N35-33T1-52S4 VLP could induce the generation of high-titer neutralizing antibodies against HPV58 in mice, and their protective effect was comparable to that of HPV58N35 VLP alone and that of a mixture of HPV58N35 VLP, HPV33N9 VLP and HPV52N40 VLP at the same dose, and was significantly superior to that of HPV33N9 VLP alone or HPV52N40 VLP alone at the same dose; and they could induce the generation of high-titer neutralizing antibodies against HPV33 in mice, and their protective effect was comparable to that of HPV33N9 VLP alone and that of a mixture of HPV58N35 VLP, HPV33N9 VLP and HPV52N40 VLP at the same dose, and was significantly superior to that of HPV58N35 VLP alone or HPV52N40 VLP alone at the same dose; and they could induce the generation of high-titer neutralizing antibodies against HPV52 in mice, and their protective effect was slightly weaker than that of HPV52N40 VLP alone and that of a mixture of HPV58N35 VLP, HPV33N9 VLP and HPV52N40 VLP at the same dose, but was significantly superior to that of HPV58N35 VLP alone or HPV33N9 VLP alone at the same dose. This showed that H58N35-33T1-52S1 VLP and H58N35-33T1-52S4 VLP had good cross-immunogenicity and cross-protection against HPV58, HPV33 and HPV52.

TABLE 16

Vaccination schedule

| Group | Antigen for vaccination | Adjuvant | Immunizing dose | Number | Vaccination procedure (week) |
|---|---|---|---|---|---|
| Aluminum adjuvant group 1 | HPV33N9 VLP | aluminum adjuvant | 10 μg | 6 | 0, 2, 4 |
| | HPV58N35 VLP | aluminum adjuvant | 10 μg | 6 | 0, 2, 4 |
| | HPV52N40 VLP | aluminum adjuvant | 10 μg | 6 | 0, 2, 4 |
| | HPV58/HPV33/HPV52 VLP | aluminum adjuvant | 10 μg for each VLP | 6 | 0, 2, 4 |
| | H58N35-33T1-52S1 VLP | aluminum adjuvant | 10 μg | 6 | 0, 2, 4 |
| | H58N35-33T1-52S4 VLP | aluminum adjuvant | 10 μg | 6 | 0, 2, 4 |
| Aluminum adjuvant group 2 | HPV33N9 VLP | aluminum adjuvant | 1 μg | 6 | 0, 2, 4 |
| | HPV58N35 VLP | aluminum adjuvant | 1 μg | 6 | 0, 2, 4 |
| | HPV52N40 VLP | aluminum adjuvant | 1 μg | 6 | 0, 2, 4 |
| | HPV58/HPV33/HPV52 VLP | aluminum adjuvant | 1 μg for each VLP | 6 | 0, 2, 4 |
| | H58N35-33T1-52S1 VLP | aluminum adjuvant | 1 μg | 6 | 0, 2, 4 |
| | H58N35-33T1-52S4 VLP | aluminum adjuvant | 1 μg | 6 | 0, 2, 4 |
| Aluminum adjuvant group 3 | HPV33N9 VLP | aluminum adjuvant | 0.1 μg | 6 | 0, 2, 4 |
| | HPV58N35 VLP | aluminum adjuvant | 0.1 μg | 6 | 0, 2, 4 |
| | HPV52N40 VLP | aluminum adjuvant | 0.1 μg | 6 | 0, 2, 4 |
| | HPV58/HPV33/HPV52 VLP | aluminum adjuvant | 0.1 μg for each VLP | 6 | 0, 2, 4 |
| | H58N35-33T1-52S1 VLP | aluminum adjuvant | 0.1 μg | 6 | 0, 2, 4 |
| | H58N35-33T1-52S4 VLP | aluminum adjuvant | 0.1 μg | 6 | 0, 2, 4 |

EXAMPLE 6: EVALUATION OF IMMUNE PROTECTION OF H58N35-33T1-52S4 VLP IN CYNOMOLGUS MONKEY

Figure 9:
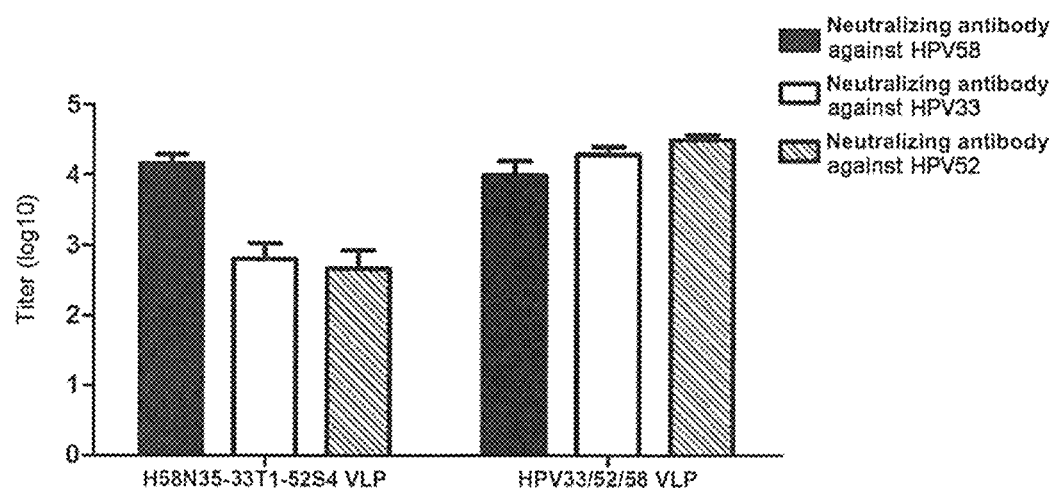
FIG. 9 shows the evaluation result of neutralizing antibodies in cynomolgus monkey serum after vaccination of cynomolgus monkey with H58N35-33T1-52S4 VLP. The result showed that H58N35-33T1-52S4 VLP could induce the generation of high-titer neutralizing antibodies against HPV58, HPV33 and HPV52 in cynomolgus monkey, and its protective effect was comparable to that of a mixture of HPV58N35 VLP, HPV33N9 VLP and HPV52N40 VLP at the same dose. This showed that H58N35-33T1-52S4 VLP had good cross-immunogenicity against HPV58, HPV33 and HPV52, and could induce good cross-protection against HPV58, HPV33 and HPV52 in primate.

This experiment was carried out in the Yunnan Key Laboratory of Primate Biomedical Research. Vaccination schedule was shown in Table 17. 14 cynomolgus monkeys were randomly divided into two groups: the Control group was vaccinated with a mixture of HPV58N35 VLP, HPV33N9 VLP and HPV52N40 VLP, at a dose of 5 µg for each VLP, and an injection volume of 1 mL; the Experimental group was vaccinated with H58N35-33T1-52S4 VLP alone, at a dose of 5 µg, and an injection volume of 1 mL. The adjuvant used was aluminum adjuvant, and the cynomolgus monkeys were vaccinated by intramuscular injection. All the cynomolgus monkeys were subjected to the first vaccination at Week 0, and then subjected to the booster vaccination at Week 8. Blood was collected from cynomolgus monkeys at Week 10, and the titers of antibodies against HPV58, HPV33 and HPV52 in serum were analyzed. The analysis result was shown in FIG. 9. The result showed that H58N35-33T1-52S4 VLP alone could induce the generation of high-titer neutralizing antibodies against HPV58, HPV33 and HPV52 in cynomolgus monkeys, and its protective effect was comparable to that of a mixture of HPV58N35 VLP, HPV33N9 VLP and HPV52N40 VLP at the same dose. This showed that H58N35-33T1-52S4 VLP had good cross-immunogenicity against HPV58, HPV33 and HPV52, and could induce good cross-protection against HPV58, HPV33 and HPV52 in primates.

TABLE 17

Vaccination schedule

| Antigen for vaccination | Adjuvant | Immunizing dose | Number | Vaccination procedure (week) |
|---|---|---|---|---|
| H58N35-33T1-52S4 VLP | aluminum adjuvant | 5 µg | 7 | 0, 8 |
| HPV58/HPV33/HPV52 VLP | aluminum adjuvant | 5 µg for each VLP | 7 | 0, 8 |

EXAMPLE 7: RECONSTRUCTION OF THREE-DIMENSIONAL STRUCTURES OF H58N35-33T1 VLP AND H58N35-33T1-52S4 VLP

Figure 10A:
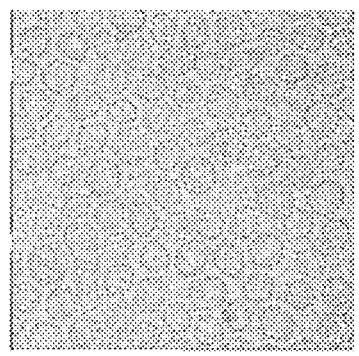
FIGS. 10A-10D show the cryo-electron microscopy (cryoEM) photographs and the reconstructed three-dimensional structures of H58N35-33T1 VLP and H58N35-33T1-52S4 VLP, respectively.
Figure 10B:
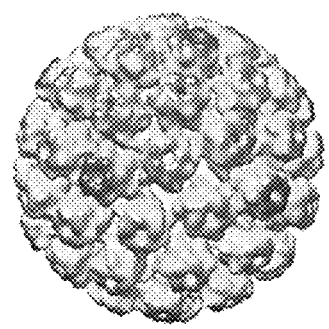
Figure 10C:
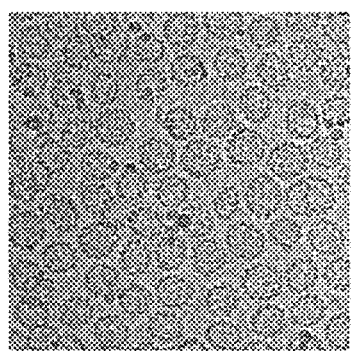
Figure 10D:
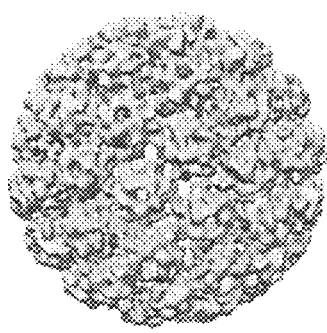

The three-dimensional structures of H58N35-33T1 VLP and H58N35-33T1-52S4 VLP were reconstructed by three-dimensional structure reconstruction experiment using cryo-electron microscopy (cryoEM) (Wolf M, Garcea R L, Grigorieff N. et al. Proc Natl Acad Sci USA. (2010), 107(14): 6298-303). In brief, in the cryo-electron microscopy (cryoEM) photograph of H58N35-33T1 VLP (FIG. 10A), 581 particles with an uniform size and a diameter of greater than 50 nm were selected for computer overlapping and structural reconstruction, thereby obtaining the three-dimensional structure of H58N35-33T1 VLP. The three-dimensional structure obtained was shown in FIG. 10B (at a resolution of 22 Å). In addition, in the cryo-electron microscopy (cryoEM) photograph of H58N35-33T1-52S4 VLP (FIG. 10C), 220 particles with an uniform size and a diameter of greater than 50 nm were selected for computer overlapping and structural reconstruction, thereby obtaining the three-dimensional structure of H58N35-33T1-52S4 VLP. The three-dimensional structure obtained was shown in FIG. 10D (at a resolution of 18 Å). The results showed that both H58N35-33T1 VLP and H58N35-33T1-52S4 VLP had a T=7 icosahedral structure (h=1, k=2) consisting of 72 capsomers (morphological subunit, pentamer). Unlike conventional icosahedral viral capsids consistent with quasi-equivalence principle, all the constitutive subunits in the structures of H58N35-33T1 VLP and H58N35-33T1-52S4 VLP were pentamers, without hexamer. Moreover, said two VLPs had an external diameter of about 60 nm. These were similar to the three-dimensional structures of the previously reported natural HPV viral particles and the HPV VLP prepared by eukaryotic expression system (e.g. poxvirus expression system) (Baker T S, Newcomb W W, Olson N H. et al. Biophys J. (1991), 60(6): 1445-1456. Hagensee M E, Olson N H, Baker T S, et al. J Virol. (1994), 68(7):4503-4505. Buck C B, Cheng N, Thompson C D. et al. J Virol. (2008), 82(11): 5190-7).

Although the specific embodiments of the present invention have been described in details, those skilled in the art would understand that, according to the teachings disclosed in the specification, various modifications and changes can be made thereto, and that such modifications and changes are within the scope of the present invention. The scope of the present invention is given by the appended claims and any equivalents thereof.

The invention claimed is:

1. A mutated HPV58 L1 protein, wherein as compared with a wild type HPV58 L1 protein, the mutated HPV58 L1 protein has the following mutations:
   (1) N-terminal truncation of 5-70 amino acids; and
   (2)(a) substitution of amino acid residues at positions 80-87 of the wild type HPV58 L1 protein with amino acid residues at the corresponding positions of the wild-type HPV33 L1 protein; or
   (2)(b) substitution of amino acid residues at positions 376-383 of the wild type HPV58 L1 protein with amino acid residues at the corresponding positions of the wild-type HPV33 L1 protein;
   wherein said wild type HPV58 L1 protein has an amino acid sequence as set forth in SEQ ID NO: 1 or a sequence having 95% or greater identity to SEQ ID NO: 1; and wherein said wild type HPV33 L1 protein has an amino acid sequence as set forth in SEQ ID NO: 2 or a sequence having 95% or greater identity to SEQ ID NO: 2.

2. An isolated nucleic acid, encoding the mutated HPV58 L1 protein according to claim 1.

3. A vector comprising the isolated nucleic acid according to claim 2.

4. An isolated host cell comprising the isolated nucleic acid according to claim 2 and/or a vector comprising the isolated nucleic acid.

5. A HPV virus-like particle, comprising or consisting of the mutated HPV58 L1 protein according to claim 1.

6. A pharmaceutical composition or vaccine, comprising the HPV virus-like particle according to claim 5, and a pharmaceutically acceptable carrier and/or excipient.

7. A method for preparing the mutated HPV58 L1 protein according to claim 1, comprising expressing the mutated HPV58 L1 protein in a host cell, and then recovering the mutated HPV58 L1 protein from a culture of the host cell.

8. A method for preparing a vaccine, comprising combining the HPV virus-like particle according to claim 5 with a pharmaceutically acceptable carrier and/or excipient.

9. A method for preventing HPV infection or a disease caused by HPV infection, comprising administering to a subject a prophylactically effective amount of the HPV virus-like particle according to claim 5 or a pharmaceutical composition or vaccine comprising the HPV virus-like particle and a pharmaceutically acceptable carrier and/or excipient.

10. The mutated HPV58 L1 protein according to claim 1, wherein the mutated HPV58 L1 protein is characterized by one or more of the following items:
   (i) the mutated HPV58 L1 protein has 5, 15, 27, 35, 40, 60 or 70 amino acids truncated at N-terminal, as compared with the wild type HPV58 L1 protein;
   (ii) the amino acid residues at the corresponding positions as described in claim 1 section (2)(a) are amino acid residues at positions 54-61 of the wild type HPV33 L1 protein; and
   (iii) the amino acid residues at the corresponding positions as described in claim 1 section (2)(b) are amino acid residues at positions 350-357 of the wild type HPV33 L1 protein.

11. The mutated HPV58 L1 protein according to claim 1, wherein the mutated HPV58 L1 protein has an amino acid sequence selected from the group consisting of: SEQ ID NOs: 4 and 10.

12. The method according to claim 7, wherein the host cell is E. coli.

13. The method according to claim 9, wherein: the HPV infection is HPV58 infection and/or HPV33 infection; and/ or, the disease caused by HPV infection is selected from the group consisting of cervical cancer and condyloma acuminatum.

14. A mutated HPV58 L1 protein, wherein as compared with a wild type HPV58 L1 protein, the mutated HPV58 L1 protein has the following mutations:
   (1) N-terminal truncation of 5-70 amino acids; and
   (2)(a) substitution of amino acid residues at positions 80-87 of the wild type HPV58 L1 protein with amino acid residues at the corresponding positions of a wild-type HPV33 L1 protein; and
   (3)(a) substitution of amino acid residues at positions 375-383 of the wild type HPV58 L1 protein with the amino acid residues at the corresponding positions of a wild type HPV52 L1 protein; or
   (3)(b) substitution of amino acid residues at positions 144-168 of the wild type HPV58 L1 protein with amino acid residues at the corresponding positions of a wild type HPV52 L1 protein;
   wherein said wild type HPV58 L1 protein has an amino acid sequence as set forth in SEQ ID NO: 1 or a sequence having 95% or greater identity to SEQ ID NO:1; wherein said wild type HPV33 L1 protein has an amino acid sequence as set forth in SEQ ID NO: 2 or a sequence having 95% or greater identity to SEQ ID NO:2; and wherein said wild type HPV52 L1 protein has an amino acid sequence as set forth in SEQ ID NO: 3 or a sequence having 95% or greater identity to SEQ ID NO:3.

15. The mutated HPV58 L1 protein according to claim 14, wherein the mutated HPV58 L1 protein comprises one or more of the following items:
   (i) the mutated HPV58 L1 protein has 5, 15, 27, 35, 40, 60 or 70 amino acids truncated at N-terminus, as compared with a wild type HPV58 L1 protein;
   (ii) the amino acid residues at the corresponding positions as described in claim 14, section (2) are amino acid residues at positions 54-61 of the wild type HPV33 L1 protein;
   (iii) the amino acid residues at the corresponding positions as described in claim 14, section (3)(a) are amino acid residues at positions 380-388 of a wild type HPV52 L1 protein; and
   (iv) the amino acid residues at the corresponding positions as described in in claim 14, section (3)(b) are amino acid residues at positions 146-170 of a wild type HPV52 L1 protein.

16. The mutated HPV58 L1 protein according to claim 14, wherein the mutated HPV58 L1 protein has an amino acid sequence selected from the group consisting of: SEQ ID NOs: 11 and 14.

17. An isolated nucleic acid, encoding the mutated HPV58 L1 protein according to claim 14.

18. A vector comprising the isolated nucleic acid according to claim 17.

19. An isolated host cell comprising the isolated nucleic acid according to claim 17 and/or a vector comprising the isolated nucleic acid.

20. A HPV virus-like particle, comprising or consisting of the mutated HPV58 L1 protein according to claim 14.

21. A pharmaceutical composition or vaccine, comprising the HPV virus-like particle according to claim 20, and a pharmaceutically acceptable carrier and/or excipient.

22. A method for preparing the mutated HPV58 L1 protein according to claim 14, comprising expressing the mutated HPV58 L1 protein in a host cell, and then recovering the mutated HPV58 L1 protein from a culture of the host cell.

23. The method according to claim 22, wherein the host cell is *E. coli*.

24. A method for preparing a vaccine, comprising combining the HPV virus like particle according to claim 20 with a pharmaceutically acceptable carrier and/or excipient.

25. A method for preventing HPV infection or a disease caused by HPV infection, comprising administering to a subject a prophylactically effective amount of the HPV virus-like particle according to claim 20 or a pharmaceutical composition or vaccine comprising the HPV virus-like particle and a pharmaceutically acceptable carrier and/or excipient.

26. The method according to claim 25, wherein the HPV infection is selected from one or more of the following: HPV58 infection, HPV33 infection and HPV52 infection; and/or, the disease caused by HPV infection is selected from the group consisting of cervical cancer and condyloma acuminatum.

* * * * *

SEQUENCE LISTING

<160> NUMBER OF SEQ ID NOS: 62

<210> SEQ ID NO 1
<211> LENGTH: 524
<212> TYPE: PRT
<213> ORGANISM: Artificial Sequence
<220> FEATURE:
<223> OTHER INFORMATION: HPV 58

<400> SEQUENCE: 1

```
Met Val Leu Ile Leu Cys Cys Thr Leu Ala Ile Leu Phe Cys Val Ala
1               5                   10                  15

Asp Val Asn Val Phe His Ile Phe Leu Gln Met Ser Val Trp Arg Pro
                20                  25                  30

Ser Glu Ala Thr Val Tyr Leu Pro Pro Val Pro Val Ser Lys Val Val
            35                  40                  45

Ser Thr Asp Glu Tyr Val Ser Arg Thr Ser Ile Tyr Tyr Tyr Ala Gly
50                  55                  60

Ser Ser Arg Leu Leu Ala Val Gly Asn Pro Tyr Phe Ser Ile Lys Ser
65                  70                  75                  80

Pro Asn Asn Asn Lys Lys Val Leu Val Pro Lys Val Ser Gly Leu Gln
                85                  90                  95

Tyr Arg Val Phe Arg Val Arg Leu Pro Asp Pro Asn Lys Phe Gly Phe
            100                 105                 110

Pro Asp Thr Ser Phe Tyr Asn Pro Asp Thr Gln Arg Leu Val Trp Ala
        115                 120                 125

Cys Val Gly Leu Glu Ile Gly Arg Gly Gln Pro Leu Gly Val Gly Val
130                 135                 140

Ser Gly His Pro Tyr Leu Asn Lys Phe Asp Asp Thr Glu Thr Ser Asn
145                 150                 155                 160

Arg Tyr Pro Ala Gln Pro Gly Ser Asp Asn Arg Glu Cys Leu Ser Met
                165                 170                 175

Asp Tyr Lys Gln Thr Gln Leu Cys Leu Ile Gly Cys Lys Pro Pro Thr
            180                 185                 190

Gly Glu His Trp Gly Lys Gly Val Ala Cys Asn Asn Asn Ala Ala Ala
        195                 200                 205

Thr Asp Cys Pro Pro Leu Glu Leu Phe Asn Ser Ile Ile Glu Asp Gly
210                 215                 220

Asp Met Val Asp Thr Gly Phe Gly Cys Met Asp Phe Gly Thr Leu Gln
225                 230                 235                 240

Ala Asn Lys Ser Asp Val Pro Ile Asp Ile Cys Asn Ser Thr Cys Lys
                245                 250                 255

Tyr Pro Asp Tyr Leu Lys Met Ala Ser Glu Pro Tyr Gly Asp Ser Leu
            260                 265                 270

Phe Phe Phe Leu Arg Arg Glu Gln Met Phe Val Arg His Phe Phe Asn
        275                 280                 285

Arg Ala Gly Lys Leu Gly Glu Ala Val Pro Asp Asp Leu Tyr Ile Lys
290                 295                 300

Gly Ser Gly Asn Thr Ala Val Ile Gln Ser Ser Ala Phe Phe Pro Thr
305                 310                 315                 320

Pro Ser Gly Ser Ile Val Thr Ser Glu Ser Gln Leu Phe Asn Lys Pro
                325                 330                 335

Tyr Trp Leu Gln Arg Ala Gln Gly His Asn Asn Gly Ile Cys Trp Gly
            340                 345                 350

Asn Gln Leu Phe Val Thr Val Val Asp Thr Thr Arg Ser Thr Asn Met
```

-continued

```
                    355                 360                 365
Thr Leu Cys Thr Glu Val Thr Lys Glu Gly Thr Tyr Lys Asn Asp Asn
370                                 375                 380

Phe Lys Glu Tyr Val Arg His Val Glu Glu Tyr Asp Leu Gln Phe Val
385                         390                 395                 400

Phe Gln Leu Cys Lys Ile Thr Leu Thr Ala Glu Ile Met Thr Tyr Ile
                    405                 410                 415

His Thr Met Asp Ser Asn Ile Leu Glu Asp Trp Gln Phe Gly Leu Thr
                420                 425                 430

Pro Pro Pro Ser Ala Ser Leu Gln Asp Thr Tyr Arg Phe Val Thr Ser
                435                 440                 445

Gln Ala Ile Thr Cys Gln Lys Thr Ala Pro Lys Glu Lys Glu Asp
            450                 455                 460

Pro Leu Asn Lys Tyr Thr Phe Trp Glu Val Asn Leu Lys Glu Lys Phe
465                 470                 475                 480

Ser Ala Asp Leu Asp Gln Phe Pro Leu Gly Arg Lys Phe Leu Leu Gln
                485                 490                 495

Ser Gly Leu Lys Ala Lys Pro Arg Leu Lys Arg Ser Ala Pro Thr Thr
                500                 505                 510

Arg Ala Pro Ser Thr Lys Arg Lys Lys Val Lys Lys
                515                 520
```

<210> SEQ ID NO 2
<211> LENGTH: 499
<212> TYPE: PRT
<213> ORGANISM: Artificial Sequence
<220> FEATURE:
<223> OTHER INFORMATION: HPV 33

<400> SEQUENCE: 2

```
Met Ser Val Trp Arg Pro Ser Glu Ala Thr Val Tyr Leu Pro Pro Val
1               5                   10                  15

Pro Val Ser Lys Val Val Ser Thr Asp Glu Tyr Val Ser Arg Thr Ser
                20                  25                  30

Ile Tyr Tyr Tyr Ala Gly Ser Ser Arg Leu Leu Ala Val Gly His Pro
            35                  40                  45

Tyr Phe Ser Ile Lys Asn Pro Thr Asn Ala Lys Lys Leu Leu Val Pro
        50                  55                  60

Lys Val Ser Gly Leu Gln Tyr Arg Val Phe Arg Val Arg Leu Pro Asp
65                  70                  75                  80

Pro Asn Lys Phe Gly Phe Pro Asp Thr Ser Phe Tyr Asn Pro Asp Thr
                85                  90                  95

Gln Arg Leu Val Trp Ala Cys Val Gly Leu Glu Ile Gly Arg Gly Gln
            100                 105                 110

Pro Leu Gly Val Gly Ile Ser Gly His Pro Leu Leu Asn Lys Phe Asp
        115                 120                 125

Asp Thr Glu Thr Gly Asn Lys Tyr Pro Gly Gln Pro Gly Ala Asp Asn
    130                 135                 140

Arg Glu Cys Leu Ser Met Asp Tyr Lys Gln Thr Gln Leu Cys Leu Leu
145                 150                 155                 160

Gly Cys Lys Pro Pro Thr Gly Glu His Trp Gly Lys Gly Val Ala Cys
                165                 170                 175

Thr Asn Ala Ala Pro Ala Asn Asp Cys Pro Pro Leu Glu Leu Ile Asn
            180                 185                 190

Thr Ile Ile Glu Asp Gly Asp Met Val Asp Thr Gly Phe Gly Cys Met
```

```
                195                 200                 205
Asp Phe Lys Thr Leu Gln Ala Asn Lys Ser Asp Val Pro Ile Asp Ile
210                 215                 220

Cys Gly Ser Thr Cys Lys Tyr Pro Asp Tyr Leu Lys Met Thr Ser Glu
225                 230                 235                 240

Pro Tyr Gly Asp Ser Leu Phe Phe Phe Leu Arg Arg Glu Gln Met Phe
                245                 250                 255

Val Arg His Phe Phe Asn Arg Ala Gly Thr Leu Gly Glu Ala Val Pro
                260                 265                 270

Asp Asp Leu Tyr Ile Lys Gly Ser Gly Thr Thr Ala Ser Ile Gln Ser
                275                 280                 285

Ser Ala Phe Phe Pro Thr Pro Ser Gly Ser Met Val Thr Ser Glu Ser
290                 295                 300

Gln Leu Phe Asn Lys Pro Tyr Trp Leu Gln Arg Ala Gln Gly His Asn
305                 310                 315                 320

Asn Gly Ile Cys Trp Gly Asn Gln Val Phe Val Thr Val Val Asp Thr
                325                 330                 335

Thr Arg Ser Thr Asn Met Thr Leu Cys Thr Gln Val Thr Ser Asp Ser
                340                 345                 350

Thr Tyr Lys Asn Glu Asn Phe Lys Glu Tyr Ile Arg His Val Glu Glu
                355                 360                 365

Tyr Asp Leu Gln Phe Val Phe Gln Leu Cys Lys Val Thr Leu Thr Ala
                370                 375                 380

Glu Val Met Thr Tyr Ile His Ala Met Asn Pro Asp Ile Leu Glu Asp
385                 390                 395                 400

Trp Gln Phe Gly Leu Thr Pro Pro Ser Ala Ser Leu Gln Asp Thr
                405                 410                 415

Tyr Arg Phe Val Thr Ser Gln Ala Ile Thr Cys Gln Lys Thr Val Pro
                420                 425                 430

Pro Lys Glu Lys Glu Asp Pro Leu Gly Lys Tyr Thr Phe Trp Glu Val
                435                 440                 445

Asp Leu Lys Glu Lys Phe Ser Ala Asp Leu Asp Gln Phe Pro Leu Gly
450                 455                 460

Arg Lys Phe Leu Leu Gln Ala Gly Leu Lys Ala Lys Pro Lys Leu Lys
465                 470                 475                 480

Arg Ala Ala Pro Thr Ser Thr Arg Thr Ser Ser Ala Lys Arg Lys Lys
                485                 490                 495

Val Lys Lys

<210> SEQ ID NO 3
<211> LENGTH: 529
<212> TYPE: PRT
<213> ORGANISM: Artificial Sequence
<220> FEATURE:
<223> OTHER INFORMATION: HPV 52

<400> SEQUENCE: 3

Met Val Gln Ile Leu Phe Tyr Ile Leu Val Ile Phe Tyr Tyr Val Ala
1               5                   10                  15

Gly Val Asn Val Phe His Ile Phe Leu Gln Met Ser Val Trp Arg Pro
                20                  25                  30

Ser Glu Ala Thr Val Tyr Leu Pro Pro Val Pro Val Ser Lys Val Val
                35                  40                  45

Ser Thr Asp Glu Tyr Val Ser Arg Thr Ser Ile Tyr Tyr Tyr Ala Gly
                50                  55                  60
```

-continued

```
Ser Ser Arg Leu Leu Thr Val Gly His Pro Tyr Phe Ser Ile Lys Asn
 65                  70                  75                  80

Thr Ser Ser Gly Asn Gly Lys Lys Val Leu Val Pro Lys Val Ser Gly
                 85                  90                  95

Leu Gln Tyr Arg Val Phe Arg Ile Lys Leu Pro Asp Pro Asn Lys Phe
            100                 105                 110

Gly Phe Pro Asp Thr Ser Phe Tyr Asn Pro Glu Thr Gln Arg Leu Val
        115                 120                 125

Trp Ala Cys Thr Gly Leu Glu Ile Gly Arg Gly Gln Pro Leu Gly Val
    130                 135                 140

Gly Ile Ser Gly His Pro Leu Leu Asn Lys Phe Asp Asp Thr Glu Thr
145                 150                 155                 160

Ser Asn Lys Tyr Ala Gly Lys Pro Gly Ile Asp Asn Arg Glu Cys Leu
                165                 170                 175

Ser Met Asp Tyr Lys Gln Thr Gln Leu Cys Ile Leu Gly Cys Lys Pro
            180                 185                 190

Pro Ile Gly Glu His Trp Gly Lys Gly Thr Pro Cys Asn Asn Asn Ser
        195                 200                 205

Gly Asn Pro Gly Asp Cys Pro Pro Leu Gln Leu Ile Asn Ser Val Ile
210                 215                 220

Gln Asp Gly Asp Met Val Asp Thr Gly Phe Gly Cys Met Asp Phe Asn
225                 230                 235                 240

Thr Leu Gln Ala Ser Lys Ser Asp Val Pro Ile Asp Ile Cys Ser Ser
                245                 250                 255

Val Cys Lys Tyr Pro Asp Tyr Leu Gln Met Ala Ser Glu Pro Tyr Gly
            260                 265                 270

Asp Ser Leu Phe Phe Phe Leu Arg Arg Glu Gln Met Phe Val Arg His
        275                 280                 285

Phe Phe Asn Arg Ala Gly Thr Leu Gly Asp Pro Val Pro Gly Asp Leu
    290                 295                 300

Tyr Ile Gln Gly Ser Asn Ser Gly Asn Thr Ala Thr Val Gln Ser Ser
305                 310                 315                 320

Ala Phe Phe Pro Thr Pro Ser Gly Ser Met Val Thr Ser Glu Ser Gln
                325                 330                 335

Leu Phe Asn Lys Pro Tyr Trp Leu Gln Arg Ala Gln Gly His Asn Asn
            340                 345                 350

Gly Ile Cys Trp Gly Asn Gln Leu Phe Val Thr Val Val Asp Thr Thr
        355                 360                 365

Arg Ser Thr Asn Met Thr Leu Cys Ala Glu Val Lys Lys Glu Ser Thr
    370                 375                 380

Tyr Lys Asn Glu Asn Phe Lys Glu Tyr Leu Arg His Gly Glu Glu Phe
385                 390                 395                 400

Asp Leu Gln Phe Ile Phe Gln Leu Cys Lys Ile Thr Leu Thr Ala Asp
                405                 410                 415

Val Met Thr Tyr Ile His Lys Met Asp Ala Thr Ile Leu Glu Asp Trp
            420                 425                 430

Gln Phe Gly Leu Thr Pro Pro Ser Ala Ser Leu Glu Asp Thr Tyr
        435                 440                 445

Arg Phe Val Thr Ser Thr Ala Ile Thr Cys Gln Lys Asn Thr Pro Pro
    450                 455                 460

Lys Gly Lys Glu Asp Pro Leu Lys Asp Tyr Met Phe Trp Glu Val Asp
465                 470                 475                 480
```

-continued

```
Leu Lys Glu Lys Phe Ser Ala Asp Leu Asp Gln Phe Pro Leu Gly Arg
                485                 490                 495

Lys Phe Leu Leu Gln Ala Gly Leu Gln Ala Arg Pro Lys Leu Lys Arg
            500                 505                 510

Pro Ala Ser Ser Ala Pro Arg Thr Ser Thr Lys Lys Lys Val Lys
            515                 520                 525

Arg

<210> SEQ ID NO 4
<211> LENGTH: 490
<212> TYPE: PRT
<213> ORGANISM: Artificial Sequence
<220> FEATURE:
<223> OTHER INFORMATION: H58N35-33T1

<400> SEQUENCE: 4

Met Thr Val Tyr Leu Pro Val Pro Val Ser Lys Val Val Ser Thr
1               5                   10                  15

Asp Glu Tyr Val Ser Arg Thr Ser Ile Tyr Tyr Ala Gly Ser Ser
                20                  25                  30

Arg Leu Leu Ala Val Gly Asn Pro Tyr Phe Ser Ile Lys Asn Pro Thr
            35                  40                  45

Asn Ala Lys Lys Leu Leu Val Pro Lys Val Ser Gly Leu Gln Tyr Arg
        50                  55                  60

Val Phe Arg Val Arg Leu Pro Asp Pro Asn Lys Phe Gly Phe Pro Asp
65                  70                  75                  80

Thr Ser Phe Tyr Asn Pro Asp Thr Gln Arg Leu Val Trp Ala Cys Val
                85                  90                  95

Gly Leu Glu Ile Gly Arg Gly Gln Pro Leu Gly Val Gly Val Ser Gly
            100                 105                 110

His Pro Tyr Leu Asn Lys Phe Asp Asp Thr Glu Thr Ser Asn Arg Tyr
        115                 120                 125

Pro Ala Gln Pro Gly Ser Asp Asn Arg Glu Cys Leu Ser Met Asp Tyr
        130                 135                 140

Lys Gln Thr Gln Leu Cys Leu Ile Gly Cys Lys Pro Pro Thr Gly Glu
145                 150                 155                 160

His Trp Gly Lys Gly Val Ala Cys Asn Asn Asn Ala Ala Ala Thr Asp
                165                 170                 175

Cys Pro Pro Leu Glu Leu Phe Asn Ser Ile Ile Glu Asp Gly Asp Met
            180                 185                 190

Val Asp Thr Gly Phe Gly Cys Met Asp Phe Gly Thr Leu Gln Ala Asn
        195                 200                 205

Lys Ser Asp Val Pro Ile Asp Ile Cys Asn Ser Thr Cys Lys Tyr Pro
    210                 215                 220

Asp Tyr Leu Lys Met Ala Ser Glu Pro Tyr Gly Asp Ser Leu Phe Phe
225                 230                 235                 240

Phe Leu Arg Arg Glu Gln Met Phe Val Arg His Phe Phe Asn Arg Ala
                245                 250                 255

Gly Lys Leu Gly Glu Ala Val Pro Asp Asp Leu Tyr Ile Lys Gly Ser
            260                 265                 270

Gly Asn Thr Ala Val Ile Gln Ser Ser Ala Phe Phe Pro Thr Pro Ser
        275                 280                 285

Gly Ser Ile Val Thr Ser Glu Ser Gln Leu Phe Asn Lys Pro Tyr Trp
    290                 295                 300

Leu Gln Arg Ala Gln Gly His Asn Asn Gly Ile Cys Trp Gly Asn Gln
```

-continued

```
305                 310                 315                 320
Leu Phe Val Thr Val Asp Thr Thr Arg Ser Thr Asn Met Thr Leu
                325                 330                 335

Cys Thr Glu Val Thr Lys Glu Gly Thr Tyr Lys Asn Asp Asn Phe Lys
                340                 345                 350

Glu Tyr Val Arg His Val Glu Tyr Asp Leu Gln Phe Val Phe Gln
                355                 360                 365

Leu Cys Lys Ile Thr Leu Thr Ala Glu Ile Met Thr Tyr Ile His Thr
370                 375                 380

Met Asp Ser Asn Ile Leu Glu Asp Trp Gln Phe Gly Leu Thr Pro Pro
385                 390                 395                 400

Pro Ser Ala Ser Leu Gln Asp Thr Tyr Arg Phe Val Thr Ser Gln Ala
                405                 410                 415

Ile Thr Cys Gln Lys Thr Ala Pro Pro Lys Glu Lys Glu Asp Pro Leu
                420                 425                 430

Asn Lys Tyr Thr Phe Trp Glu Val Asn Leu Lys Glu Lys Phe Ser Ala
                435                 440                 445

Asp Leu Asp Gln Phe Pro Leu Gly Arg Lys Phe Leu Leu Gln Ser Gly
450                 455                 460

Leu Lys Ala Lys Pro Arg Leu Lys Arg Ser Ala Pro Thr Thr Arg Ala
465                 470                 475                 480

Pro Ser Thr Lys Arg Lys Lys Val Lys Lys
                485                 490
```

<210> SEQ ID NO 5
<211> LENGTH: 490
<212> TYPE: PRT
<213> ORGANISM: Artificial Sequence
<220> FEATURE:
<223> OTHER INFORMATION: H58N35-33T2-1

<400> SEQUENCE: 5

```
Met Thr Val Tyr Leu Pro Pro Val Pro Val Ser Lys Val Val Ser Thr
1               5                   10                  15

Asp Glu Tyr Val Ser Arg Thr Ser Ile Tyr Tyr Tyr Ala Gly Ser Ser
                20                  25                  30

Arg Leu Leu Ala Val Gly Asn Pro Tyr Phe Ser Ile Lys Ser Pro Asn
            35                  40                  45

Asn Asn Lys Lys Val Leu Val Pro Lys Val Ser Gly Leu Gln Tyr Arg
        50                  55                  60

Val Phe Arg Val Arg Leu Pro Asp Pro Asn Lys Phe Gly Phe Pro Asp
65                  70                  75                  80

Thr Ser Phe Tyr Asn Pro Asp Thr Gln Arg Leu Val Trp Ala Cys Val
                85                  90                  95

Gly Leu Glu Ile Gly Arg Gly Gln Pro Leu Gly Val Gly Ile Ser Gly
                100                 105                 110

His Pro Leu Leu Asn Lys Phe Asp Asp Thr Glu Thr Ser Asn Arg Tyr
            115                 120                 125

Pro Ala Gln Pro Gly Ser Asp Asn Arg Glu Cys Leu Ser Met Asp Tyr
        130                 135                 140

Lys Gln Thr Gln Leu Cys Leu Ile Gly Cys Lys Pro Pro Thr Gly Glu
145                 150                 155                 160

His Trp Gly Lys Gly Val Ala Cys Asn Asn Asn Ala Ala Ala Thr Asp
                165                 170                 175

Cys Pro Pro Leu Glu Leu Phe Asn Ser Ile Ile Glu Asp Gly Asp Met
```

```
                    180                 185                 190
Val Asp Thr Gly Phe Gly Cys Met Asp Phe Gly Thr Leu Gln Ala Asn
                195                 200                 205
Lys Ser Asp Val Pro Ile Asp Ile Cys Asn Ser Thr Cys Lys Tyr Pro
        210                 215                 220
Asp Tyr Leu Lys Met Ala Ser Glu Pro Tyr Gly Asp Ser Leu Phe Phe
225                 230                 235                 240
Phe Leu Arg Arg Glu Gln Met Phe Val Arg His Phe Asn Arg Ala
                245                 250                 255
Gly Lys Leu Gly Glu Ala Val Pro Asp Asp Leu Tyr Ile Lys Gly Ser
                260                 265                 270
Gly Asn Thr Ala Val Ile Gln Ser Ser Ala Phe Phe Pro Thr Pro Ser
            275                 280                 285
Gly Ser Ile Val Thr Ser Glu Ser Gln Leu Phe Asn Lys Pro Tyr Trp
        290                 295                 300
Leu Gln Arg Ala Gln Gly His Asn Asn Gly Ile Cys Trp Gly Asn Gln
305                 310                 315                 320
Leu Phe Val Thr Val Val Asp Thr Thr Arg Ser Thr Asn Met Thr Leu
                325                 330                 335
Cys Thr Glu Val Thr Lys Glu Gly Thr Tyr Lys Asn Asp Asn Phe Lys
                340                 345                 350
Glu Tyr Val Arg His Val Glu Glu Tyr Asp Leu Gln Phe Val Phe Gln
            355                 360                 365
Leu Cys Lys Ile Thr Leu Thr Ala Glu Ile Met Thr Tyr Ile His Thr
        370                 375                 380
Met Asp Ser Asn Ile Leu Glu Asp Trp Gln Phe Gly Leu Thr Pro Pro
385                 390                 395                 400
Pro Ser Ala Ser Leu Gln Asp Thr Tyr Arg Phe Val Thr Ser Gln Ala
                405                 410                 415
Ile Thr Cys Gln Lys Thr Ala Pro Pro Lys Glu Lys Glu Asp Pro Leu
                420                 425                 430
Asn Lys Tyr Thr Phe Trp Glu Val Asn Leu Lys Glu Lys Phe Ser Ala
            435                 440                 445
Asp Leu Asp Gln Phe Pro Leu Gly Arg Lys Phe Leu Leu Gln Ser Gly
        450                 455                 460
Leu Lys Ala Lys Pro Arg Leu Lys Arg Ser Ala Pro Thr Thr Arg Ala
465                 470                 475                 480
Pro Ser Thr Lys Arg Lys Lys Val Lys Lys
                485                 490

<210> SEQ ID NO 6
<211> LENGTH: 490
<212> TYPE: PRT
<213> ORGANISM: Artificial Sequence
<220> FEATURE:
<223> OTHER INFORMATION: H58N35-33T2-2

<400> SEQUENCE: 6

Met Thr Val Tyr Leu Pro Pro Val Pro Val Ser Lys Val Val Ser Thr
1               5                   10                  15
Asp Glu Tyr Val Ser Arg Thr Ser Ile Tyr Tyr Ala Gly Ser Ser
                20                  25                  30
Arg Leu Leu Ala Val Gly Asn Pro Tyr Phe Ser Ile Lys Ser Pro Asn
            35                  40                  45
Asn Asn Lys Lys Val Leu Val Pro Lys Val Ser Gly Leu Gln Tyr Arg
```

```
            50                  55                  60
Val Phe Arg Val Arg Leu Pro Asp Pro Asn Lys Phe Gly Phe Pro Asp
 65                  70                  75                  80

Thr Ser Phe Tyr Asn Pro Asp Thr Gln Arg Leu Val Trp Ala Cys Val
                 85                  90                  95

Gly Leu Glu Ile Gly Arg Gly Gln Pro Leu Gly Val Gly Ile Ser Gly
            100                 105                 110

His Pro Leu Leu Asn Lys Phe Asp Asp Thr Glu Thr Gly Asn Lys Tyr
            115                 120                 125

Pro Ala Gln Pro Gly Ser Asp Asn Arg Glu Cys Leu Ser Met Asp Tyr
            130                 135                 140

Lys Gln Thr Gln Leu Cys Leu Ile Gly Cys Lys Pro Pro Thr Gly Glu
145                 150                 155                 160

His Trp Gly Lys Gly Val Ala Cys Asn Asn Asn Ala Ala Ala Thr Asp
                165                 170                 175

Cys Pro Pro Leu Glu Leu Phe Asn Ser Ile Ile Glu Asp Gly Asp Met
            180                 185                 190

Val Asp Thr Gly Phe Gly Cys Met Asp Phe Gly Thr Leu Gln Ala Asn
            195                 200                 205

Lys Ser Asp Val Pro Ile Asp Ile Cys Asn Ser Thr Cys Lys Tyr Pro
210                 215                 220

Asp Tyr Leu Lys Met Ala Ser Glu Pro Tyr Gly Asp Ser Leu Phe Phe
225                 230                 235                 240

Phe Leu Arg Arg Glu Gln Met Phe Val Arg His Phe Phe Asn Arg Ala
                245                 250                 255

Gly Lys Leu Gly Glu Ala Val Pro Asp Asp Leu Tyr Ile Lys Gly Ser
            260                 265                 270

Gly Asn Thr Ala Val Ile Gln Ser Ser Ala Phe Phe Pro Thr Pro Ser
            275                 280                 285

Gly Ser Ile Val Thr Ser Glu Ser Gln Leu Phe Asn Lys Pro Tyr Trp
            290                 295                 300

Leu Gln Arg Ala Gln Gly His Asn Asn Gly Ile Cys Trp Gly Asn Gln
305                 310                 315                 320

Leu Phe Val Thr Val Val Asp Thr Thr Arg Ser Thr Asn Met Thr Leu
                325                 330                 335

Cys Thr Glu Val Thr Lys Glu Gly Thr Tyr Lys Asn Asp Asn Phe Lys
            340                 345                 350

Glu Tyr Val Arg His Val Glu Glu Tyr Asp Leu Gln Phe Val Phe Gln
            355                 360                 365

Leu Cys Lys Ile Thr Leu Thr Ala Glu Ile Met Thr Tyr Ile His Thr
370                 375                 380

Met Asp Ser Asn Ile Leu Glu Asp Trp Gln Phe Gly Leu Thr Pro Pro
385                 390                 395                 400

Pro Ser Ala Ser Leu Gln Asp Thr Tyr Arg Phe Val Thr Ser Gln Ala
                405                 410                 415

Ile Thr Cys Gln Lys Thr Ala Pro Pro Lys Glu Lys Glu Asp Pro Leu
            420                 425                 430

Asn Lys Tyr Thr Phe Trp Glu Val Asn Leu Lys Glu Lys Phe Ser Ala
            435                 440                 445

Asp Leu Asp Gln Phe Pro Leu Gly Arg Lys Phe Leu Leu Gln Ser Gly
            450                 455                 460

Leu Lys Ala Lys Pro Arg Leu Lys Arg Ser Ala Pro Thr Thr Arg Ala
465                 470                 475                 480
```

```
Pro Ser Thr Lys Arg Lys Lys Val Lys Lys
            485             490
```

<210> SEQ ID NO 7
<211> LENGTH: 490
<212> TYPE: PRT
<213> ORGANISM: Artificial Sequence
<220> FEATURE:
<223> OTHER INFORMATION: H58N35-33T2

<400> SEQUENCE: 7

```
Met Thr Val Tyr Leu Pro Pro Val Ser Lys Val Val Ser Thr
1               5                   10                  15

Asp Glu Tyr Val Ser Arg Thr Ser Ile Tyr Tyr Ala Gly Ser Ser
                20                  25                  30

Arg Leu Leu Ala Val Gly Asn Pro Tyr Phe Ser Ile Lys Ser Pro Asn
            35                  40                  45

Asn Asn Lys Lys Val Leu Val Pro Lys Ser Gly Leu Gln Tyr Arg
50                  55                  60

Val Phe Arg Val Arg Leu Pro Asp Pro Asn Lys Phe Gly Phe Pro Asp
65              70                  75                  80

Thr Ser Phe Tyr Asn Pro Asp Thr Gln Arg Leu Val Trp Ala Cys Val
                85                  90                  95

Gly Leu Glu Ile Gly Arg Gly Gln Pro Leu Gly Val Gly Ile Ser Gly
            100                 105                 110

His Pro Leu Leu Asn Lys Phe Asp Asp Thr Glu Thr Gly Asn Lys Tyr
        115                 120                 125

Pro Gly Gln Pro Gly Ala Asp Asn Arg Glu Cys Leu Ser Met Asp Tyr
    130                 135                 140

Lys Gln Thr Gln Leu Cys Leu Ile Gly Cys Lys Pro Pro Thr Gly Glu
145                 150                 155                 160

His Trp Gly Lys Gly Val Ala Cys Asn Asn Ala Ala Ala Thr Asp
                165                 170                 175

Cys Pro Pro Leu Glu Leu Phe Asn Ser Ile Ile Glu Asp Gly Asp Met
            180                 185                 190

Val Asp Thr Gly Phe Gly Cys Met Asp Phe Gly Thr Leu Gln Ala Asn
        195                 200                 205

Lys Ser Asp Val Pro Ile Asp Ile Cys Asn Ser Thr Cys Lys Tyr Pro
    210                 215                 220

Asp Tyr Leu Lys Met Ala Ser Glu Pro Tyr Gly Asp Ser Leu Phe Phe
225                 230                 235                 240

Phe Leu Arg Arg Glu Gln Met Phe Val Arg His Phe Asn Arg Ala
                245                 250                 255

Gly Lys Leu Gly Glu Ala Val Pro Asp Asp Leu Tyr Ile Lys Gly Ser
            260                 265                 270

Gly Asn Thr Ala Val Ile Gln Ser Ser Ala Phe Phe Pro Thr Pro Ser
        275                 280                 285

Gly Ser Ile Val Thr Ser Glu Ser Gln Leu Phe Asn Lys Pro Tyr Trp
    290                 295                 300

Leu Gln Arg Ala Gln Gly His Asn Asn Gly Ile Cys Trp Gly Asn Gln
305                 310                 315                 320

Leu Phe Val Thr Val Val Asp Thr Thr Arg Ser Thr Asn Met Thr Leu
                325                 330                 335

Cys Thr Glu Val Thr Lys Glu Gly Thr Tyr Lys Asn Asp Asn Phe Lys
            340                 345                 350
```

```
Glu Tyr Val Arg His Val Glu Glu Tyr Asp Leu Gln Phe Val Phe Gln
            355                 360                 365
Leu Cys Lys Ile Thr Leu Thr Ala Glu Ile Met Thr Tyr Ile His Thr
        370                 375                 380
Met Asp Ser Asn Ile Leu Glu Asp Trp Gln Phe Gly Leu Thr Pro Pro
385                 390                 395                 400
Pro Ser Ala Ser Leu Gln Asp Thr Tyr Arg Phe Val Thr Ser Gln Ala
                405                 410                 415
Ile Thr Cys Gln Lys Thr Ala Pro Pro Lys Glu Lys Glu Asp Pro Leu
            420                 425                 430
Asn Lys Tyr Thr Phe Trp Glu Val Asn Leu Lys Glu Lys Phe Ser Ala
                435                 440                 445
Asp Leu Asp Gln Phe Pro Leu Gly Arg Lys Phe Leu Leu Gln Ser Gly
            450                 455                 460
Leu Lys Ala Lys Pro Arg Leu Lys Arg Ser Ala Pro Thr Thr Arg Ala
465                 470                 475                 480
Pro Ser Thr Lys Arg Lys Lys Val Lys Lys
                485                 490

<210> SEQ ID NO 8
<211> LENGTH: 490
<212> TYPE: PRT
<213> ORGANISM: Artificial Sequence
<220> FEATURE:
<223> OTHER INFORMATION: H58N35-33T3

<400> SEQUENCE: 8

Met Thr Val Tyr Leu Pro Pro Val Pro Val Ser Lys Val Val Ser Thr
1               5                   10                  15
Asp Glu Tyr Val Ser Arg Thr Ser Ile Tyr Tyr Ala Gly Ser Ser
                20                  25                  30
Arg Leu Leu Ala Val Gly Asn Pro Tyr Phe Ser Ile Lys Ser Pro Asn
            35                  40                  45
Asn Asn Lys Lys Val Leu Val Pro Lys Val Ser Gly Leu Gln Tyr Arg
        50                  55                  60
Val Phe Arg Val Arg Leu Pro Asp Pro Asn Lys Phe Gly Phe Pro Asp
65                  70                  75                  80
Thr Ser Phe Tyr Asn Pro Asp Thr Gln Arg Leu Val Trp Ala Cys Val
                85                  90                  95
Gly Leu Glu Ile Gly Arg Gly Gln Pro Leu Gly Val Gly Val Ser Gly
            100                 105                 110
His Pro Tyr Leu Asn Lys Phe Asp Asp Thr Glu Thr Ser Asn Arg Tyr
        115                 120                 125
Pro Ala Gln Pro Gly Ser Asp Asn Arg Glu Cys Leu Ser Met Asp Tyr
    130                 135                 140
Lys Gln Thr Gln Leu Cys Leu Ile Gly Cys Lys Pro Pro Thr Gly Glu
145                 150                 155                 160
His Trp Gly Lys Gly Val Ala Cys Thr Asn Ala Ala Pro Ala Asn Asp
                165                 170                 175
Cys Pro Pro Leu Glu Leu Phe Asn Ser Ile Ile Glu Asp Gly Asp Met
            180                 185                 190
Val Asp Thr Gly Phe Gly Cys Met Asp Phe Gly Thr Leu Gln Ala Asn
        195                 200                 205
Lys Ser Asp Val Pro Ile Asp Ile Cys Asn Ser Thr Cys Lys Tyr Pro
    210                 215                 220
```

-continued

Asp Tyr Leu Lys Met Ala Ser Glu Pro Tyr Gly Asp Ser Leu Phe Phe
225                 230                 235                 240

Phe Leu Arg Arg Glu Gln Met Phe Val Arg His Phe Phe Asn Arg Ala
            245                 250                 255

Gly Lys Leu Gly Glu Ala Val Pro Asp Asp Leu Tyr Ile Lys Gly Ser
        260                 265                 270

Gly Asn Thr Ala Val Ile Gln Ser Ser Ala Phe Phe Pro Thr Pro Ser
    275                 280                 285

Gly Ser Ile Val Thr Ser Glu Ser Gln Leu Phe Asn Lys Pro Tyr Trp
290                 295                 300

Leu Gln Arg Ala Gln Gly His Asn Asn Gly Ile Cys Trp Gly Asn Gln
305                 310                 315                 320

Leu Phe Val Thr Val Asp Thr Thr Arg Ser Thr Asn Met Thr Leu
            325                 330                 335

Cys Thr Glu Val Thr Lys Glu Gly Thr Tyr Lys Asn Asp Asn Phe Lys
            340                 345                 350

Glu Tyr Val Arg His Val Glu Glu Tyr Asp Leu Gln Phe Val Phe Gln
            355                 360                 365

Leu Cys Lys Ile Thr Leu Thr Ala Glu Ile Met Thr Tyr Ile His Thr
370                 375                 380

Met Asp Ser Asn Ile Leu Glu Asp Trp Gln Phe Gly Leu Thr Pro Pro
385                 390                 395                 400

Pro Ser Ala Ser Leu Gln Asp Thr Tyr Arg Phe Val Thr Ser Gln Ala
            405                 410                 415

Ile Thr Cys Gln Lys Thr Ala Pro Pro Lys Glu Lys Glu Asp Pro Leu
            420                 425                 430

Asn Lys Tyr Thr Phe Trp Glu Val Asn Leu Lys Glu Lys Phe Ser Ala
            435                 440                 445

Asp Leu Asp Gln Phe Pro Leu Gly Arg Lys Phe Leu Leu Gln Ser Gly
            450                 455                 460

Leu Lys Ala Lys Pro Arg Leu Lys Arg Ser Ala Pro Thr Thr Arg Ala
465                 470                 475                 480

Pro Ser Thr Lys Arg Lys Lys Val Lys Lys
            485                 490

<210> SEQ ID NO 9
<211> LENGTH: 490
<212> TYPE: PRT
<213> ORGANISM: Artificial Sequence
<220> FEATURE:
<223> OTHER INFORMATION: H58N35-33T4

<400> SEQUENCE: 9

Met Thr Val Tyr Leu Pro Pro Val Pro Val Ser Lys Val Val Ser Thr
1               5                   10                  15

Asp Glu Tyr Val Ser Arg Thr Ser Ile Tyr Tyr Tyr Ala Gly Ser Ser
            20                  25                  30

Arg Leu Leu Ala Val Gly Asn Pro Tyr Phe Ser Ile Lys Ser Pro Asn
        35                  40                  45

Asn Asn Lys Lys Val Leu Val Pro Lys Val Ser Gly Leu Gln Tyr Arg
    50                  55                  60

Val Phe Arg Val Arg Leu Pro Asp Pro Asn Lys Phe Gly Phe Pro Asp
65                  70                  75                  80

Thr Ser Phe Tyr Asn Pro Asp Thr Gln Arg Leu Val Trp Ala Cys Val
            85                  90                  95

```
Gly Leu Glu Ile Gly Arg Gly Gln Pro Leu Gly Val Gly Val Ser Gly
                100                 105                 110

His Pro Tyr Leu Asn Lys Phe Asp Asp Thr Glu Thr Ser Asn Arg Tyr
            115                 120                 125

Pro Ala Gln Pro Gly Ser Asp Asn Arg Glu Cys Leu Ser Met Asp Tyr
        130                 135                 140

Lys Gln Thr Gln Leu Cys Leu Ile Gly Cys Lys Pro Pro Thr Gly Glu
145                 150                 155                 160

His Trp Gly Lys Gly Val Ala Cys Asn Asn Asn Ala Ala Thr Asp
                165                 170                 175

Cys Pro Pro Leu Glu Leu Phe Asn Ser Ile Ile Glu Asp Gly Asp Met
                180                 185                 190

Val Asp Thr Gly Phe Gly Cys Met Asp Phe Gly Thr Leu Gln Ala Asn
            195                 200                 205

Lys Ser Asp Val Pro Ile Asp Ile Cys Asn Ser Thr Cys Lys Tyr Pro
210                 215                 220

Asp Tyr Leu Lys Met Ala Ser Glu Pro Tyr Gly Asp Ser Leu Phe Phe
225                 230                 235                 240

Phe Leu Arg Arg Glu Gln Met Phe Val Arg His Phe Asn Arg Ala
                245                 250                 255

Gly Lys Leu Gly Glu Ala Val Pro Asp Asp Leu Tyr Ile Lys Gly Ser
            260                 265                 270

Gly Thr Thr Ala Ser Ile Gln Ser Ser Ala Phe Phe Pro Thr Pro Ser
            275                 280                 285

Gly Ser Ile Val Thr Ser Glu Ser Gln Leu Phe Asn Lys Pro Tyr Trp
            290                 295                 300

Leu Gln Arg Ala Gln Gly His Asn Asn Gly Ile Cys Trp Gly Asn Gln
305                 310                 315                 320

Leu Phe Val Thr Val Val Asp Thr Thr Arg Ser Thr Asn Met Thr Leu
                325                 330                 335

Cys Thr Glu Val Thr Lys Glu Gly Thr Tyr Lys Asn Asp Asn Phe Lys
                340                 345                 350

Glu Tyr Val Arg His Val Glu Glu Tyr Asp Leu Gln Phe Val Phe Gln
                355                 360                 365

Leu Cys Lys Ile Thr Leu Thr Ala Glu Ile Met Thr Tyr Ile His Thr
370                 375                 380

Met Asp Ser Asn Ile Leu Glu Asp Trp Gln Phe Gly Leu Thr Pro Pro
385                 390                 395                 400

Pro Ser Ala Ser Leu Gln Asp Thr Tyr Arg Phe Val Thr Ser Gln Ala
                405                 410                 415

Ile Thr Cys Gln Lys Thr Ala Pro Pro Lys Glu Lys Glu Asp Pro Leu
                420                 425                 430

Asn Lys Tyr Thr Phe Trp Glu Val Asn Leu Lys Glu Lys Phe Ser Ala
            435                 440                 445

Asp Leu Asp Gln Phe Pro Leu Gly Arg Lys Phe Leu Leu Gln Ser Gly
        450                 455                 460

Leu Lys Ala Lys Pro Arg Leu Lys Arg Ser Ala Pro Thr Thr Arg Ala
465                 470                 475                 480

Pro Ser Thr Lys Arg Lys Lys Val Lys Lys
                485                 490

<210> SEQ ID NO 10
<211> LENGTH: 490
```

```
<212> TYPE: PRT
<213> ORGANISM: Artificial Sequence
<220> FEATURE:
<223> OTHER INFORMATION: H58N35-33T5

<400> SEQUENCE: 10
```

| | | | | | | | | | | | | | | |
|---|---|---|---|---|---|---|---|---|---|---|---|---|---|---|
| Met | Thr | Val | Tyr | Leu | Pro | Pro | Val | Pro | Val | Ser | Lys | Val | Val | Ser | Thr |
| 1 | | | | 5 | | | | | 10 | | | | | 15 | |

| Asp | Glu | Tyr | Val | Ser | Arg | Thr | Ser | Ile | Tyr | Tyr | Ala | Gly | Ser | Ser |
|---|---|---|---|---|---|---|---|---|---|---|---|---|---|---|
| | | | 20 | | | | | 25 | | | | | 30 | |

| Arg | Leu | Leu | Ala | Val | Gly | Asn | Pro | Tyr | Phe | Ser | Ile | Lys | Ser | Pro | Asn |
|---|---|---|---|---|---|---|---|---|---|---|---|---|---|---|---|
| | | | 35 | | | | | 40 | | | | | 45 | | |

| Asn | Asn | Lys | Lys | Val | Leu | Val | Pro | Lys | Val | Ser | Gly | Leu | Gln | Tyr | Arg |
|---|---|---|---|---|---|---|---|---|---|---|---|---|---|---|---|
| | 50 | | | | | 55 | | | | | 60 | | | | |

| Val | Phe | Arg | Val | Arg | Leu | Pro | Asp | Pro | Asn | Lys | Phe | Gly | Phe | Pro | Asp |
|---|---|---|---|---|---|---|---|---|---|---|---|---|---|---|---|
| 65 | | | | | 70 | | | | | 75 | | | | | 80 |

| Thr | Ser | Phe | Tyr | Asn | Pro | Asp | Thr | Gln | Arg | Leu | Val | Trp | Ala | Cys | Val |
|---|---|---|---|---|---|---|---|---|---|---|---|---|---|---|---|
| | | | | 85 | | | | | 90 | | | | | 95 | |

| Gly | Leu | Glu | Ile | Gly | Arg | Gly | Gln | Pro | Leu | Gly | Val | Gly | Val | Ser | Gly |
|---|---|---|---|---|---|---|---|---|---|---|---|---|---|---|---|
| | | | 100 | | | | | 105 | | | | | 110 | | |

| His | Pro | Tyr | Leu | Asn | Lys | Phe | Asp | Asp | Thr | Glu | Thr | Ser | Asn | Arg | Tyr |
|---|---|---|---|---|---|---|---|---|---|---|---|---|---|---|---|
| | | 115 | | | | | 120 | | | | | 125 | | | |

| Pro | Ala | Gln | Pro | Gly | Ser | Asp | Asn | Arg | Glu | Cys | Leu | Ser | Met | Asp | Tyr |
|---|---|---|---|---|---|---|---|---|---|---|---|---|---|---|---|
| | 130 | | | | | 135 | | | | | 140 | | | | |

| Lys | Gln | Thr | Gln | Leu | Cys | Leu | Ile | Gly | Cys | Lys | Pro | Pro | Thr | Gly | Glu |
|---|---|---|---|---|---|---|---|---|---|---|---|---|---|---|---|
| 145 | | | | | 150 | | | | | 155 | | | | | 160 |

| His | Trp | Gly | Lys | Gly | Val | Ala | Cys | Asn | Asn | Asn | Ala | Ala | Ala | Thr | Asp |
|---|---|---|---|---|---|---|---|---|---|---|---|---|---|---|---|
| | | | | 165 | | | | | 170 | | | | | 175 | |

| Cys | Pro | Pro | Leu | Glu | Leu | Phe | Asn | Ser | Ile | Ile | Glu | Asp | Gly | Asp | Met |
|---|---|---|---|---|---|---|---|---|---|---|---|---|---|---|---|
| | | | 180 | | | | | 185 | | | | | 190 | | |

| Val | Asp | Thr | Gly | Phe | Gly | Cys | Met | Asp | Phe | Gly | Thr | Leu | Gln | Ala | Asn |
|---|---|---|---|---|---|---|---|---|---|---|---|---|---|---|---|
| | | 195 | | | | | 200 | | | | | 205 | | | |

| Lys | Ser | Asp | Val | Pro | Ile | Asp | Ile | Cys | Asn | Ser | Thr | Cys | Lys | Tyr | Pro |
|---|---|---|---|---|---|---|---|---|---|---|---|---|---|---|---|
| | 210 | | | | | 215 | | | | | 220 | | | | |

| Asp | Tyr | Leu | Lys | Met | Ala | Ser | Glu | Pro | Tyr | Gly | Asp | Ser | Leu | Phe | Phe |
|---|---|---|---|---|---|---|---|---|---|---|---|---|---|---|---|
| 225 | | | | | 230 | | | | | 235 | | | | | 240 |

| Phe | Leu | Arg | Arg | Glu | Gln | Met | Phe | Val | Arg | His | Phe | Phe | Asn | Arg | Ala |
|---|---|---|---|---|---|---|---|---|---|---|---|---|---|---|---|
| | | | | 245 | | | | | 250 | | | | | 255 | |

| Gly | Lys | Leu | Gly | Glu | Ala | Val | Pro | Asp | Asp | Leu | Tyr | Ile | Lys | Gly | Ser |
|---|---|---|---|---|---|---|---|---|---|---|---|---|---|---|---|
| | | | 260 | | | | | 265 | | | | | 270 | | |

| Gly | Asn | Thr | Ala | Val | Ile | Gln | Ser | Ser | Ala | Phe | Phe | Pro | Thr | Pro | Ser |
|---|---|---|---|---|---|---|---|---|---|---|---|---|---|---|---|
| | | 275 | | | | | 280 | | | | | 285 | | | |

| Gly | Ser | Ile | Val | Thr | Ser | Glu | Ser | Gln | Leu | Phe | Asn | Lys | Pro | Tyr | Trp |
|---|---|---|---|---|---|---|---|---|---|---|---|---|---|---|---|
| | 290 | | | | | 295 | | | | | 300 | | | | |

| Leu | Gln | Arg | Ala | Gln | Gly | His | Asn | Asn | Gly | Ile | Cys | Trp | Gly | Asn | Gln |
|---|---|---|---|---|---|---|---|---|---|---|---|---|---|---|---|
| 305 | | | | | 310 | | | | | 315 | | | | | 320 |

| Leu | Phe | Val | Thr | Val | Asp | Thr | Thr | Arg | Ser | Thr | Asn | Met | Thr | Leu |
|---|---|---|---|---|---|---|---|---|---|---|---|---|---|---|
| | | | | 325 | | | | | 330 | | | | | 335 |

| Cys | Thr | Glu | Val | Thr | Ser | Asp | Ser | Thr | Tyr | Lys | Asn | Glu | Asn | Phe | Lys |
|---|---|---|---|---|---|---|---|---|---|---|---|---|---|---|---|
| | | | 340 | | | | | 345 | | | | | 350 | | |

| Glu | Tyr | Val | Arg | His | Val | Glu | Glu | Tyr | Asp | Leu | Gln | Phe | Val | Phe | Gln |
|---|---|---|---|---|---|---|---|---|---|---|---|---|---|---|---|
| | | 355 | | | | | 360 | | | | | 365 | | | |

| Leu | Cys | Lys | Ile | Thr | Leu | Thr | Ala | Glu | Ile | Met | Thr | Tyr | Ile | His | Thr |
|---|---|---|---|---|---|---|---|---|---|---|---|---|---|---|---|
| 370 | | | | | 375 | | | | | 380 | | | | | |

-continued

```
Met Asp Ser Asn Ile Leu Glu Asp Trp Gln Phe Gly Leu Thr Pro Pro
385                 390                 395                 400

Pro Ser Ala Ser Leu Gln Asp Thr Tyr Arg Phe Val Thr Ser Gln Ala
            405                 410                 415

Ile Thr Cys Gln Lys Thr Ala Pro Pro Lys Glu Lys Glu Asp Pro Leu
        420                 425                 430

Asn Lys Tyr Thr Phe Trp Glu Val Asn Leu Lys Glu Lys Phe Ser Ala
            435                 440                 445

Asp Leu Asp Gln Phe Pro Leu Gly Arg Lys Phe Leu Leu Gln Ser Gly
        450                 455                 460

Leu Lys Ala Lys Pro Arg Leu Lys Arg Ser Ala Pro Thr Thr Arg Ala
465                 470                 475                 480

Pro Ser Thr Lys Arg Lys Lys Val Lys Lys
            485                 490

<210> SEQ ID NO 11
<211> LENGTH: 490
<212> TYPE: PRT
<213> ORGANISM: Artificial Sequence
<220> FEATURE:
<223> OTHER INFORMATION: H58N35-33T1-52S1

<400> SEQUENCE: 11

Met Thr Val Tyr Leu Pro Pro Val Pro Val Ser Lys Val Val Ser Thr
1               5                   10                  15

Asp Glu Tyr Val Ser Arg Thr Ser Ile Tyr Tyr Ala Gly Ser Ser
            20                  25                  30

Arg Leu Leu Ala Val Gly Asn Pro Tyr Phe Ser Ile Lys Asn Pro Thr
        35                  40                  45

Asn Ala Lys Lys Leu Leu Val Pro Lys Val Ser Gly Leu Gln Tyr Arg
50                  55                  60

Val Phe Arg Val Arg Leu Pro Asp Pro Asn Lys Phe Gly Phe Pro Asp
65                  70                  75                  80

Thr Ser Phe Tyr Asn Pro Asp Thr Gln Arg Leu Val Trp Ala Cys Val
            85                  90                  95

Gly Leu Glu Ile Gly Arg Gly Gln Pro Leu Gly Val Gly Ile Ser Gly
        100                 105                 110

His Pro Leu Leu Asn Lys Phe Asp Asp Thr Glu Thr Ser Asn Lys Tyr
    115                 120                 125

Ala Gly Lys Pro Gly Ile Asp Asn Arg Glu Cys Leu Ser Met Asp Tyr
130                 135                 140

Lys Gln Thr Gln Leu Cys Leu Ile Gly Cys Lys Pro Pro Thr Gly Glu
145                 150                 155                 160

His Trp Gly Lys Gly Val Ala Cys Asn Asn Ala Ala Ala Thr Asp
            165                 170                 175

Cys Pro Pro Leu Glu Leu Phe Asn Ser Ile Ile Glu Asp Gly Asp Met
        180                 185                 190

Val Asp Thr Gly Phe Gly Cys Met Asp Phe Gly Thr Leu Gln Ala Asn
    195                 200                 205

Lys Ser Asp Val Pro Ile Asp Ile Cys Asn Ser Thr Cys Lys Tyr Pro
210                 215                 220

Asp Tyr Leu Lys Met Ala Ser Glu Pro Tyr Gly Asp Ser Leu Phe Phe
225                 230                 235                 240

Phe Leu Arg Arg Glu Gln Met Phe Val Arg His Phe Phe Asn Arg Ala
            245                 250                 255
```

```
Gly Lys Leu Gly Glu Ala Val Pro Asp Asp Leu Tyr Ile Lys Gly Ser
                260                 265                 270

Gly Asn Thr Ala Val Ile Gln Ser Ser Ala Phe Phe Pro Thr Pro Ser
            275                 280                 285

Gly Ser Ile Val Thr Ser Glu Ser Gln Leu Phe Asn Lys Pro Tyr Trp
            290                 295                 300

Leu Gln Arg Ala Gln Gly His Asn Asn Gly Ile Cys Trp Gly Asn Gln
305                 310                 315                 320

Leu Phe Val Thr Val Asp Thr Thr Arg Ser Thr Asn Met Thr Leu
                325                 330                 335

Cys Thr Glu Val Thr Lys Glu Gly Thr Tyr Lys Asn Asp Asn Phe Lys
                340                 345                 350

Glu Tyr Val Arg His Val Glu Glu Tyr Asp Leu Gln Phe Val Phe Gln
                355                 360                 365

Leu Cys Lys Ile Thr Leu Thr Ala Glu Ile Met Thr Tyr Ile His Thr
370                 375                 380

Met Asp Ser Asn Ile Leu Glu Asp Trp Gln Phe Gly Leu Thr Pro Pro
385                 390                 395                 400

Pro Ser Ala Ser Leu Gln Asp Thr Tyr Arg Phe Val Thr Ser Gln Ala
                405                 410                 415

Ile Thr Cys Gln Lys Thr Ala Pro Pro Lys Glu Lys Glu Asp Pro Leu
                420                 425                 430

Asn Lys Tyr Thr Phe Trp Glu Val Asn Leu Lys Glu Lys Phe Ser Ala
                435                 440                 445

Asp Leu Asp Gln Phe Pro Leu Gly Arg Lys Phe Leu Leu Gln Ser Gly
450                 455                 460

Leu Lys Ala Lys Pro Arg Leu Lys Arg Ser Ala Pro Thr Thr Arg Ala
465                 470                 475                 480

Pro Ser Thr Lys Arg Lys Lys Val Lys Lys
                485                 490

<210> SEQ ID NO 12
<211> LENGTH: 491
<212> TYPE: PRT
<213> ORGANISM: Artificial Sequence
<220> FEATURE:
<223> OTHER INFORMATION: H58N35-33T1-52S2

<400> SEQUENCE: 12

Met Thr Val Tyr Leu Pro Pro Val Pro Val Ser Lys Val Val Ser Thr
1               5                   10                  15

Asp Glu Tyr Val Ser Arg Thr Ser Ile Tyr Tyr Tyr Ala Gly Ser Ser
                20                  25                  30

Arg Leu Leu Ala Val Gly Asn Pro Tyr Phe Ser Ile Lys Asn Pro Thr
            35                  40                  45

Asn Ala Lys Lys Leu Leu Val Pro Lys Val Ser Gly Leu Gln Tyr Arg
50                  55                  60

Val Phe Arg Val Arg Leu Pro Asp Pro Asn Lys Phe Gly Phe Pro Asp
65                  70                  75                  80

Thr Ser Phe Tyr Asn Pro Asp Thr Gln Arg Leu Val Trp Ala Cys Val
                85                  90                  95

Gly Leu Glu Ile Gly Arg Gly Gln Pro Leu Gly Val Gly Val Ser Gly
                100                 105                 110

His Pro Tyr Leu Asn Lys Phe Asp Asp Thr Glu Thr Ser Asn Arg Tyr
            115                 120                 125
```

Pro Ala Gln Pro Gly Ser Asp Asn Arg Glu Cys Leu Ser Met Asp Tyr
    130                 135                 140

Lys Gln Thr Gln Leu Cys Leu Ile Gly Cys Lys Pro Thr Gly Glu
145                 150                 155                 160

His Trp Gly Lys Gly Thr Pro Cys Asn Asn Asn Ser Gly Asn Pro Gly
                165                 170                 175

Asp Cys Pro Pro Leu Glu Leu Phe Asn Ser Ile Ile Glu Asp Gly Asp
                180                 185                 190

Met Val Asp Thr Gly Phe Gly Cys Met Asp Phe Gly Thr Leu Gln Ala
            195                 200                 205

Asn Lys Ser Asp Val Pro Ile Asp Ile Cys Asn Ser Thr Cys Lys Tyr
210                 215                 220

Pro Asp Tyr Leu Lys Met Ala Ser Glu Pro Tyr Gly Asp Ser Leu Phe
225                 230                 235                 240

Phe Phe Leu Arg Arg Glu Gln Met Phe Val Arg His Phe Phe Asn Arg
                245                 250                 255

Ala Gly Lys Leu Gly Glu Ala Val Pro Asp Asp Leu Tyr Ile Lys Gly
                260                 265                 270

Ser Gly Asn Thr Ala Val Ile Gln Ser Ser Ala Phe Phe Pro Thr Pro
            275                 280                 285

Ser Gly Ser Ile Val Thr Ser Glu Ser Gln Leu Phe Asn Lys Pro Tyr
290                 295                 300

Trp Leu Gln Arg Ala Gln Gly His Asn Asn Gly Ile Cys Trp Gly Asn
305                 310                 315                 320

Gln Leu Phe Val Thr Val Val Asp Thr Thr Arg Ser Thr Asn Met Thr
                325                 330                 335

Leu Cys Thr Glu Val Thr Lys Glu Gly Thr Tyr Lys Asn Asp Asn Phe
                340                 345                 350

Lys Glu Tyr Val Arg His Val Glu Glu Tyr Asp Leu Gln Phe Val Phe
            355                 360                 365

Gln Leu Cys Lys Ile Thr Leu Thr Ala Glu Ile Met Thr Tyr Ile His
370                 375                 380

Thr Met Asp Ser Asn Ile Leu Glu Asp Trp Gln Phe Gly Leu Thr Pro
385                 390                 395                 400

Pro Pro Ser Ala Ser Leu Gln Asp Thr Tyr Arg Phe Val Thr Ser Gln
                405                 410                 415

Ala Ile Thr Cys Gln Lys Thr Ala Pro Pro Lys Glu Lys Glu Asp Pro
                420                 425                 430

Leu Asn Lys Tyr Thr Phe Trp Glu Val Asn Leu Lys Glu Lys Phe Ser
            435                 440                 445

Ala Asp Leu Asp Gln Phe Pro Leu Gly Arg Lys Phe Leu Leu Gln Ser
450                 455                 460

Gly Leu Lys Ala Lys Pro Arg Leu Lys Arg Ser Ala Pro Thr Thr Arg
465                 470                 475                 480

Ala Pro Ser Thr Lys Arg Lys Val Lys Lys
                485                 490

<210> SEQ ID NO 13
<211> LENGTH: 492
<212> TYPE: PRT
<213> ORGANISM: Artificial Sequence
<220> FEATURE:
<223> OTHER INFORMATION: H58N35-33T1-52S3

<400> SEQUENCE: 13

-continued

```
Met Thr Val Tyr Leu Pro Val Pro Val Ser Lys Val Val Ser Thr
1               5                   10                  15

Asp Glu Tyr Val Ser Arg Thr Ser Ile Tyr Tyr Ala Gly Ser Ser
                20                  25                  30

Arg Leu Leu Ala Val Gly Asn Pro Tyr Phe Ser Ile Lys Asn Pro Thr
            35                  40                  45

Asn Ala Lys Lys Leu Leu Val Pro Lys Val Ser Gly Leu Gln Tyr Arg
50                  55                  60

Val Phe Arg Val Arg Leu Pro Asp Pro Asn Lys Phe Gly Phe Pro Asp
65                  70                  75                  80

Thr Ser Phe Tyr Asn Pro Asp Thr Gln Arg Leu Val Trp Ala Cys Val
                85                  90                  95

Gly Leu Glu Ile Gly Arg Gly Gln Pro Leu Gly Val Gly Val Ser Gly
            100                 105                 110

His Pro Tyr Leu Asn Lys Phe Asp Asp Thr Glu Thr Ser Asn Arg Tyr
            115                 120                 125

Pro Ala Gln Pro Gly Ser Asp Asn Arg Glu Cys Leu Ser Met Asp Tyr
            130                 135                 140

Lys Gln Thr Gln Leu Cys Leu Ile Gly Cys Lys Pro Pro Thr Gly Glu
145                 150                 155                 160

His Trp Gly Lys Gly Val Ala Cys Asn Asn Asn Ala Ala Thr Asp
                165                 170                 175

Cys Pro Pro Leu Glu Leu Phe Asn Ser Ile Ile Glu Asp Gly Asp Met
            180                 185                 190

Val Asp Thr Gly Phe Gly Cys Met Asp Phe Gly Thr Leu Gln Ala Asn
            195                 200                 205

Lys Ser Asp Val Pro Ile Asp Ile Cys Asn Ser Thr Cys Lys Tyr Pro
210                 215                 220

Asp Tyr Leu Lys Met Ala Ser Glu Pro Tyr Gly Asp Ser Leu Phe Phe
225                 230                 235                 240

Phe Leu Arg Arg Glu Gln Met Phe Val Arg His Phe Asn Arg Ala
            245                 250                 255

Gly Thr Leu Gly Asp Pro Val Pro Gly Asp Leu Tyr Ile Gln Gly Ser
            260                 265                 270

Asn Ser Gly Asn Thr Ala Thr Val Gln Ser Ser Ala Phe Phe Pro Thr
            275                 280                 285

Pro Ser Gly Ser Ile Val Thr Ser Glu Ser Gln Leu Phe Asn Lys Pro
            290                 295                 300

Tyr Trp Leu Gln Arg Ala Gln Gly His Asn Asn Gly Ile Cys Trp Gly
305                 310                 315                 320

Asn Gln Leu Phe Val Thr Val Val Asp Thr Thr Arg Ser Thr Asn Met
                325                 330                 335

Thr Leu Cys Thr Glu Val Thr Lys Glu Gly Thr Tyr Lys Asn Asp Asn
                340                 345                 350

Phe Lys Glu Tyr Val Arg His Val Glu Glu Tyr Asp Leu Gln Phe Val
            355                 360                 365

Phe Gln Leu Cys Lys Ile Thr Leu Thr Ala Glu Ile Met Thr Tyr Ile
            370                 375                 380

His Thr Met Asp Ser Asn Ile Leu Glu Asp Trp Gln Phe Gly Leu Thr
385                 390                 395                 400

Pro Pro Pro Ser Ala Ser Leu Gln Asp Thr Tyr Arg Phe Val Thr Ser
            405                 410                 415

Gln Ala Ile Thr Cys Gln Lys Thr Ala Pro Pro Lys Glu Lys Glu Asp
```

```
                     420                 425                 430
Pro Leu Asn Lys Tyr Thr Phe Trp Glu Val Asn Leu Lys Glu Lys Phe
                435                 440                 445

Ser Ala Asp Leu Asp Gln Phe Pro Leu Gly Arg Lys Phe Leu Leu Gln
        450                 455                 460

Ser Gly Leu Lys Ala Lys Pro Arg Leu Lys Arg Ser Ala Pro Thr Thr
465                 470                 475                 480

Arg Ala Pro Ser Thr Lys Arg Lys Lys Val Lys Lys
                485                 490
```

<210> SEQ ID NO 14
<211> LENGTH: 490
<212> TYPE: PRT
<213> ORGANISM: Artificial Sequence
<220> FEATURE:
<223> OTHER INFORMATION: H58N35-33T1-52S4

<400> SEQUENCE: 14

```
Met Thr Val Tyr Leu Pro Pro Val Pro Ser Lys Val Val Ser Thr
1               5                   10                  15

Asp Glu Tyr Val Ser Arg Thr Ser Ile Tyr Tyr Ala Gly Ser Ser
                20                  25                  30

Arg Leu Leu Ala Val Gly Asn Pro Tyr Phe Ser Ile Lys Asn Pro Thr
            35                  40                  45

Asn Ala Lys Lys Leu Leu Val Pro Lys Val Ser Gly Leu Gln Tyr Arg
        50                  55                  60

Val Phe Arg Val Arg Leu Pro Asp Pro Asn Lys Phe Gly Phe Pro Asp
65                  70                  75                  80

Thr Ser Phe Tyr Asn Pro Asp Thr Gln Arg Leu Val Trp Ala Cys Val
                85                  90                  95

Gly Leu Glu Ile Gly Arg Gly Gln Pro Leu Gly Val Gly Val Ser Gly
            100                 105                 110

His Pro Tyr Leu Asn Lys Phe Asp Asp Thr Glu Thr Ser Asn Arg Tyr
        115                 120                 125

Pro Ala Gln Pro Gly Ser Asp Asn Arg Glu Cys Leu Ser Met Asp Tyr
130                 135                 140

Lys Gln Thr Gln Leu Cys Leu Ile Gly Cys Lys Pro Pro Thr Gly Glu
145                 150                 155                 160

His Trp Gly Lys Gly Val Ala Cys Asn Asn Asn Ala Ala Ala Thr Asp
                165                 170                 175

Cys Pro Pro Leu Glu Leu Phe Asn Ser Ile Ile Glu Asp Gly Asp Met
            180                 185                 190

Val Asp Thr Gly Phe Gly Cys Met Asp Phe Gly Thr Leu Gln Ala Asn
        195                 200                 205

Lys Ser Asp Val Pro Ile Asp Ile Cys Asn Ser Thr Cys Lys Tyr Pro
210                 215                 220

Asp Tyr Leu Lys Met Ala Ser Glu Pro Tyr Gly Asp Ser Leu Phe Phe
225                 230                 235                 240

Phe Leu Arg Arg Glu Gln Met Phe Val Arg His Phe Phe Asn Arg Ala
                245                 250                 255

Gly Lys Leu Gly Glu Ala Val Pro Asp Asp Leu Tyr Ile Lys Gly Ser
            260                 265                 270

Gly Asn Thr Ala Val Ile Gln Ser Ser Ala Phe Phe Pro Thr Pro Ser
        275                 280                 285

Gly Ser Ile Val Thr Ser Glu Ser Gln Leu Phe Asn Lys Pro Tyr Trp
```

|     |     |     |     |     |     |     |     |     |     |     |     |     |
| --- | --- | --- | --- | --- | --- | --- | --- | --- | --- | --- | --- | --- |
|     |     |     | 290 |     |     |     | 295 |     |     |     | 300 |     |
| Leu | Gln | Arg | Ala | Gln | Gly | His | Asn | Asn | Gly | Ile | Cys | Trp | Gly | Asn | Gln |
| 305 |     |     |     |     | 310 |     |     |     |     | 315 |     |     |     |     | 320 |
| Leu | Phe | Val | Thr | Val | Asp | Thr | Thr | Arg | Ser | Thr | Asn | Met | Thr | Leu |
|     |     |     |     | 325 |     |     |     |     | 330 |     |     |     |     | 335 |
| Cys | Thr | Glu | Val | Lys | Lys | Glu | Ser | Thr | Tyr | Lys | Asn | Glu | Asn | Phe | Lys |
|     |     |     |     | 340 |     |     |     |     | 345 |     |     |     |     | 350 |     |
| Glu | Tyr | Val | Arg | His | Val | Glu | Glu | Tyr | Asp | Leu | Gln | Phe | Val | Phe | Gln |
|     |     |     | 355 |     |     |     |     | 360 |     |     |     |     | 365 |     |     |
| Leu | Cys | Lys | Ile | Thr | Leu | Thr | Ala | Glu | Ile | Met | Thr | Tyr | Ile | His | Thr |
| 370 |     |     |     |     | 375 |     |     |     |     | 380 |     |     |     |     |     |
| Met | Asp | Ser | Asn | Ile | Leu | Glu | Asp | Trp | Gln | Phe | Gly | Leu | Thr | Pro | Pro |
| 385 |     |     |     |     | 390 |     |     |     |     | 395 |     |     |     |     | 400 |
| Pro | Ser | Ala | Ser | Leu | Gln | Asp | Thr | Tyr | Arg | Phe | Val | Thr | Ser | Gln | Ala |
|     |     |     |     | 405 |     |     |     |     | 410 |     |     |     |     | 415 |     |
| Ile | Thr | Cys | Gln | Lys | Thr | Ala | Pro | Pro | Lys | Glu | Lys | Glu | Asp | Pro | Leu |
|     |     |     | 420 |     |     |     |     | 425 |     |     |     |     | 430 |     |     |
| Asn | Lys | Tyr | Thr | Phe | Trp | Glu | Val | Asn | Leu | Lys | Glu | Lys | Phe | Ser | Ala |
|     |     |     | 435 |     |     |     |     | 440 |     |     |     |     | 445 |     |     |
| Asp | Leu | Asp | Gln | Phe | Pro | Leu | Gly | Arg | Lys | Phe | Leu | Leu | Gln | Ser | Gly |
|     | 450 |     |     |     |     | 455 |     |     |     |     | 460 |     |     |     |     |
| Leu | Lys | Ala | Lys | Pro | Arg | Leu | Lys | Arg | Ser | Ala | Pro | Thr | Thr | Arg | Ala |
| 465 |     |     |     |     | 470 |     |     |     |     | 475 |     |     |     |     | 480 |
| Pro | Ser | Thr | Lys | Arg | Lys | Lys | Val | Lys | Lys |
|     |     |     |     | 485 |     |     |     |     | 490 |

<210> SEQ ID NO 15
<211> LENGTH: 1575
<212> TYPE: DNA
<213> ORGANISM: Artificial Sequence
<220> FEATURE:
<223> OTHER INFORMATION: HPV 58

<400> SEQUENCE: 15

```
atggtgctga tcctgtgctg caccctggcc atcctgttct gcgtggccga cgtgaacgtg      60
ttccacatct tcctgcagat gagcgtgtgg aggcccagcg aggccaccgt gtacctgccc     120
cccgtgcccg tgagcaaggt ggtgagcacc gacgagtacg tgagcaggac cagcatctac     180
tactacgccg gcagcagcag gctgctggcc gtgggcaacc cctacttcag catcaagagc     240
cccaacaaca caagaaggt gctggtgccc aaggtgagcg gcctgcagta cagggtgttc     300
agggtgaggc tgcccgaccc caacaagttc ggcttccccg acaccagctt ctacaacccc     360
gacacccaga ggctggtgtg ggcctgcgtg ggcctggaga tcggcagggg ccagcccctg     420
ggcgtgggcg tgagcggcca ccctacctg aacaagttcg acgacaccga gaccagcaac     480
aggtaccccg cccagcccgg cagcgacaac agggagtgcc tgagcatgga ctacaagcag     540
acccagctgt gcctgatcgg ctgcaagccc cccaccggcg agcactgggg caagggcgtg     600
gcctgcaaca acaacgccgc cgccaccgac tgccccccccc tggagctgtt caacagcatc     660
atcgaggacg gcgacatggt ggacaccggc ttcggctgca tggacttcgg caccctgcag     720
gccaacaaga gcgacgtgcc catcgacatc tgcaacagca cctgcaagta ccccgactac     780
ctgaagatgg ccagcgagcc ctacggcgac agcctgttct tcttcctgag gagggagcag     840
atgttcgtga ggcacttctt caacagggcc ggcaagctgg gcgaggccgt gcccgacgac     900
ctgtacatca agggcagcgg caacaccgcc gtgatccaga gcagcgcctt cttccccacc     960
```

```
cccagcggca gcatcgtgac cagcgagagc cagctgttca acaagcccta ctggctgcag    1020
agggcccagg gccacaacaa cggcatctgc tggggcaacc agctgttcgt gaccgtggtg    1080
gacaccacca ggagcaccaa catgaccctg tgcaccgagg tgaccaagga gggcacctac    1140
aagaacgaca acttcaagga gtacgtgagg cacgtggagg agtacgacct gcagttcgtg    1200
ttccagctgt gcaagatcac cctgaccgcc gagatcatga cctacatcca ccatggac     1260 agcaacatcc tggaggactg gcagttcggc ctgacccccc ccccagcgc cagcctgcag     1320 gacacctaca ggttcgtgac cagccaggcc atcacctgcc agaagaccgc ccccccaag    1380 gagaaggagg accccctgaa caagtacacc ttctgggagg tgaacctgaa ggagaagttc    1440
agcgccgacc tggaccagtt ccccctgggc aggaagttcc tgctgcagag cggcctgaag    1500
gccaagccca ggctgaagag gagcgccccc accaccaggg cccccagcac caagaggaag    1560
aaggtgaaga agtga                                                    1575

<210> SEQ ID NO 16
<211> LENGTH: 1500
<212> TYPE: DNA
<213> ORGANISM: Artificial Sequence
<220> FEATURE:
<223> OTHER INFORMATION: HPV 33

<400> SEQUENCE: 16
atgagcgtgt ggaggcccag cgaggccacc gtgtacctgc cccccgtgcc cgtgagcaag     60
gtggtgagca ccgacgagta cgtgagcagg accagcatct actactacgc cggcagcagc    120
aggctgctgg ccgtgggcca ccctacttc agcatcaaga ccccaccaa cgccaagaag      180 ctgctggtgc caaggtgag cggcctgcag tacagggtgt tcagggtgag gctgcccgac     240
cccaacaagt tcggcttccc cgacaccagc ttctacaacc ccgacaccca gaggctggtg    300
tgggcctgcg tgggcctgga gatcggcagg ggccagcccc tgggcgtggg catcagcggc    360 cacccctgc tgaacaagtt cgacgacacc gagaccggca caagtaccc cggccagccc     420 ggcgccgaca cagggagtg cctgagcatg gactacaagc agacccagct gtgcctgctg    480
ggctgcaagc ccccaccgg cgagcactgg ggcaagggcg tggcctgcac caacgccgcc    540
cccgccaacg actgcccccc cctggagctg atcaacacca tcatcgagga cggcgacatg    600
gtggacaccg gcttcggctg catggacttc aagaccctgc aggccaacaa gagcgacgtg    660
cccatcgaca tctgcggcag cacctgcaag taccccgact acctgaagat gaccagcgag    720
ccctacggcg acagcctgtt cttcttcctg aggaggggagc agatgttcgt gaggcacttc    780
ttcaacaggg ccggcaccct gggcgaggcc gtgcccgacg acctgtacat caagggcagc    840
ggcaccaccg ccagcatcca gagcagcgcc ttcttcccca cccccagcgg cagcatggtg    900
accagcgaga gccagctgtt caacaagccc tactggctgc agagggccca gggccacaac    960
aacggcatct gctggggcaa ccaggtgttc gtgaccgtgg tggacaccac caggagcacc    1020
aacatgaccc tgtgcaccca ggtgaccagc gacagcacct acaagaacga gaacttcaag    1080
gagtacatca gcacgtgga ggagtacgac ctgcagttcg tgttccagct gtgcaaggtg     1140
accctgaccg ccgaggtgat gacctacatc cacgccatga ccccgacat cctggaggac    1200 tggcagttcg gcctgacccc ccccccagc gccagcctgc aggacaccta caggttcgtg    1260
accagccagg ccatcacctg ccagaagacc gtgccccca aggagaagga ggacccctg     1320 ggcaagtaca ccttctggga ggtggacctg aaggagaagt tcagcgccga cctggaccag    1380
```

```
ttccccctgg gcaggaagtt cctgctgcag gccggcctga aggccaagcc caagctgaag      1440
agggccgccc ccaccagcac caggaccagc agcgccaaga ggaagaaggt gaagaagtga      1500
```

<210> SEQ ID NO 17
<211> LENGTH: 1590
<212> TYPE: DNA
<213> ORGANISM: Artificial Sequence
<220> FEATURE:
<223> OTHER INFORMATION: HPV 52

<400> SEQUENCE: 17

```
atggtgcaga tcctgttcta catcctggtg atcttctact acgtggccgg cgtgaacgtg       60
ttccacatct tcctgcagat gagcgtgtgg aggcccagcg aggccaccgt gtacctgccc      120
cccgtgcccg tgagcaaggt ggtgagcacc gacgagtacg tgagcaggac cagcatctac      180
tactacgccg gcagcagcag gctgctgacc gtgggccacc cctacttcag catcaagaac      240
accagcagcg gcaacggcaa gaaggtgctg gtgcccaagg tgagcggcct gcagtacagg      300
gtgttcagga tcaagctgcc cgaccccaac aagttcggct tccccgacac cagcttctac      360
aaccccgaga cccagaggct ggtgtgggcc tgcaccggcc tggagatcgg caggggccag      420
cccctgggcg tgggcatcag cggccacccc ctgctgaaca agttcgacga caccgagacc      480
agcaacaagt acgccggcaa gcccggcatc gacaacaggg agtgcctgag catggactac      540
aagcagaccc agctgtgcat cctgggctgc aagccccca tcggcgagca ctggggcaag      600
ggcaccccct gcaacaacaa cagcggcaac cccggcgact gccccccct gcagctgatc      660 aacagcgtga tccaggacgg cgacatggtg gacaccggct tcggctgcat ggacttcaac      720
accctgcagg ccagcaagag cgacgtgccc atcgacatct gcagcagcgt gtgcaagtac      780
cccgactacc tgcagatggc cagcgagccc tacggcgaca gcctgttctt cttcctgagg      840
agggagcaga tgttcgtgag gcacttcttc aacagggccg gcacccgggg cgaccccgtg      900
cccggcgacc tgtacatcca gggcagcaac agcggcaaca ccgccaccgt gcagagcagc      960
gccttcttcc ccacccccag cggcagcatg gtgaccagcg agagccagct gttcaacaag     1020
ccctactggc tgcagagggc ccagggccac aacaacggca tctgctgggg caaccagctg     1080
ttcgtgaccg tggtggacac caccaggagc accaacatga ccctgtgcgc cgaggtgaag     1140
aaggagagca cctacaagaa cgagaacttc aaggagtacc tgaggcacgg cgaggagttc     1200
gacctgcagt tcatcttcca gctgtgcaag atcaccctga ccgccgacgt gatgacctac     1260
atccacaaga tggacgccac catcctggag gactggcagt tcggcctgac cccccccccc     1320
agcgccagcc tggaggacac ctacaggttc gtgaccagca ccgccatcac ctgccagaag     1380
aacacccccc caagggcaa ggaggacccc ctgaaggact acatgttctg ggaggtggac     1440
ctgaaggaga agttcagcgc cgacctggac cagttccccc tgggcaggaa gttcctgctg     1500
caggccggcc tgcaggccag gcccaagctg aagaggcccg ccagcagcgc ccccaggacc     1560
agcaccaaga agaagaaggt gaagaggtga                                       1590
```

<210> SEQ ID NO 18
<211> LENGTH: 1473
<212> TYPE: DNA
<213> ORGANISM: Artificial Sequence
<220> FEATURE:
<223> OTHER INFORMATION: H58N35-33T1

<400> SEQUENCE: 18

```
atgaccgtgt acctgccccc cgtgcccgtg agcaaggtgg tgagcaccga cgagtacgtg       60
```

```
agcaggacca gcatctacta ctacgccggc agcagcaggc tgctggccgt gggcaacccc      120
tacttcagca tcaagaatcc cactaacgct aaaaaattac tggtgcccaa ggtgagcggc      180
ctgcagtaca gggtgttcag ggtgaggctg cccgacccca caagttcgg cttccccgac       240 accagcttct acaaccccga cacccagagg ctggtgtggg cctgcgtggg cctggagatc      300
ggcaggggcc agcccctggg cgtgggcgtg agcggccacc cctacctgaa caagttcgac      360
gacaccgaga ccagcaacag gtaccccgcc cagcccggca gcgacaacag ggagtgcctg      420
agcatggact acaagcagac ccagctgtgc ctgatcggct gcaagccccc caccggcgag      480
cactggggca agggcgtggc ctgcaacaac aacgccgccg ccaccgactg ccccccctg       540 gagctgttca acagcatcat cgaggacggc gacatggtgg acaccggctt cggctgcatg      600
gacttcggca ccctgcaggc caacaagagc gacgtgccca tcgacatctg caacagcacc      660
tgcaagtacc ccgactacct gaagatggcc agcgagccct acggcgacag cctgttcttc      720
ttcctgagga gggagcagat gttcgtgagg cacttcttca cagggccgg caagctgggc       780 gaggccgtgc ccgacgacct gtacatcaag ggcagcggca acaccgccgt gatccagagc      840
agcgccttct cccccacccc cagcggcagc atcgtgacca gcgagagcca gctgttcaac      900
aagccctact ggctgcagag ggcccagggc cacaacaacg gcatctgctg gggcaaccag      960
ctgttcgtga ccgtggtgga caccaccagg agcaccaaca tgaccctgtg caccgaggtg     1020
accaaggagg gcacctacaa gaacgacaac ttcaaggagt acgtgaggca cgtggaggag     1080
tacgacctgc agttcgtgtt ccagctgtgc aagatcaccc tgaccgccga gatcatgacc     1140
tacatccaca ccatggacag caacatcctg gaggactggc agttcggcct gaccccccc      1200 cccagcgcca gcctgcagga cacctacagg ttcgtgacca gccaggccat cacctgccag     1260
aagaccgccc ccccaagga aggaggac cccctgaaca gtacaccctt ctgggaggtg        1320
aacctgaagg agaagttcag cgccgacctg gaccagttcc ccctgggcag gaagttcctg     1380
ctgcagagcg gcctgaaggc caagcccagg ctgaagagga gcgcccccac caccagggcc     1440
cccagcacca gaggaagaa ggtgaagaag taa                                   1473
```

<210> SEQ ID NO 19
<211> LENGTH: 1473
<212> TYPE: DNA
<213> ORGANISM: Artificial Sequence
<220> FEATURE:
<223> OTHER INFORMATION: H58N35-33T2-1

<400> SEQUENCE: 19

```
atgaccgtgt acctgccccc cgtgcccgtg agcaaggtgg tgagcaccga cgagtacgtg       60
agcaggacca gcatctacta ctacgccggc agcagcaggc tgctggccgt gggcaacccc      120
tacttcagca tcaagagccc caacaacaac aagaaggtgc tggtgcccaa ggtgagcggc      180
ctgcagtaca gggtgttcag ggtgaggctg cccgacccca caagttcgg cttccccgac       240 accagcttct acaaccccga cacccagagg ctggtgtggg cctgcgtggg cctggagatc      300
ggcaggggcc agcccctggg cgtcggaata agcggccacc ccttactgaa caagttcgac      360
gacaccgaga ccagcaacag gtaccccgcc cagcccggca gcgacaacag ggagtgcctg      420
agcatggact acaagcagac ccagctgtgc ctgatcggct gcaagccccc caccggcgag      480
cactggggca agggcgtggc ctgcaacaac aacgccgccg ccaccgactg ccccccctg       540 gagctgttca acagcatcat cgaggacggc gacatggtgg acaccggctt cggctgcatg      600
```

```
gacttcggca ccctgcaggc caacaagagc gacgtgccca tcgacatctg caacagcacc      660
tgcaagtacc ccgactacct gaagatggcc agcgagccct acggcgacag cctgttcttc      720
ttcctgagga gggagcagat gttcgtgagg cacttcttca cagggccgg caagctgggc       780 gaggccgtgc ccgacgacct gtacatcaag ggcagcggca acaccgccgt gatccagagc      840
agcgccttct tccccacccc cagcggcagc atcgtgacca gcgagagcca gctgttcaac      900 aagcccact ggctgcagag ggcccagggc acaacaacg gcatctgctg ggcaaccag         960 ctgttcgtga ccgtggtgga caccaccagg agcaccaaca tgaccctgtg caccgaggtg     1020
accaaggagg gcacctacaa gaacgacaac ttcaaggagt acgtgaggca cgtggaggag     1080
tacgacctgc agttcgtgtt ccagctgtgc aagatcaccc tgaccgccga gatcatgacc     1140
tacatccaca ccatggacag caacatcctg gaggactggc agttcggcct gacccccccc     1200
cccagcgcca gcctgcagga cacctacagg ttcgtgacca gccaggccat cacctgccag     1260
aagaccgccc cccccaagga gaaggaggac cccctgaaca agtacacctt ctggggaggtg    1320 aacctgaagg agaagttcag cgccgacctg gaccagttcc ccctgggcag gaagttcctg     1380
ctgcagagcg gcctgaaggc caagcccagg ctgaagagga gcgcccccac caccagggcc     1440
cccagcacca gaggaagaa ggtgaagaag tga                                   1473
```

<210> SEQ ID NO 20
<211> LENGTH: 1473
<212> TYPE: DNA
<213> ORGANISM: Artificial Sequence
<220> FEATURE:
<223> OTHER INFORMATION: H58N35-33T2-2

<400> SEQUENCE: 20

```
atgaccgtgt acctgccccc cgtgcccgtg agcaaggtgg tgagcaccga cgagtacgtg       60
agcaggacca gcatctacta ctacgccggc agcagcaggc tgctggccgt gggcaacccc     120
tacttcagca tcaagagccc caacaacaac aagaaggtgc tggtgcccaa ggtgagcggc     180
ctgcagtaca gggtgttcag ggtgaggctg cccgacccca caagttcgg cttccccgac      240 accagcttct acaaccccga caccagagg ctggtgtggg cctgcgtggg cctggagatc      300
ggcaggggcc agcccctggg cgtcggaata agcggccacc ccttactgaa caagttcgac     360
gacaccgaga ccggaaacaa gtaccccgcc cagcccggca gcgacaacag ggagtgcctg     420
agcatggact acaagcagac ccagctgtgc ctgatcggct gcaagccccc caccggcgag     480
cactggggca aggggcgtggc ctgcaacaac aacgccgccg ccaccgactg cccccccctg    540
gagctgttca acagcatcat cgaggacggc gacatggtgg acaccggctt cggctgcatg     600
gacttcggca ccctgcaggc caacaagagc gacgtgccca tcgacatctg caacagcacc     660
tgcaagtacc ccgactacct gaagatggcc agcgagccct acggcgacag cctgttcttc     720
ttcctgagga gggagcagat gttcgtgagg cacttcttca cagggccgg caagctgggc      780 gaggccgtgc ccgacgacct gtacatcaag ggcagcggca acaccgccgt gatccagagc     840
agcgccttct tccccacccc cagcggcagc atcgtgacca gcgagagcca gctgttcaac     900 aagcccact ggctgcagag ggcccagggc acaacaacg gcatctgctg ggcaaccag        960 ctgttcgtga ccgtggtgga caccaccagg agcaccaaca tgaccctgtg caccgaggtg    1020
accaaggagg gcacctacaa gaacgacaac ttcaaggagt acgtgaggca cgtggaggag    1080
tacgacctgc agttcgtgtt ccagctgtgc aagatcaccc tgaccgccga gatcatgacc    1140
tacatccaca ccatggacag caacatcctg gaggactggc agttcggcct gacccccccc    1200
```

```
cccagcgcca gcctgcagga cacctacagg ttcgtgacca gccaggccat cacctgccag    1260
aagaccgccc cccccaagga aaggaggac ccctgaaca agtacaccct ctgggaggtg      1320
aacctgaagg agaagttcag cgccgacctg gaccagttcc cctgggcag gaagttcctg     1380 ctgcagagcg gcctgaaggc caagcccagg ctgaagagga gcgcccccac caccagggcc   1440
cccagcacca agaggaagaa ggtgaagaag tga                                1473
```

<210> SEQ ID NO 21
<211> LENGTH: 1473
<212> TYPE: DNA
<213> ORGANISM: Artificial Sequence
<220> FEATURE:
<223> OTHER INFORMATION: H58N35-33T2

<400> SEQUENCE: 21

```
atgaccgtgt acctgccccc cgtgcccgtg agcaaggtgg tgagcaccga cgagtacgtg    60
agcaggacca gcatctacta ctacgccggc agcagcaggc tgctggccgt gggcaacccc   120
tacttcagca tcaagagccc caacaacaac aagaaggtgc tggtgcccaa ggtgagcggc   180
ctgcagtaca gggtgttcag ggtgaggctg cccgacccca acaagttcgg cttccccgac   240
accagcttct acaaccccga cacccagagg ctggtgtggg cctgcgtggg cctggagatc   300
ggcaggggcc agccctgggt cgtcggaata agcggccacc ccttactgaa caagttcgac   360
gacaccgaga ccggaaacaa gtaccccgga cagcccggcg ctgacaacag ggagtgcctg   420
agcatggact acaagcagac ccagctgtgc ctgatcggct gcaagccccc caccggcgag   480
cactggggca agggcgtggc ctgcaacaac aacgccgccg ccaccgactg ccccccctg    540 gagctgttca acagcatcat cgaggacggc gacatggtgg acaccggctt cggctgcatg   600
gacttcggca ccctgcaggc caacaagagc gacgtgccca tcgacatctg caacagcacc   660
tgcaagtacc ccgactacct gaagatggcc agcgagccct acggcgacag cctgttcttc   720
ttcctgagga gggagcagat gttcgtgagg cacttcttca cagggccgg caagctgggc   780 gaggccgtgc ccgacgacct gtacatcaag ggcagcggca acaccgccgt gatccagagc   840
agcgccttct cccccacccc cagcggcagc atcgtgacca gcgagagcca gctgttcaac   900
aagccctact ggctgcagag ggcccagggc cacaacaacg gcatctgctg gggcaaccag   960
ctgttcgtga ccgtggtgga caccaccagg agcaccaaca tgaccctgtg caccgaggtg   1020
accaaggagg gcacctacaa gaacgacaac ttcaaggagt acgtgaggca cgtggaggag   1080
tacgacctgc agttcgtgtt ccagctgtgc aagatcaccc tgaccgccga gatcatgacc   1140
tacatccaca ccatggacag caacatcctg gaggactggc agttcggcct gacccccccc   1200
cccagcgcca gcctgcagga cacctacagg ttcgtgacca gccaggccat cacctgccag   1260
aagaccgccc cccccaagga aaggaggac ccctgaaca agtacaccct ctgggaggtg     1320
aacctgaagg agaagttcag cgccgacctg gaccagttcc cctgggcag gaagttcctg    1380 ctgcagagcg gcctgaaggc caagcccagg ctgaagagga gcgcccccac caccagggcc  1440
cccagcacca agaggaagaa ggtgaagaag taa                                1473
```

<210> SEQ ID NO 22
<211> LENGTH: 1473
<212> TYPE: DNA
<213> ORGANISM: Artificial Sequence
<220> FEATURE:
<223> OTHER INFORMATION: H58N35-33T3

<400> SEQUENCE: 22

```
atgaccgtgt acctgccccc cgtgcccgtg agcaaggtgg tgagcaccga cgagtacgtg      60
agcaggacca gcatctacta ctacgccggt agcagcaggc tgctggccgt gggcaacccc     120
tacttcagca tcaagagccc caacaacaac aagaaggtgc tggtgcccaa ggtgagcggc     180
ctgcagtaca gggtgttcag ggtgaggctg cccgacccca caagttcgg cttccccgac      240
accagcttct acaaccccga cacccagagg ctggtgtggg cctgcgtggg cctggagatc     300
ggcaggggcc agcccctggg cgtgggcgtg agcggccacc cctacctgaa caagttcgac     360
gacaccgaga ccagcaacag gtaccccgcc cagcccggca gcgacaacag ggagtgcctg     420
agcatggact acaagcagac ccagctgtgc ctgatcggct gcaagccccc caccggcgag     480
cactgggcca aggagtagc atgtacaaac gctgcacctg ccaacgactg ccccccctg      540
gagctgttca acagcatcat cgaggacggc gacatggtgg acaccggctt cggctgcatg     600
gacttcggca ccctgcaggc caacaagagc gacgtgccca tcgacatctg caacagcacc     660
tgcaagtacc ccgactacct gaagatggcc agcgagcccc acggcgacag cctgttcttc     720
ttcctgagga gggagcagat gttcgtgagg cacttcttca cagggccgg caagctgggc     780
gaggccgtgc ccgacgacct gtacatcaag ggcagcggca caccgccgt gatccagagc     840
agcgccttct cccccacccc cagcggcagc atcgtgacca gcgagagcca gctgttcaac     900
aagcccact ggctgcagag ggcccagggc acaacaacg gcatctgctg gggcaaccag     960
ctgttcgtga ccgtggtgga caccaccagg agcaccaaca tgaccctgtg caccgaggtg    1020
accaaggagg gcacctacaa gaacgacaac ttcaaggagt acgtgaggca cgtggaggag    1080
tacgacctgc agttcgtgtt ccagctgtgc aagatcaccc tgaccgccga gatcatgacc    1140
tacatccaca ccatggacag caacatcctg gaggactggc agttcggcct gacccccccc    1200
cccagcgcca gcctgcagga cacctacagg ttcgtgacca gccaggccat cacctgccag    1260
aagaccgccc cccccaagga gaaggaggac ccccctgaaca agtacacctt ctgggaggtg    1320
aaccctgaagg agaagttcag cgccgacctg gaccagttcc ccctgggcag gaagttcctg    1380
ctgcagagcg gcctgaaggc caagcccagg ctgaagagga gcgcccccac caccagggcc    1440
cccagcacca agaggaagaa ggtgaagaag taa                                 1473
```

<210> SEQ ID NO 23
<211> LENGTH: 1473
<212> TYPE: DNA
<213> ORGANISM: Artificial Sequence
<220> FEATURE:
<223> OTHER INFORMATION: H58N35-33T4

<400> SEQUENCE: 23

```
atgaccgtgt acctgccccc cgtgcccgtg agcaaggtgg tgagcaccga cgagtacgtg      60
agcaggacca gcatctacta ctacgccggc agcagcaggc tgctggccgt gggcaacccc     120
tacttcagca tcaagagccc caacaacaac aagaaggtgc tggtgcccaa ggtgagcggc     180
ctgcagtaca gggtgttcag ggtgaggctg cccgacccca caagttcgg cttccccgac      240
accagcttct acaaccccga cacccagagg ctggtgtggg cctgcgtggg cctggagatc     300
ggcaggggcc agcccctggg cgtgggcgtg agcggccacc cctacctgaa caagttcgac     360
gacaccgaga ccagcaacag gtaccccgcc cagcccggca gcgacaacag ggagtgcctg     420
agcatggact acaagcagac ccagctgtgc ctgatcggct gcaagccccc caccggcgag     480
cactgggcca agggcgtggc ctgcaacaac aacgccgccg ccaccgactg ccccccctg      540
```

```
gagctgttca acagcatcat cgaggacggc gacatggtgg acaccggctt cggctgcatg    600
gacttcggca ccctgcaggc caacaagagc gacgtgccca tcgacatctg caacagcacc    660
tgcaagtacc ccgactacct gaagatggcc agcgagccct acggcgacag cctgttcttc    720
ttcctgagga gggagcagat gttcgtgagg cacttcttca cagggccgg caagctgggc      780 gaggccgtgc ccgacgacct gtacatcaag ggcagcggca acagcaag tatccagagc       840 agcgccttct tccccacccc cagcggcagc atcgtgacca gcgagagcca gctgttcaac    900
aagccctact ggctgcagag ggcccagggc acaacaacg gcatctgctg gggcaaccag       960
ctgttcgtga ccgtggtgga caccaccagg agcaccaaca tgaccctgtg caccgaggtg    1020
accaaggagg gcacctacaa gaacgacaac ttcaaggagt acgtgaggca cgtggaggag    1080
tacgacctgc agttcgtgtt ccagttgtgc aagatcaccc tgaccgccga gatcatgacc    1140
tacatccaca ccatggacag caacatcctg gaggactggc agttcggcct gacccccccc    1200
cccagcgcca gcctgcagga cacctacagg ttcgtgacca gccaggccat cacctgccag    1260
aagaccgccc cccccaagga aaggaggac ccctgaaca agtacaccct ctgggaggtg      1320
aacctgaagg agaagttcag cgccgacctg gaccagttcc ccctgggcag gaagttcctg    1380
ctgcagagcg gcctgaaggc caagcccagg ctgaagagga gcgcccccac caccagggcc    1440
cccagcacca agaggaagaa ggtgaagaag taa                                  1473

<210> SEQ ID NO 24
<211> LENGTH: 1473
<212> TYPE: DNA
<213> ORGANISM: Artificial Sequence
<220> FEATURE:
<223> OTHER INFORMATION: H58N35-33T5

<400> SEQUENCE: 24
atgaccgtgt acctgccccc cgtgcccgtg agcaaggtgg tgagcaccga cgagtacgtg      60
agcaggacca gcatctacta ctacgccggc agcagcaggc tgctggccgt gggcaacccc    120
tacttcagca tcaagagccc caacaacaac aagaaggtgc tggtgcccaa ggtgagcggc    180
ctgcagtaca gggtgttcag ggtgaggctg cccgacccca caagttcgg cttccccgac      240 accagcttct acaaccccga cacccagagg ctggtgtggg cctgcgtggg cctggagatc    300 ggcagggggcc agcccctggg cgtgggcgtg agcggccacc cctacctgaa caagttcgac    360
gacaccgaga ccagcaacag gtaccccgcc cagcccggca gcgacaacag ggagtgcctg    420
agcatggact acaagcagac ccagctgtgc ctgatcggct gcaagccccc caccggcgag    480
cactggggca agggcgtggc ctgcaacaac aacgccgccg ccaccgactg cccccccctg    540
gagctgttca acagcatcat cgaggacggc gacatggtgg acaccggctt cggctgcatg    600
gacttcggca ccctgcaggc caacaagagc gacgtgccca tcgacatctg caacagcacc    660
tgcaagtacc ccgactacct gaagatggcc agcgagccct acggcgacag cctgttcttc    720
ttcctgagga gggagcagat gttcgtgagg cacttcttca cagggccgg caagctgggc      780 gaggccgtgc ccgacgacct gtacatcaag ggcagcggca acaccgccgt gatccagagc    840
agcgccttct tccccacccc cagcggcagc atcgtgacca gcgagagcca gctgttcaac    900
aagccctact ggctgcagag ggcccagggc acaacaacg gcatctgctg gggcaaccag       960
ctgttcgtga ccgtggtgga caccaccagg agcaccaaca tgaccctgtg caccgaggtg    1020
accagcgaca gcacgtacaa gaacgagaac ttcaaggagt acgtgaggca cgtggaggag    1080
```

| | |
|---|---|
| tacgacctgc agttcgtgtt ccagctgtgc aagatcaccc tgaccgccga gatcatgacc | 1140 |
| tacatccaca ccatggacag caacatcctg gaggactggc agttcggcct gacccccccc | 1200 |
| cccagcgcca gcctgcagga cacctacagg ttcgtgacca gccaggccat cacctgccag | 1260 |
| aagaccgccc cccccaagga gaaggaggac cccctgaaca agtacacctt ctgggaggtg | 1320 |
| aacctgaagg agaagttcag cgccgacctg gaccagttcc ccctgggcag gaagttcctg | 1380 |
| ctgcagagcg gcctgaaggc caagcccagg ctgaagagga gcgcccccac caccagggcc | 1440 |
| cccagcacca agaggaagaa ggtgaagaag taa | 1473 |

<210> SEQ ID NO 25
<211> LENGTH: 1473
<212> TYPE: DNA
<213> ORGANISM: Artificial Sequence
<220> FEATURE:
<223> OTHER INFORMATION: H58N35-33T1-52S1

<400> SEQUENCE: 25

| | |
|---|---|
| atgaccgtgt acctgccccc cgtgcccgtg agcaaggtgg tgagcaccga cgagtacgtg | 60 |
| agcaggacca gcatctacta ctacgccggc agcagcaggc tgctggccgt gggcaacccc | 120 |
| tacttcagca tcaagaatcc cactaacgct aaaaaattac tggtgcccaa ggtgagcggc | 180 |
| ctgcagtaca gggtgttcag ggtgaggctg cccgacccca caagttcgg cttccccgac | 240 |
| accagcttct acaaccccga cacccagagg ctggtgtggg cctgcgtggg cctggagatc | 300 |
| ggcaggggcc agcccctggg cgtgggcatc agcggccacc ccctgctgaa caagttcgac | 360 |
| gacaccgaga ccagcaacaa gtacgccggc aagcccggca tcgacaacag ggagtgcctg | 420 |
| agcatggact acaagcagac ccagctgtgc ctgatcggct gcaagccccc caccggcgag | 480 |
| cactgggcca agggcgtggc ctgcaacaac aacgccgccg ccaccgactg ccccccctg | 540 |
| gagctgttca cagcatcat cgaggacggc gacatggtgg acaccggctt cggctgcatg | 600 |
| gacttcggca ccctgcaggc caacaagagc gacgtgccca tcgacatctg caacagcacc | 660 |
| tgcaagtacc ccgactacct gaagatggcc agcgagccct acggcgacag cctgttcttc | 720 |
| ttcctgagga gggagcagat gttcgtgagg cacttcttca cagggccgg caagctgggc | 780 |
| gaggccgtgc ccgacgacct gtacatcaag ggcagcggca caccgccgt gatccagagc | 840 |
| agcgccttct cccccacccc cagcggcagc atcgtgacca gcgagagcca gctgttcaac | 900 |
| aagccctact ggctgcagag ggcccagggc acaacaacg gcatctgctg gggcaaccag | 960 |
| ctgttcgtga ccgtggtgga caccaccagg agcaccaaca tgaccctgtg caccgaggtg | 1020 |
| accaaggagg gcacctacaa gaacgacaac ttcaaggagt acgtgaggca cgtggaggag | 1080 |
| tacgacctgc agttcgtgtt ccagctgtgc aagatcaccc tgaccgccga gatcatgacc | 1140 |
| tacatccaca ccatggacag caacatcctg gaggactggc agttcggcct gacccccccc | 1200 |
| cccagcgcca gcctgcagga cacctacagg ttcgtgacca gccaggccat cacctgccag | 1260 |
| aagaccgccc cccccaagga gaaggaggac cccctgaaca agtacacctt ctgggaggtg | 1320 |
| aacctgaagg agaagttcag cgccgacctg gaccagttcc ccctgggcag gaagttcctg | 1380 |
| ctgcagagcg gcctgaaggc caagcccagg ctgaagagga gcgcccccac caccagggcc | 1440 |
| cccagcacca agaggaagaa ggtgaagaag taa | 1473 |

<210> SEQ ID NO 26
<211> LENGTH: 1476
<212> TYPE: DNA
<213> ORGANISM: Artificial Sequence

<220> FEATURE:
<223> OTHER INFORMATION: H58N35-33T1-52S2

<400> SEQUENCE: 26

| | | | | |
|---|---|---|---|---|
| atgaccgtgt | acctgccccc | cgtgcccgtg | agcaaggtgg tgagcaccga cgagtacgtg | 60 |
| agcaggacca | gcatctacta | ctacgccggc | agcagcaggc tgctggccgt gggcaacccc | 120 |
| tacttcagca | tcaagaatcc | cactaacgct | aaaaaattac tggtgcccaa ggtgagcggc | 180 |
| ctgcagtaca | gggtgttcag | ggtgaggctg | cccgaccccA acaagttcgg cttccccgac | 240 |
| accagcttct | acaaccccga | cacccagagg | ctggtgtggg cctgcgtggg cctggagatc | 300 |
| ggcaggggcc | agcccctggg | cgtgggcgtg | agcggccacc cctacctgaa caagttcgac | 360 |
| gacaccgaga | ccagcaacag | gtaccccgcc | cagcccggca gcgacaacag ggagtgcctg | 420 |
| agcatggact | acaagcagac | ccagctgtgc | ctgatcggct gcaagccccc caccggcgag | 480 |
| cactggggca | agggcacccc | ctgcaacaac | aacagcggca accccggcga ctgccccccc | 540 |
| ctggagctgt | tcaacagcat | catcgaggac | ggcgacatgg tggacaccgg cttcggctgc | 600 |
| atggacttcg | gcaccctgca | ggccaacaag | agcgacgtgc ccatcgacat ctgcaacagc | 660 |
| acctgcaagt | accccgacta | cctgaagatg | gccagcgagc cctacggcga cagcctgttc | 720 |
| ttcttcctga | ggagggagca | gatgttcgtg | aggcacttct tcaacagggc cggcaagctg | 780 |
| ggcgaggccg | tgcccgacga | cctgtacatc | aagggcagcg gcaacaccgc cgtgatccag | 840 |
| agcagcgcct | tcttccccac | ccccagcggc | agcatcgtga ccagcgagag ccagctgttc | 900 |
| aacaagccct | actggctgca | gagggcccag | ggccacaaca cggcatctg ctggggcaac | 960 |
| cagctgttcg | tgaccgtggt | ggacaccacc | aggagcacca catgaccct gtgcaccgag | 1020 |
| gtgaccaagg | agggcaccta | caagaacgac | aacttcaagg agtacgtgag gcacgtggag | 1080 |
| gagtacgacc | tgcagttcgt | gttccagctg | tgcaagatca ccctgaccgc cgagatcatg | 1140 |
| acctacatcc | acaccatgga | cagcaacatc | ctggaggact ggcagttcgg cctgacccc | 1200 |
| cccccagcg | ccagcctgca | ggacacctac | aggttcgtga ccagccaggc catcacctgc | 1260 |
| cagaagaccg | cccccccaa | ggagaaggag | gaccccctga caagtacac cttctgggag | 1320 |
| gtgaacctga | aggagaagtt | cagcgccgac | ctggaccagt tccccctggg caggaagttc | 1380 |
| ctgctgcaga | gcggcctgaa | ggccaagccc | aggctgaaga ggagcgcccc caccaccagg | 1440 |
| gccccccagca | ccaagaggaa | gaaggtgaag | aagtaa | 1476 |

<210> SEQ ID NO 27
<211> LENGTH: 1479
<212> TYPE: DNA
<213> ORGANISM: Artificial Sequence
<220> FEATURE:
<223> OTHER INFORMATION: H58N35-33T1-52S3

<400> SEQUENCE: 27

| | | | | |
|---|---|---|---|---|
| atgaccgtgt | acctgccccc | cgtgcccgtg | agcaaggtgg tgagcaccga cgagtacgtg | 60 |
| agcaggacca | gcatctacta | ctacgccggc | agcagcaggc tgctggccgt gggcaacccc | 120 |
| tacttcagca | tcaagaatcc | cactaacgct | aaaaaattac tggtgcccaa ggtgagcggc | 180 |
| ctgcagtaca | gggtgttcag | ggtgaggctg | cccgaccccA acaagttcgg cttccccgac | 240 |
| accagcttct | acaaccccga | cacccagagg | ctggtgtggg cctgcgtggg cctggagatc | 300 |
| ggcaggggcc | agcccctggg | cgtgggcgtg | agcggccacc cctacctgaa caagttcgac | 360 |
| gacaccgaga | ccagcaacag | gtaccccgcc | cagcccggca gcgacaacag ggagtgcctg | 420 |

| | |
|---|---|
| agcatggact acaagcagac ccagctgtgc ctgatcggct gcaagccccc caccggcgag | 480 |
| cactggggca agggcgtggc ctgcaacaac aacgccgccg ccaccgactg ccccccctg | 540 |
| gagctgttca acagcatcat cgaggacggc gacatggtgg acaccggctt cggctgcatg | 600 |
| gacttcggca ccctgcaggc caacaagagc gacgtgccca tcgacatctg caacagcacc | 660 |
| tgcaagtacc ccgactacct gaagatggcc agcgagccct acggcgacag cctgttcttc | 720 |
| ttcctgagga gggagcagat gttcgtgagg cacttcttca cagggccgg caccctgggc | 780 |
| gaccccgtgc ccggcgacct gtacatccag ggcagcaaca gcggcaacac cgccaccgtg | 840 |
| cagagcagcg ccttcttccc cacccccagc ggcagcatcg tgaccagcga gagccagctg | 900 |
| ttcaacaagc cctactggct gcagagggcc cagggccaca caacggcat ctgctggggc | 960 |
| aaccagctgt tcgtgaccgt ggtggacacc accaggagca ccaacatgac cctgtgcacc | 1020 |
| gaggtgacca aggagggcac ctacaagaac gacaacttca aggagtacgt gaggcacgtg | 1080 |
| gaggagtacg acctgcagtt cgtgttccag ctgtgcaaga tcaccctgac cgccgagatc | 1140 |
| atgacctaca tccacaccat ggacagcaac atcctggagg actggcagtt cggcctgacc | 1200 |
| cccccccca gcgccagcct gcaggacacc tacaggttcg tgaccagcca ggccatcacc | 1260 |
| tgccagaaga ccgccccccc caaggagaag gaggacccc tgaacaagta caccttctgg | 1320 |
| gaggtgaacc tgaaggagaa gttcagcgcc gacctggacc agttccccct gggcaggaag | 1380 |
| ttcctgctgc agagcggcct gaaggccaag cccaggctga agaggagcgc ccccaccacc | 1440 |
| agggcccca gcaccaagag gaagaaggtg aagaagtaa | 1479 |

<210> SEQ ID NO 28
<211> LENGTH: 1473
<212> TYPE: DNA
<213> ORGANISM: Artificial Sequence
<220> FEATURE:
<223> OTHER INFORMATION: H58N35-33T1-52S4

<400> SEQUENCE: 28

| | |
|---|---|
| atgaccgtgt acctgccccc cgtgcccgtg agcaaggtgg tgagcaccga cgagtacgtg | 60 |
| agcaggacca gcatctacta ctacgccggc agcagcaggc tgctggccgt gggcaacccc | 120 |
| tacttcagca tcaagaatcc cactaacgct aaaaaattac tggtgcccaa ggtgagcggc | 180 |
| ctgcagtaca gggtgttcag ggtgaggctg cccgacccca caagttcgg cttccccgac | 240 |
| accagcttct acaaccccga cacccagagg ctggtgtggg cctgcgtggg cctggagatc | 300 |
| ggcagggggcc agcccctggg cgtgggcgtg agcggccacc cctacctgaa caagttcgac | 360 |
| gacaccgaga ccagcaacag gtaccccgcc cagcccggca gcgacaacag ggagtgcctg | 420 |
| agcatggact acaagcagac ccagctgtgc ctgatcggct gcaagccccc caccggcgag | 480 |
| cactggggca agggcgtggc ctgcaacaac aacgccgccg ccaccgactg ccccccctg | 540 |
| gagctgttca acagcatcat cgaggacggc gacatggtgg acaccggctt cggctgcatg | 600 |
| gacttcggca ccctgcaggc caacaagagc gacgtgccca tcgacatctg caacagcacc | 660 |
| tgcaagtacc ccgactacct gaagatggcc agcgagccct acggcgacag cctgttcttc | 720 |
| ttcctgagga gggagcagat gttcgtgagg cacttcttca cagggccgg caagctgggc | 780 |
| gaggccgtgc ccgacgacct gtacatcaag ggcagcggca accgccgt gatccagagc | 840 |
| agcgccttct cccccacccc cagcggcagc atcgtgacca gcgagagcca gctgttcaac | 900 |
| aagccctact ggctgcagag ggcccagggc cacaacaacg gcatctgctg gggcaaccag | 960 |
| ctgttcgtga ccgtggtgga caccaccagg agcaccaaca tgaccctgtg caccgaggtg | 1020 |

-continued

```
aagaaggaga gcacctacaa gaacgagaac ttcaaggagt acgtgaggca cgtggaggag      1080
tacgacctgc agttcgtgtt ccagctgtgc aagatcaccc tgaccgccga gatcatgacc      1140
tacatccaca ccatggacag caacatcctg gaggactggc agttcggcct gaccccccc       1200 cccagcgcca gcctgcagga cacctacagg ttcgtgacca gccaggccat cacctgccag      1260
aagaccgccc cccccaagga gaaggaggac cccctgaaca agtacacctt ctggggaggtg     1320 aacctgaagg agaagttcag cgccgacctg gaccagttcc ccctgggcag gaagttcctg     1380
ctgcagagcg gcctgaaggc caagcccagg ctgaagagga gcgcccccac caccagggcc     1440
cccagcacca agaggaagaa ggtgaagaag taa                                  1473
```

<210> SEQ ID NO 29
<211> LENGTH: 50
<212> TYPE: DNA
<213> ORGANISM: Artificial Sequence
<220> FEATURE:
<223> OTHER INFORMATION: Primer

<400> SEQUENCE: 29
cttcagcatc aagaatccca ctaacgctaa aaaattactg gtgcccaagg        50

<210> SEQ ID NO 30
<211> LENGTH: 50
<212> TYPE: DNA
<213> ORGANISM: Artificial Sequence
<220> FEATURE:
<223> OTHER INFORMATION: Primer

<400> SEQUENCE: 30
ccttgggcac cagtaatttt ttagcgttag tgggattctt gatgctgaag        50

<210> SEQ ID NO 31
<211> LENGTH: 44
<212> TYPE: DNA
<213> ORGANISM: Artificial Sequence
<220> FEATURE:
<223> OTHER INFORMATION: Primer

<400> SEQUENCE: 31
cctgggcgtc ggaataagcg gccacccctt actgaacaag ttcg              44

<210> SEQ ID NO 32
<211> LENGTH: 44
<212> TYPE: DNA
<213> ORGANISM: Artificial Sequence
<220> FEATURE:
<223> OTHER INFORMATION: Primer

<400> SEQUENCE: 32
cgaacttgtt cagtaagggg tggccgctta ttccgacgcc cagg              44

<210> SEQ ID NO 33
<211> LENGTH: 35
<212> TYPE: DNA
<213> ORGANISM: Artificial Sequence
<220> FEATURE:
<223> OTHER INFORMATION: Primer

<400> SEQUENCE: 33
cgacaccgag accggaaaca agtaccccgc ccagc                        35

<210> SEQ ID NO 34

```
<211> LENGTH: 35
<212> TYPE: DNA
<213> ORGANISM: Artificial Sequence
<220> FEATURE:
<223> OTHER INFORMATION: Primer

<400> SEQUENCE: 34
gctgggcggg gtacttgttt ccggtctcgg tgtcg                              35

<210> SEQ ID NO 35
<211> LENGTH: 40
<212> TYPE: DNA
<213> ORGANISM: Artificial Sequence
<220> FEATURE:
<223> OTHER INFORMATION: Primer

<400> SEQUENCE: 35
aacaagtacc ccggacagcc cggcgctgac aacagggagt                         40

<210> SEQ ID NO 36
<211> LENGTH: 40
<212> TYPE: DNA
<213> ORGANISM: Artificial Sequence
<220> FEATURE:
<223> OTHER INFORMATION: Primer

<400> SEQUENCE: 36
actccctgtt gtcagcgccg ggctgtccgg ggtacttgtt                         40

<210> SEQ ID NO 37
<211> LENGTH: 47
<212> TYPE: DNA
<213> ORGANISM: Artificial Sequence
<220> FEATURE:
<223> OTHER INFORMATION: Primer

<400> SEQUENCE: 37
ggggcaaggg agtagcatgt acaaacgctg cacctgccaa cgactgc                 47

<210> SEQ ID NO 38
<211> LENGTH: 47
<212> TYPE: DNA
<213> ORGANISM: Artificial Sequence
<220> FEATURE:
<223> OTHER INFORMATION: Primer

<400> SEQUENCE: 38
gcagtcgttg gcaggtgcag cgtttgtaca tgctactccc ttgcccc                 47

<210> SEQ ID NO 39
<211> LENGTH: 38
<212> TYPE: DNA
<213> ORGANISM: Artificial Sequence
<220> FEATURE:
<223> OTHER INFORMATION: Primer

<400> SEQUENCE: 39
caagggcagc ggcacaacag caagtatcca gagcagcg                           38

<210> SEQ ID NO 40
<211> LENGTH: 38
<212> TYPE: DNA
<213> ORGANISM: Artificial Sequence
<220> FEATURE:
<223> OTHER INFORMATION: Primer

<400> SEQUENCE: 40
```
cgctgctctg gatacttgct gttgtgccgc tgcccttg                        38

<210> SEQ ID NO 41
<211> LENGTH: 47
<212> TYPE: DNA
<213> ORGANISM: Artificial Sequence
<220> FEATURE:
<223> OTHER INFORMATION: Primer

<400> SEQUENCE: 41
ccgaggtgac cagcgacagc acgtacaaga acgagaactt caaggag              47

<210> SEQ ID NO 42
<211> LENGTH: 47
<212> TYPE: DNA
<213> ORGANISM: Artificial Sequence
<220> FEATURE:
<223> OTHER INFORMATION: Primer

<400> SEQUENCE: 42
ctccttgaag ttctcgttct tgtacgtgct gtcgctggtc acctcgg              47

<210> SEQ ID NO 43
<211> LENGTH: 23
<212> TYPE: DNA
<213> ORGANISM: Artificial Sequence
<220> FEATURE:
<223> OTHER INFORMATION: Primer

<400> SEQUENCE: 43
ctgatcggct gcaagccccc cac                                        23

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
cacgcaggcc cacaccagcc                                            20

<210> SEQ ID NO 45
<211> LENGTH: 25
<212> TYPE: DNA
<213> ORGANISM: Artificial Sequence
<220> FEATURE:
<223> OTHER INFORMATION: Primer

<400> SEQUENCE: 45
gagctgttca acagcatcat cgagg                                      25

<210> SEQ ID NO 46
<211> LENGTH: 22
<212> TYPE: DNA
<213> ORGANISM: Artificial Sequence
<220> FEATURE:
<223> OTHER INFORMATION: Primer

<400> SEQUENCE: 46 ggtgggggc ttgcagccga tc                                          22

<210> SEQ ID NO 47
<211> LENGTH: 22
<212> TYPE: DNA

```
<213> ORGANISM: Artificial Sequence
<220> FEATURE:
<223> OTHER INFORMATION: Primer

<400> SEQUENCE: 47
atcgtgacca gcgagagcca gc                                              22

<210> SEQ ID NO 48
<211> LENGTH: 23
<212> TYPE: DNA
<213> ORGANISM: Artificial Sequence
<220> FEATURE:
<223> OTHER INFORMATION: Primer

<400> SEQUENCE: 48
cttcaggtag tcggggtact tgc                                             23

<210> SEQ ID NO 49
<211> LENGTH: 22
<212> TYPE: DNA
<213> ORGANISM: Artificial Sequence
<220> FEATURE:
<223> OTHER INFORMATION: Primer

<400> SEQUENCE: 49
gtgaggcacg tggaggagta cg                                              22

<210> SEQ ID NO 50
<211> LENGTH: 22
<212> TYPE: DNA
<213> ORGANISM: Artificial Sequence
<220> FEATURE:
<223> OTHER INFORMATION: Primer

<400> SEQUENCE: 50
ggtgcacagg gtcatgttgg tg                                              22

<210> SEQ ID NO 51
<211> LENGTH: 40
<212> TYPE: DNA
<213> ORGANISM: Artificial Sequence
<220> FEATURE:
<223> OTHER INFORMATION: Primer

<400> SEQUENCE: 51
gaggctggtg tgggcctgcg tgggcctgga gatcggcagg                           40

<210> SEQ ID NO 52
<211> LENGTH: 41
<212> TYPE: DNA
<213> ORGANISM: Artificial Sequence
<220> FEATURE:
<223> OTHER INFORMATION: Primer

<400> SEQUENCE: 52 tgggggctt gcagccgatc aggcacagct gggtctgctt g                          41

<210> SEQ ID NO 53
<211> LENGTH: 43
<212> TYPE: DNA
<213> ORGANISM: Artificial Sequence
<220> FEATURE:
<223> OTHER INFORMATION: Primer

<400> SEQUENCE: 53
tgatcggctg caagccccc accggcgagc actggggcaa ggg                        43
```

<210> SEQ ID NO 54
<211> LENGTH: 42
<212> TYPE: DNA
<213> ORGANISM: Artificial Sequence
<220> FEATURE:
<223> OTHER INFORMATION: Primer

<400> SEQUENCE: 54
tcgatgatgc tgttgaacag ctccaggggg gggcagtcgc cg         42

<210> SEQ ID NO 55
<211> LENGTH: 39
<212> TYPE: DNA
<213> ORGANISM: Artificial Sequence
<220> FEATURE:
<223> OTHER INFORMATION: Primer

<400> SEQUENCE: 55
gcaagtaccc cgactacctg aagatggcca gcgagccct            39

<210> SEQ ID NO 56
<211> LENGTH: 38
<212> TYPE: DNA
<213> ORGANISM: Artificial Sequence
<220> FEATURE:
<223> OTHER INFORMATION: Primer

<400> SEQUENCE: 56
gctggctctc gctggtcacg atgctgccgc tgggggtg             38

<210> SEQ ID NO 57
<211> LENGTH: 39
<212> TYPE: DNA
<213> ORGANISM: Artificial Sequence
<220> FEATURE:
<223> OTHER INFORMATION: Primer

<400> SEQUENCE: 57
caccaacatg accctgtgca ccgaggtgaa gaaggagag            39

<210> SEQ ID NO 58
<211> LENGTH: 41
<212> TYPE: DNA
<213> ORGANISM: Artificial Sequence
<220> FEATURE:
<223> OTHER INFORMATION: Primer

<400> SEQUENCE: 58
cgtactcctc cacgtgcctc acgtactcct tgaagttctc g         41

<210> SEQ ID NO 59
<211> LENGTH: 8
<212> TYPE: PRT
<213> ORGANISM: Artificial Sequence
<220> FEATURE:
<223> OTHER INFORMATION: HPV 33

<400> SEQUENCE: 59

Asn Pro Thr Asn Ala Lys Lys Leu
1               5

<210> SEQ ID NO 60
<211> LENGTH: 8
<212> TYPE: PRT
<213> ORGANISM: Artificial Sequence

```
<220> FEATURE:
<223> OTHER INFORMATION: HPV 33

<400> SEQUENCE: 60

Ser Asp Ser Thr Tyr Lys Asn Glu
1               5

<210> SEQ ID NO 61
<211> LENGTH: 25
<212> TYPE: PRT
<213> ORGANISM: Artificial Sequence
<220> FEATURE:
<223> OTHER INFORMATION: HPV 52

<400> SEQUENCE: 61

Ile Ser Gly His Pro Leu Leu Asn Lys Phe Asp Asp Thr Glu Thr Ser
1               5                   10                  15

Asn Lys Tyr Ala Gly Lys Pro Gly Ile
            20                  25

<210> SEQ ID NO 62
<211> LENGTH: 9
<212> TYPE: PRT
<213> ORGANISM: Artificial Sequence
<220> FEATURE:
<223> OTHER INFORMATION: HPV 52

<400> SEQUENCE: 62

Lys Lys Glu Ser Thr Tyr Lys Asn Glu
1               5
```